United States Patent
Høgset et al.

(10) Patent No.: US 10,973,896 B2
(45) Date of Patent: *Apr. 13, 2021

(54) TREATMENT OR PREVENTION OF MELANOMA USING PHOTOCHEMICAL INTERNALIZATION OF A MELANOMA ANTIGEN

(71) Applicant: PCI Biotech AS, Oslo (NO)

(72) Inventors: Anders Høgset, Oslo (NO); Pål Johansen, Winterthur (CH)

(73) Assignee: PCI Biotech AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,314

(22) PCT Filed: Nov. 21, 2014

(86) PCT No.: PCT/EP2014/075339
§ 371 (c)(1),
(2) Date: Oct. 11, 2016

(87) PCT Pub. No.: WO2015/154832
PCT Pub. Date: Oct. 15, 2015

(65) Prior Publication Data
US 2017/0143811 A1 May 25, 2017

(30) Foreign Application Priority Data

Apr. 11, 2014 (GB) .................................. 1406599.9
Aug. 28, 2014 (GB) .................................. 1415254.0

(51) Int. Cl.
| | | |
|---|---|---|
| *A61K 41/00* | (2020.01) | |
| *A61K 39/00* | (2006.01) | |
| *A61N 5/06* | (2006.01) | |
| *C12N 5/0784* | (2010.01) | |

(52) U.S. Cl.
CPC .... *A61K 39/00119* (2018.08); *A61K 39/0011* (2013.01); *A61K 41/0071* (2013.01); *A61N 5/062* (2013.01); *C12N 5/0639* (2013.01); *A61K 2039/5154* (2013.01); *A61K 2039/572* (2013.01); *A61N 2005/0663* (2013.01); *C12N 2501/998* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,498,029 B2 * | 3/2009 | Hasan | ................. | A61K 41/0057 424/143.1 |
| 8,216,587 B1 * | 7/2012 | Berg | ................... | A61K 39/0011 424/193.1 |
| 2005/0013812 A1 * | 1/2005 | Dow | ...................... | A61K 39/02 424/144.1 |

FOREIGN PATENT DOCUMENTS

| | | |
|---|---|---|
| WO | 02/39951 | 5/2002 |
| WO | 2007/133728 | 11/2007 |
| WO | 2011/018636 | 2/2011 |
| WO | WO 2012/009611 | * 1/2012 |
| WO | 2013/189663 | 12/2013 |
| WO | 2014/139597 | 9/2014 |
| WO | 2015/028575 | 3/2015 |

OTHER PUBLICATIONS

Baldea & Filip (Journal of Physiology and Pharmacology, 2012, 63:109-118).*
Cancer Facts (NCI/NIH/DHHS, "Photodynamic Therapy for Cancer: Questions and Answers" published online May 12, 2004.*
Maiya (Resonance, 2000, 6: p. 15-29).*
Rosenberg et al (Nature Medicine, 1998, 4:321-327).*
Cho et al (Cancer Immunology Immunotherapy, 2013, 62:787-799).*
Sabado et al (Journal of Visualized Experiments, 2013, 78:e50085, internet pp. 108).*
Fujimura et al (Eur. J. Immunol. 2006, 36:3371-3380).*
Lee et al (Biomaterials, 2009, 30:2929-2939).*
Håkerud et al., "Intradermal photosensitisation facilitates stimulation of MHC class-I restricted CD8 T-cell responses of co-administered antigen", Journal of Control Release, 174: 143-150 (2014), first published Nov. 23, 2013.
Waeckerle-Men et al., "Photochemical targeting of antigens to the cytosol for stimulation of MHC class-I-restricted T-cell responses", European Journal of Pharmaceutics and Biopharmaceutics, Feb. 1, 2013, XP055060566.
International Search Report and Written Opinion of the International Searching Authority dated Mar. 9, 2015, issued in corresponding International Application No. PCT/EP2014/075339.
Patents Act 1977: Search Report under Section 17(5) dated Apr. 24, 2015 in United Kingdom Application No. GB1406599.9.
Gaware et al., "Tetraphenylporphyrin Tethered Chitosan Based Carriers for Photochemical Transfection", Journal of Medicinal Chemistry, 56(3): 807-819 (2013).
Renkvist et al., "A listing of human tumor antigens recognized by T cells", Cancer Immunol. Immunother., 2001, vol. 50, p. 3-15.

(Continued)

*Primary Examiner* — Laura B Goddard
(74) *Attorney, Agent, or Firm* — Wenderoth, Lind & Ponack, L.L.P.

(57) ABSTRACT

The present invention relates to a method of treating or preventing melanoma using vaccination or immunisation, wherein said vaccination or immunisation involves the use of a photosensitizing agent, a melanoma antigen (i.e. an antigenic molecule), for example a vaccine component, and irradiation with light of a wavelength effective to activate the photosensitizing agent. The invention also relates to said photosensitizing agent and melanoma antigen for use in such a method, and to cells produced by the method.

38 Claims, 24 Drawing Sheets

Specification includes a Sequence Listing.

(56) References Cited

OTHER PUBLICATIONS

Hodi et al., "Well-Defined Melanoma Antigens as Progression Markers for Melanoma: Insights into Differential Expression and Host Response Based on Stage", Clin. Cancer Res., 2006, vol. 12, p. 673-678.
Vaishampayan el al., "Active Immunotherapy of Metastatic Melanoma with Allogeneic Melanoma Lysates and Interferon α", Clin. Cancer Res., 2002, vol. 8, p. 3696-3701.
Baars et al., "Skin tests predict survival after autologous tumor cell vaccination in metastatic melanoma: Experience in 81 patients", Ann. Oncol., 2000, vol. 11, p. 965-970.
Steinhagen et al., "TLR-Based Immune Adjuvants", Vaccine, 2011, vol. 29(17), p. 3341-3355.
Wesch et al., "Modulation of γδ T cell responses by TLR ligands", Cell. Mol. Life Sci., 2011, vol. 68, p. 2357-2370.
Weck et al., "TLR ligands differentially affect uptake and presentation of cellular antigens", Blood, 2007, vol. 109(9), p. 3890-3894.
Blasius A.L. & B. Beutler, "Intracellular Toll-like Receptors", Immunity, 2010, vol. 32, p. 305-315.

\* cited by examiner

A)

D0 — OT-1, i.v.
D1 —┬─ Bleeding,
    │  Immunisation ± TPCS2a, i.v.
D1-3 ─┼─ Light (435nm, 1-12min)
    │
D7 ─┼─ Bleeding (FACS)
    │
    ▼
D14 ── Euthanisia (spleen cultures,
       FACS & ELISA)

B)

A

B

C

A

B

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial sequence
<220> FEATURE:
<223> OTHER INFORMATION: antigen epitope

<400> SEQUENCE: 1

Ser Ile Ile Asn Phe Glu Lys Leu
1               5

<210> SEQ ID NO 2
<211> LENGTH: 22
<212> TYPE: DNA
<213> ORGANISM: Artificial sequence
<220> FEATURE:
<223> OTHER INFORMATION: ODN2395

<400> SEQUENCE: 2
tcgtcgtttt cggcgcgcgc cg                                              22

<210> SEQ ID NO 3
<211> LENGTH: 20
<212> TYPE: DNA
<213> ORGANISM: Artificial sequence
<220> FEATURE:
```

```
<223> OTHER INFORMATION: ODN1826

<400> SEQUENCE: 3
tccatgacgt tcctgacgtt                                           20

<210> SEQ ID NO 4
<211> LENGTH: 9
<212> TYPE: PRT
<213> ORGANISM: Artificial sequence
<220> FEATURE:
<223> OTHER INFORMATION: TRP-2 peptide

<400> SEQUENCE: 4

Ser Val Tyr Asp Phe Phe Val Trp Leu
1               5

<210> SEQ ID NO 5
<211> LENGTH: 9
<212> TYPE: PRT
<213> ORGANISM: Artificial sequence
<220> FEATURE:
<223> OTHER INFORMATION: gp100 peptide

<400> SEQUENCE: 5

Lys Val Pro Arg Asn Gln Asp Trp Leu
1               5
```

TREATMENT OR PREVENTION OF MELANOMA USING PHOTOCHEMICAL INTERNALIZATION OF A MELANOMA ANTIGEN

The present invention relates to a method of treating or preventing melanoma using vaccination or immunisation, wherein said vaccination or immunisation involves the use of a photosensitizing agent, a melanoma antigen (i.e. an antigenic molecule), for example a vaccine component, and irradiation with light of a wavelength effective to activate the photosensitizing agent. The invention also relates to said photosensitizing agent and melanoma antigen for use in such a method, and to cells produced by the method.

Melanoma is a malignant tumour of melanocytes, which are the cells responsible for producing melanin, the dark pigment responsible for skin colour. These cells occur predominantly in the skin, but are also found in other parts of the body, including the bowel and the eye. Melanoma can originate in any part of the body that contains melanocytes.

The primary cause of melanoma is ultraviolet light (UV) exposure, as UV light can cause damaging mutations to cellular nucleic acids. Whilst melanoma is less common than other skin cancers, it is much more serious if not detected in the early stages, and causes the majority (approximately 75%) of skin cancer-related deaths. There are approximately 160,000 new cases of melanoma each year, and about 48,000 melanoma-related deaths occur worldwide per year. It is particularly common among Caucasians, especially northern Europeans and northwestern Europeans living in sunny climates. There are higher rates in Oceania, North America, Europe, Southern Africa and Latin America, with low rates in southern Italy and Sicily. This geographic pattern reflects UV light exposure crossed with the amount of skin pigmentation in the population.

In addition to UV light exposure, melanoma can also have a genetic component, and a number of rare mutations, which often run in families, are known to greatly increase susceptibility to melanoma. Some rare genes have a relatively high risk of causing melanoma; some more common genes, such as MC1R (that causes red hair), have a relatively lower elevated risk. Genetic testing can be used to determine whether a person has one of the currently known mutations and hence a propensity to develop melanoma.

Treatment of melanoma includes surgical removal of the tumour. If melanoma is found early, while it is still small and thin, and if it is completely removed, then the chance of cure is high. The likelihood that the melanoma will come back or spread depends on how deeply it has penetrated the layers of the skin. For melanomas that return or spread, treatments include chemo- and immunotherapy, or radiation therapy.

However, whilst these treatment options are currently available, there remains a need for alternative, improved and safer ways of preventing and treating melanoma, as melanoma can be very resistant to chemotherapeutics and targeted drug therapies. The present invention addresses this need. As demonstrated in the present Examples, in a mouse model of melanoma, mice were immunised with an antigen expressed by the melanoma cells and a photosensitiser, which was activated by subsequent light treatment of the mice. The stimulation of CD8 T cells with suppressive effects on the growth of a melanoma was demonstrated both when the mice were vaccinated prior to challenge with tumour cells, and in mice who had pre-existing melanoma.

Thus, the present invention is based on vaccination or immunisation of a subject with a melanoma antigen. The vaccination can be prophylactic, i.e. administered prior to development of melanoma to prevent melanoma. Surprisingly, it was found that the vaccination can also be therapeutic, i.e. wherein the vaccination supresses an existing melanoma. As demonstrated in Example 1, the present invention can also reduce the metastatic potential of melanoma.

Vaccination involves administration of antigenic molecules to provoke the immune system to stimulate development of an immune response to the antigenic molecule.

Since most vaccines are taken up by antigen presenting cells through endocytosis and transported via endosomes to lysosomes for antigen digestion and presentation via the MHC class-II pathway, vaccination primarily activates CD4 T-helper cells and B cells. To combat disorders or diseases such as cancer, e.g. melanoma according to the present invention, the stimulation of cytotoxic CD8 T-cell responses is important. However, the induction of cytotoxic CD8 T cells usually fails due to the difficulty in delivering antigen to the cytosol and to the MHC class-I pathway of antigen presentation.

Therapeutic vaccination, e.g. to suppress an existing melanoma, is challenging because of the usual immunological non-reactivity towards tumour cells. Stimulation of tumour-specific CD8 T cells has been tested with peptide vaccines or autologous dendritic cells treated ex vivo with melanoma antigens. However, such vaccination strategies have failed because of inappropriate antigen processing. The present invention unexpectedly has a utility in therapeutic vaccination of melanoma.

Photochemical internalisation (PCI) improves delivery of molecules into the cytosol. PCI is a technique which uses a photosensitizing agent, in combination with an irradiation step to activate that agent, and is known to achieve release of molecules co-administered to a cell into the cell's cytosol. This technique allows molecules that are taken up by the cell into organelles, such as endosomes, to be released from these organelles into the cytosol, following irradiation. PCI provides a mechanism for introducing otherwise membrane-impermeable (or poorly permeable) molecules into the cytosol of a cell in a manner which does not result in widespread cell destruction or cell death.

The basic method of photochemical internalisation (PCI), is described in WO 96/07432 and WO 00/54802, which are incorporated herein by reference. In such methods, the molecule to be internalised (which in the present invention would be the antigenic molecule, i.e. the melanoma antigen), and a photosensitizing agent are brought into contact with a cell. The photosensitizing agent and the molecule to be internalised are taken up into a cellular membrane-bound subcompartment within the cell, i.e. they are endocytosed into an intracellular vesicle (e.g. a lysosome or endosome). On exposure of the cell to light of the appropriate wavelength, the photosensitizing agent is activated which directly or indirectly generates reactive species which disrupt the intracellular vesicle's membranes. This allows the internalized molecule to be released into the cytosol.

It was found that in such a method the functionality or the viability of the majority of the cells was not deleteriously affected. Thus, the utility of such a method, termed "photochemical internalisation" was proposed for transporting a variety of different molecules, including therapeutic agents, into the cytosol i.e. into the interior of a cell.

WO 00/54802 utilises such a general method to present or express transfer molecules on a cell surface. Thus, following transport and release of a molecule into the cell cytosol, it (or a part of that molecule) may be transported to the surface of the cell where it may be presented on the outside of the cell i.e. on the cell surface. Such a method has particular utility in the field of vaccination, where vaccine components i.e. antigens or immunogens, may be introduced to a cell for presentation on the surface of that cell, in order to induce, facilitate or augment an immune response.

The present inventors have found that a PCI-based method of immunisation/vaccination using a melanoma antigen results in improved vaccination or an improved immune response against melanoma, and hence improved prevention or treatment of melanoma.

As will be described in more detail in the Examples below, it has been demonstrated that the method of the invention results in improved vaccination or an improved immune response against melanoma, which leads to a reduction in melanoma development or melanoma tumour size, and also a decrease in melanoma metastasis. For example, Example 1 and FIG. 1D demonstrate that in vivo vaccination of mice using a melanoma antigen and a photosensitiser and irradiation with light of a wavelength effective to activate the photosensitiser led to a significantly increased survival of said mice compared to unvaccinated mice when subject to administration of melanoma cells, i.e. prophylactic vaccination was achieved. Nine out of ten vaccinated mice did not develop tumours, whilst fifty percent of mice vaccinated only with the antigen and not with concomitant PCI developed tumours. As demonstrated in Example 1 and FIG. 2B, therapeutic vaccination with PCI-based vaccines improves survival in melanoma-bearing mice. Metastasis was also reduced in vaccinated mice (see FIG. 4).

Whilst not wishing to be bound by theory, it is believed that the methods of the invention result in increased antigen presentation on MHC Class I molecules leading to an increased CD8+ T cell responses and hence improved vaccination methods. As discussed below, some of the present Examples utilise a model system of OT-1 cells, which is used for assessing MHC class I presentation (see e.g. Delamarre et al., J. Exp. Med. 198:111-122, 2003). In this model system MHC class I presentation of the antigen epitope SIINFEKL leads to activation of the OT-1 T-cells, and the activation can be measured as an increase in proliferation of the antigen-specific T-cells or increased production of IFNγ or IL-2. The results show increased numbers of antigen-specific T cells, and increased IL-2 and IFNγ production by the T cells, which is correlated with increased or improved antigen presentation.

Thus, in a first aspect the present invention provides a method of expressing a melanoma antigen or a part thereof on the surface of a cell, comprising contacting said cell with said melanoma antigen and a photosensitizing agent and irradiating the cell with light of a wavelength effective to activate the photosensitising agent, wherein said melanoma antigen or a part thereof is released into the cytosol of the cell and subsequently presented on the cell's surface. The method may be conducted in vitro or in vivo. In the latter case said cell is in a subject.

The invention also extends to a cell or population of cells obtainable by the method. Such cells contain or express the melanoma antigen, or a part thereof, on their surface. Compositions of the present invention (e.g. pharmaceutical compositions) may also comprise said cell or cell population (containing a melanoma antigen which has been internalised into the cytosol of said cell by a method of the invention). The invention further extends to such compositions for use in therapy or prophylaxis, particularly for treating or preventing melanoma.

A further aspect of the invention provides a composition (e.g. a pharmaceutical composition) comprising a photosensitising agent, and a melanoma antigen, optionally separately, e.g. in separate containers or comprising a cell of the invention. When said composition is a pharmaceutical composition it contains one or more pharmaceutically acceptable diluents or excipients.

In a further aspect the composition is for use in expressing a melanoma antigen (or a part thereof) on the surface of a cell and the invention extends to use of the composition to express said melanoma antigen, or a part thereof, on the surface of a cell.

The invention extends in particular to therapeutic methods and thus provides a method of generating an immune response in a subject, comprising administering to said subject a melanoma antigen and a photosensitising agent (or a composition comprising the same) and irradiating with light of a wavelength effective to activate said photosensitising agent, wherein an immune response is generated.

The invention also extends to a method of generating an immune response in a subject comprising administering to said subject a cell or population of cells (or a composition comprising the same) of the invention. Such methods may include the step of preparing a cell or population of cells according to methods of the invention.

Preferably said method is a method of vaccination, preferably for treating or preventing melanoma.

Alternatively expressed, the invention provides a melanoma antigen and photosensitising agent for use in expressing said melanoma antigen or a part thereof on the surface of a cell. Also provided is said melanoma antigen and photosensitising agent or a cell or cell population of the invention for use in prophylaxis or therapy, and/or for stimulating an immune response (for example as described above). Compositions of the invention may be similarly employed.

The invention further extends to the use of the melanoma antigen and/or photosensitising agent or cell or cell population of the invention in the manufacture of a medicament for stimulating an immune response, in particular for vaccination and/or for treating or preventing melanoma.

The present invention also provides a kit or product comprising a photosensitising agent and a melanoma antigen. Preferably said kit (or product) is for simultaneous, separate or sequential use in a method described herein, preferably for stimulating an immune response, preferably for vaccination purposes, preferably for treating or preventing melanoma.

The compounds, cells and methods of the invention may be used in vitro or in vivo, for example either for in situ treatment or for ex vivo treatment followed by the administration of the treated cells to the body.

In such methods said melanoma antigen and said photosensitizing agent are each taken up into an intracellular vesicle; and when the cell is irradiated the membrane of the intracellular vesicle is disrupted releasing the melanoma antigen into the cytosol of the cell.

The agents may be taken up into the same or a different intracellular vesicle relative to each other. It has been found that active species produced by photosensitizers may extend beyond the vesicle in which they are contained and/or that vesicles may coalesce allowing the contents of a vesicle to be released by coalescing with a disrupted vesicle. As referred to herein "taken up" signifies that the molecule taken up is wholly contained within the vesicle. The intracellular vesicle is bounded by membranes and may be any such vesicle resulting after endocytosis, e.g. an endosome or lysosome.

As used herein, a "disrupted" compartment refers to destruction of the integrity of the membrane of that compartment either permanently or temporarily, sufficient to allow release of the antigenic molecule contained within it.

A "photosensitizing agent" as referred to herein is a compound that is capable of translating the energy of absorbed light into chemical reactions when the agent is activated on illumination at an appropriate wavelength and intensity to generate an activated species. The highly reactive end products of these processes can result in cyto- and vascular toxicity. Conveniently such a photosensitizing agent may be one which localises to intracellular compartments, particularly endosomes or lysosomes.

Photosensitisers may exert their effects by a variety of mechanisms, directly or indirectly. Thus for example, certain photosensitisers become directly toxic when activated by light, whereas others act to generate toxic species, e.g. oxidising agents such as singlet oxygen or other reactive oxygen species, which are extremely destructive to cellular material and biomolecules such as lipids, proteins and nucleic acids.

A range of such photosensitizing agents are known in the art and are described in the literature, including in WO96/07432, which is incorporated herein by reference, and may be used in methods of the invention. There are many known photosensitising agents, including porphyrins, phthalocyanines and chlorins, (Berg et al., J. Photochemistry and Photobiology, 65, 403-409, 1997). Other photosensitising agents include bacteriochlorins.

Porphyrins are the most extensively studied photosensitising agents. Their molecular structure includes four pyrrole rings linked together via methine bridges. They are natural compounds which are often capable of forming metal-complexes. For example in the case of the oxygen transport protein hemoglobin, an iron atom is introduced into the porphyrin core of heme B.

Chlorins are large heterocyclic aromatic rings consisting, at the core, of three pyrroles and one pyrroline coupled through four methine linkages. Unlike porphyrin, a chlorin is therefore largely aromatic, but not aromatic through the entire circumference of the ring.

Particularly preferred are photosensitizing agents which locate to endosomes or lysosomes of cells. Thus, the photosensitizing agent is preferably an agent which is taken up into the internal compartments of lysosomes or endosomes. Preferably the photosensitizing agent is taken up into intracellular compartments by endocytosis. Preferred photosensitizing agents are amphiphilic photosensitizers (e.g. disulphonated photosensitisers) such as amphiphilic phthalocyanines, porphyrins, chlorins, and/or bacteriochlorins, and in particular include sulfonated (preferably disulfonated) meso-tetraphenyl chlorins, porphyrins, phthalocyanines and bacteriochlorins. Particularly preferred are $TPPS_{2a}$ (tetraphenylporphine disulfonate), $AlPcS_{2a}$ (aluminium phthalocyanine disulfonate), $TPCS_{2a}$ (tetraphenyl chlorin disulfonate) and $TPBS_{2a}$ (tetraphenyl bacteriochlorin disulfonate), or pharmaceutically acceptable salts thereof. Preferably the photosensitizing agent is $TPCS_{2a}$ (Disulfonated tetraphenyl chlorin, e.g. Amphinex®).

Optionally, one or other or both of the photosensitizing agent and the melanoma antigen may be attached to or associated with or conjugated to one or more carrier molecules or targeting molecules which can act to facilitate or increase the uptake of the photosensitizer agent or melanoma antigen or can act to target or deliver these entities to a particular cell type, tissue or intracellular compartment.

Examples of carrier systems include polylysine or other polycations, polymeric carriers, for example based on dextran (e.g. dextran sulphate), chitosans or poly(lactic-co-glycolic acid) (PLGA), different cationic lipids, liposomes, including sterically stabilised liposomes or reconstituted LDL-particles. These carrier systems can generally improve the pharmacokinetics and increase the cellular uptake of the melanoma antigen and/or the photosensitizing agent and may also direct the melanoma antigen and/or the photosensitizing agent to intracellular compartments that are especially beneficial for obtaining photochemical internalisation, but they do not generally have the ability to target the melanoma antigen and/or the photosensitizing agent to specific cells (e.g. cancer cells) or tissues. However, to achieve such specific or selective targeting the carrier molecule, the melanoma antigen and/or the photosensitizer may be associated or conjugated to specific targeting molecules that will promote the specific cellular uptake of the melanoma antigen into desired cells or tissues. Such targeting molecules may also direct the melanoma antigen to intracellular compartments that are especially beneficial for obtaining photochemical internalization.

Many different targeting molecules can be employed, e.g. as described in Caminschi et al., Frontiers in Immunology 3, 1-13, 2012). The carrier molecule and/or the targeting molecule may be associated, bound or conjugated to the melanoma antigen, to the photosensitizing agent or both, and the same or different carrier or targeting molecules may be used. As mentioned above, more than one carrier and/or targeting molecule may be used simultaneously.

Preferred carriers for use in the present invention include polycations such as polylysine (e.g. poly-L-lysine or poly-D-lysine), polyethyleneimine or dendrimers (e.g. cationic dendrimers such as SuperFect7); cationic lipids such as DOTAP or Lipofectin, peptides and polymeric carriers e.g. based on dextran, chitosans or poly(lactic-co-glycolic acid) (PLGA).

Thus the photosensitising agent may be linked to a carrier. For example, the photosensitising agent may be provided in the form of a conjugate, e.g. a chitosan-based conjugate, for example a conjugates disclosed in WO2013/189663, which is hereby incorporated by reference. For example, the conjugate of a photosensitiser and chitosan may be of Formula (I):

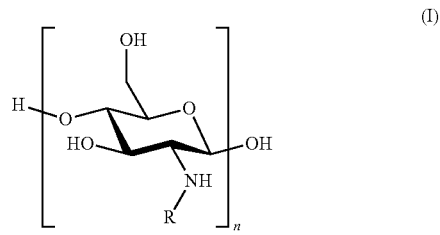

wherein
n is an integer greater than or equal to 3,
R appears n times in said compound and
in 0.5%-99.5% of said total Rn groups, each R is a group A selected from:

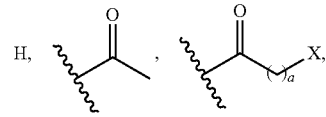

wherein a is 1, 2, 3, 4 or 5; and X is Br, Cl or OH;

![structure]

wherein each $R_1$, which may be the same or different, is selected from H, $CH_3$ and —$(CH_2)_c$—$CH_3$; b is 1, 2, 3, 4 or 5; and c is 0, 1, 2, 3, 4 or 5;

![structure]

wherein Y is O; S; $SO_2$; —$NCH_3$; or —$N(CH_2)_e CH_3$; d=1, 2, 3, 4 or 5; and e=1, 2, 3, 4 or 5;

![structure]

wherein $R_2$ is —$(CH_2)_h$—$CH_3$ or —CO—$(CH_2)_h$—$CH_3$; f is 1, 2, 3, 4 or 5; g is 1, 2, 3, 4 or 5; and h is 0, 1, 2, 3, 4 or 5;

![structure]

wherein $R_3$ is —$(CH_2)_j$—$CH_3$, i is an integer from 1 to 200, preferably from 1-10; j is 0, 1, 2, 3, 4 or 5; and k is 1, 2, 3, 4 or 5;

![structure]

wherein $R_3$ is —$(CH_2)_j$—$CH_3$, i is an integer from 1 to 200, preferably from 1-10; and j is 0, 1, 2, 3, 4 or 5;

![structure]

wherein $R_3$ is —$(CH_2)_j$—$CH_3$, i is an integer from 1 to 200, preferably from 1-10; j is 0, 1, 2, 3, 4 or 5; and each $R_1$, which may be the same or different, is selected from H, $CH_3$ and —$(CH_2)_c$—$CH_3$; and c is 0, 1, 2, 3, 4 or 5;

![structure]

wherein $R_3$=—$(CH_2)_j$—$CH_3$, i is an integer from 1 to 200, preferably from 1-10; and j is 0, 1, 2, 3, 4 or 5;

![structure]

wherein $R_3$=—$(CH_2)_j$—$CH_3$, i is an integer from 1 to 200, preferably from 1-10; L is 1, 2, 3, 4, 5, 6, 7, 8, 9 or 10; and j is 0, 1, 2, 3, 4 or 5;

![structure]

![structure]

wherein m is 1, 2, 3, 4 or 5;
wherein each R group may be the same or different; and in 0.5%-99.5% of said total Rn groups, each R is a group B selected from:

![structures]

-continued
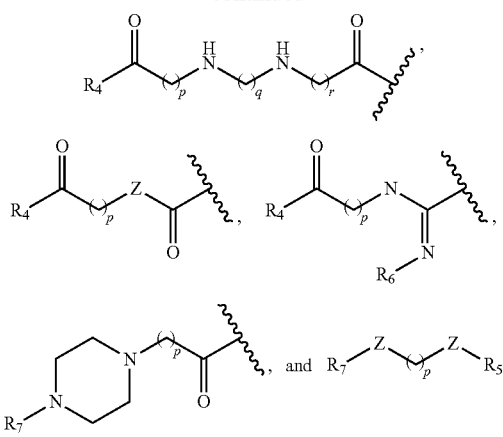
wherein
p is 0, 1, 2, 3, 4 or 5; q is 1, 2, 3, 4 or 5; and r is 1, 2, 3, 4 or 5;
$R_4$ is a group selected from:
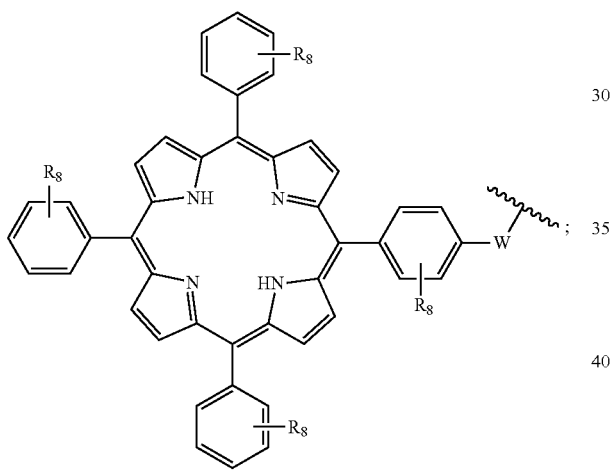
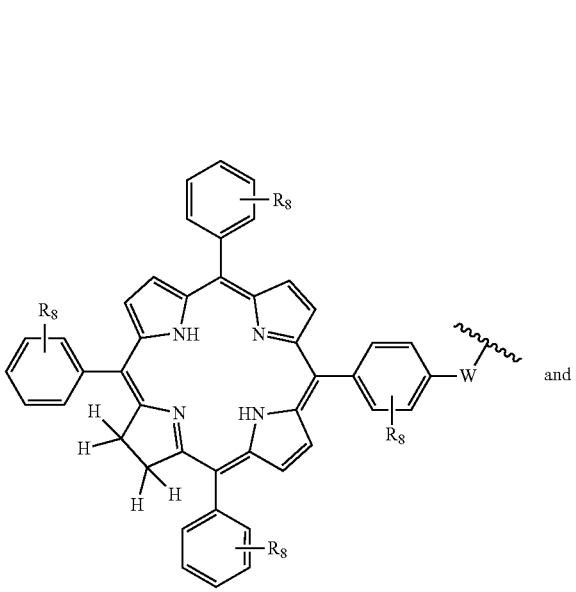
-continued
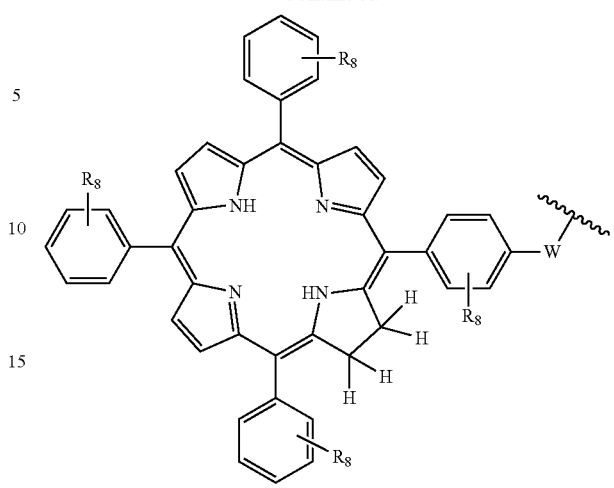
W is a group selected from O, S, NH or $N(CH_3)$;
$R_5$ is a group selected from: $-(CH_2)_s-CO-$; $-(CH_2)_s-Z-(CH_2)_t-CO-$ and $-(CH_2)_s-Z-(CH_2)_t-Z-CO-$; wherein s is 0, 1, 2, 3, 4 or 5; t is 0, 1, 2, 3, 4 or 5;
Z is NH, O, S, or $SO_2$;
$R_6$ is a group selected from $-CN$ and $CH_3$;
$R_7$ is a group selected from:
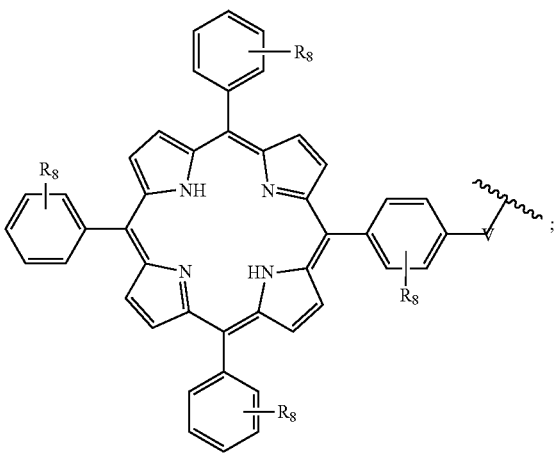
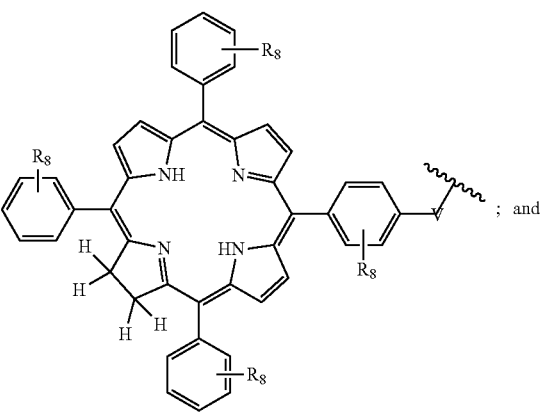

-continued

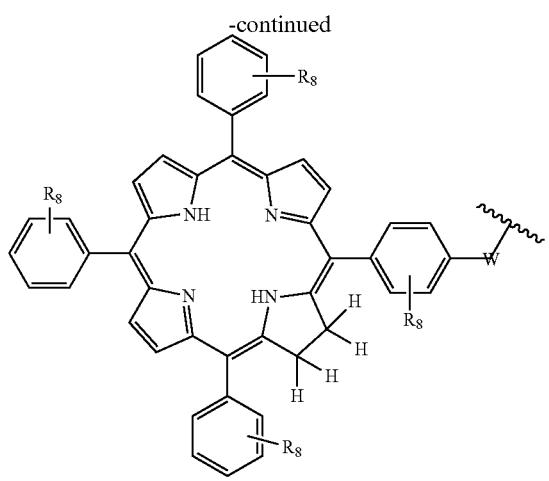

V is a group selected from CO, SO$_2$, PO, PO$_2$H or CH$_2$; and

R$_8$ is a group (substituted in the o, m or p position), which may be the same or different, selected from H, —OH, —OCH$_3$, —CH$_3$, —COCH$_3$, C(CH$_3$)$_4$, —NH$_2$, —NHCH$_3$, —N(CH$_3$)$_2$ and —NCOCH$_3$;

wherein each R group may be the same or different. Preferred conjugates are as described in WO2013/189663.

Preferred A R groups are:

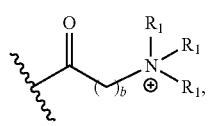

wherein preferably each R$_1$ is CH$_3$ and b is 1; and

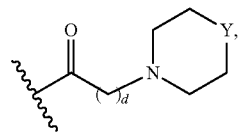

wherein preferably Y is —NCH$_3$ and d is 1.

Preferred B R groups are:

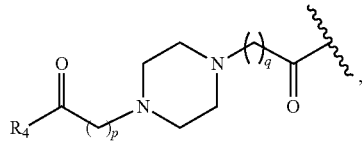

wherein preferably p is 1 and q is 1; and

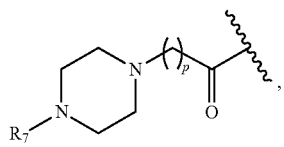

wherein preferably p is 1.

Preferably R$_4$ is selected from:

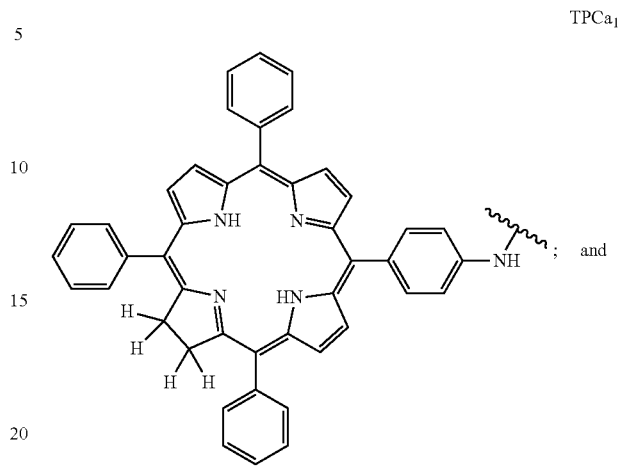

TPCa$_1$

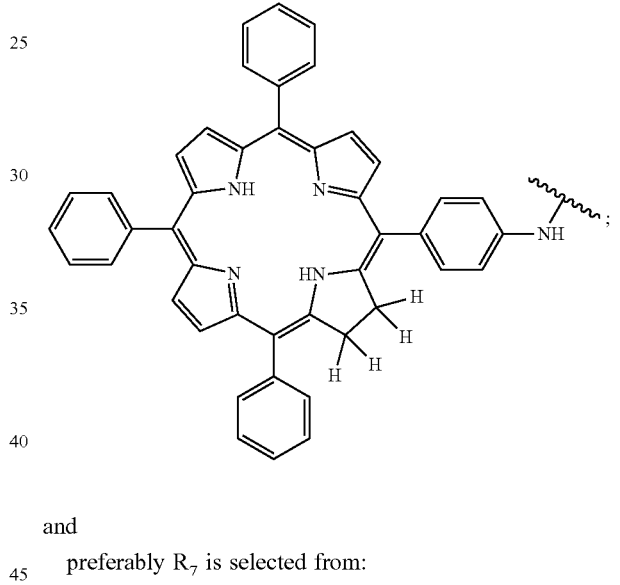

TPCa$_2$ and preferably R$_7$ is selected from:

TPCc$_1$

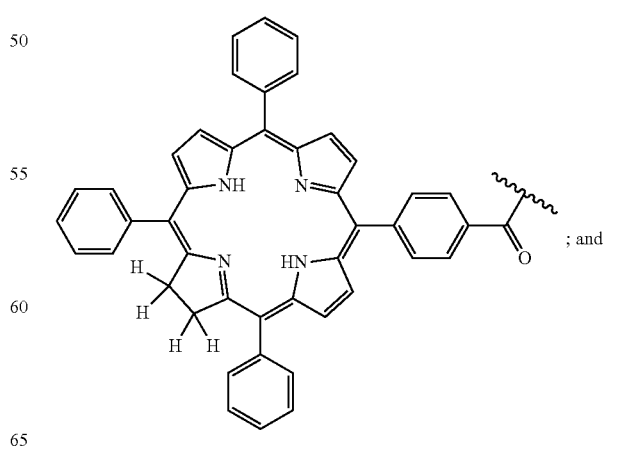

; and

TPCc₂

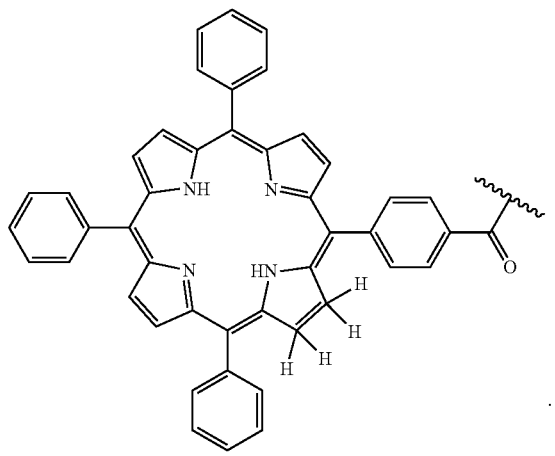

Particularly preferred conjugates are:

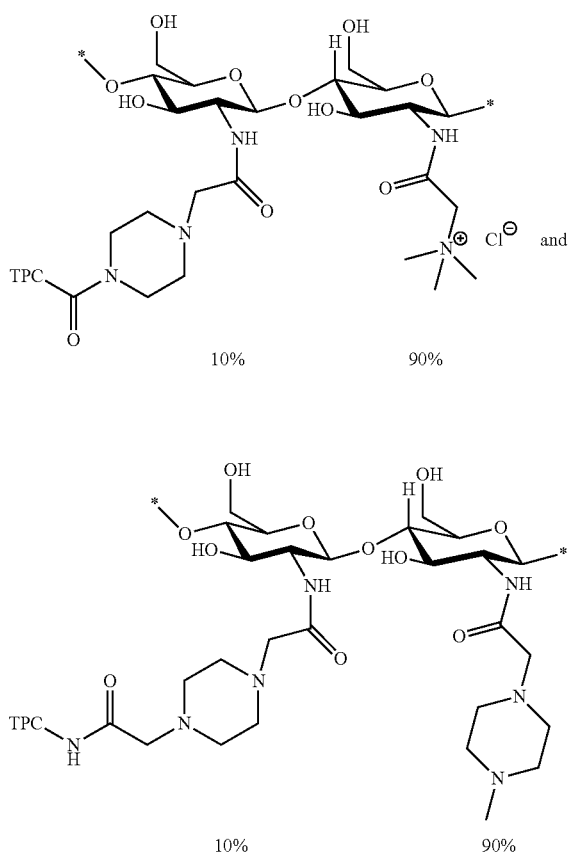

(wherein

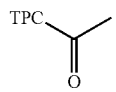

is R₇ and

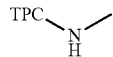

is R₄ having the preferred form defined above, e.g. TPCa₁, TPCa₂, TPCc₁ or TPCc₂).

"Melanoma" as referred to herein includes all types of melanoma, including for example superficial spreading melanoma, nodular melanoma, lentigo maligna melanoma, desmoplastic melanoma, acral lentiginous melanoma and amelanotic melanoma, polypoid melanoma, melanoma with small nevus-like cells and melanoma with features of a Spitz nevus.

Whilst the majority of melanomas occur cutaneously (cutaneous malignant melanoma), melanoma can also occur elsewhere in the body, for example in the internal organs, e.g. in the mucosal membranes. Clear cell sarcoma is a malignant melanoma of the soft tissues. Melanoma can also occur in the eye (uveal melanoma), vulva, vagina or rectum. These melanomas are also included in the scope of the invention. Preferably the melanomas to be treated are skin melanomas. Melanoma also extends to metastatic melanoma, i.e. cells that have originated from a primary melanoma but which have metastasised to a different location to yield secondary tumours. Treatment or prevention of melanoma as described herein extends to treatment of primary melanomas and/or secondary tumours deriving from the primary melanoma. As such, the invention also has particular utility in treating metastatic melanoma.

A "melanoma antigen" as referred to herein is a molecule derived from a melanoma cell which itself, or a part thereof, is capable of stimulating an immune response, when presented to the immune system or immune cells in an appropriate manner. As referred to herein, a molecule "derived" from a melanoma is a molecule which may appear in the melanoma cell or which is modified relative to the native molecule in the melanoma, e.g. by truncation, post-expression modification and/or sequence modification providing the modified molecule retains one or more epitopes from the native molecule which allows the modified molecule to generate an immune response which would recognise the native molecule. The melanoma antigen may be obtained by isolation from appropriate sources e.g. the subject's melanoma or may be synthesised e.g. by chemical synthesis or peptide/protein expression.

The melanoma antigen constitutes the "antigenic molecule" of the vaccine, and is also referred to herein as the antigenic molecule. Advantageously, therefore the antigenic molecule will be a vaccine antigen or vaccine component, such as a polypeptide containing entity.

Whilst traditionally the antigenic components of vaccines have comprised whole cells, in addition sub-unit vaccines, i.e. vaccines based on particular antigenic components e.g. proteins or peptides, or even carbohydrates, have been widely investigated and reported in the literature. Any such "sub-unit"-based vaccine component may be used as the antigenic molecule of the present invention. Alternatively, cells containing one or more antigenic molecules may be used.

There are several alternative options for the melanoma antigen which are encompassed by the present invention. The "melanoma antigen" can include one or more different antigens.

For example, in one aspect, the melanoma antigen is a melanoma protein or peptide, for example an antigenic peptide or T-cell epitope, for example one or more selected from gp100, Melan-A, tyrosinase, MAGE-1, MAGE-3 and tyrosinase related protein-2 (TRP-2) or a peptide epitope thereof. Details of these and further suitable melanoma antigens are disclosed in Renkvist et al., Cancer Immunol. Immunother. 50:3-15, 2001 (and references therein), and Hodi, Clin. Cancer. Res. 12:673-678, 2006, which are hereby incorporated by reference. In particular, gp100, Melan-2, tyrosinase, MAGE-1, MAGE-3 and TRP-2 and their peptide epitopes are as described in Renkvist et al., supra. Thus the invention extends to use of gp100, Melan-2, tyrosinase, MAGE-1, MAGE-3 or TRP-2, or an antigen comprising or consisting of their disclosed peptide epitopes, as disclosed in Renkvist et al., supra or a sequence with at least 95% sequence identity thereto (over a relevant window of comparison) using standard comparison techniques known in the art. In a preferred embodiment the invention extends to use of TRP-2. The sequence of human TRP-2 can be found as described above and under UniProt Accession no. P40126.

Peptide antigens, for example up to at least 200 amino acids, may be obtained from companies performing custom peptide synthesis, e.g. United BioSystems Inc (formerly United Peptide Corp., Herndon, Va., USA).

Proteins may be synthesised as recombinant proteins according to methods known in the art, or may be provided by, for example, Abcam (Cambridge, Mass., USA) or by MyBioSource, Inc. (San Diego, Calif., USA).

In an alternative aspect, the melanoma antigen is derived from one or more melanoma cell lines, such as A2058, A375, C32, COLO829, G361, HT144, HTB65, RPMI7951, SKMEL2, SRS3, SW691UACC3074, WM15, WM239A, WM266-4, WM35, WM278, WM1552C, WM9, WM1799, WM1232, WM1158, WM1193-C, WM873-1, EM873-2, WM75, WM1727A, WM88, WM47, WM983A, WM983B, WM164, 451Lu, WM373, WM858, WM853-2, WM4002F, WM1366, WM3066, WM3623, WM852, WM3451, WM115, WM266, WM1341D, WM3629, WM3670, WM3130, RL159, WM793, 1205LU, WM1791C, WM46, WM39, WM3681, WM3928F, WM3912, WM209, WM8, WM3438, WM3918, C8161, MUM2C, UACC1227, UACC2565, UACC457, UACC827, UACC903, or UACC929. The melanoma antigen may also be derived from the cell line B16-F10. The antigen may be derived from a melanoma metastases, for example, IF6, MV3, BLM, BRO, M14, or 530.

In one embodiment the melanoma antigen may be an extract from one or more cells from one or more different melanoma cell lines as defined above. The method according to the invention may include the preparation of melanoma antigens (or an extract containing such melanoma antigens) from melanoma cell line cells. An extract (or melanoma antigens) may be obtained from the cell or cells using methods known in the art (see for example Vaishampayan et al., Clin. Cancer Res. 8, 3696-3701, 2002). The melanoma antigen may also be provided in a cell from one or more different melanoma cell lines as defined above.

In a further alternative aspect, the melanoma antigen is derived (or obtained) from one or more melanoma cells from a subject with melanoma. In this embodiment, a melanoma cell (or cells) is isolated from a patient using known methods, optionally melanoma antigens or an extract containing the same are prepared and said cell, melanoma antigens or extract are administered to the subject (for example see Baars et al., Ann. Oncol. 11, 965-970, 2000) and references therein. Thus, in one aspect of the invention, a method according to the invention includes the preliminary step of removing melanoma tissue from a subject and preparing a solution containing single cells (e.g. by use of collagenase and DNAse). The cells obtained by this method may be used for the preparation of melanoma antigens or an extract containing the same i.e. the method may include the preparation of melanoma antigens or an extract containing the same from melanoma cells obtained from the subject. In one embodiment, melanoma antigens or an extract containing the same (prepared from the subject) may be administered to the patient. Alternatively the cells obtained by the method may be used directly as a composition comprising the antigen. The cells may be autologous i.e. isolated from and administered to the same individual, or syngeneic or allogeneic.

Thus, methods of the invention may additionally include the step of preparing a composition comprising one or more melanoma antigens from a) one or more subjects or b) one or more cell lines. The preparation step may comprise obtaining melanoma cells from said one or more subjects. The preparation step may also include preparing an extract containing said one or more melanoma antigens from the melanoma cells from said one or more subjects or from said one or more cell lines. These steps may be applied to all methods and preferred methods of the invention, e.g. all methods defined in the appended claims. Optionally, the composition may contain substantially purified melanoma antigens, e.g. said melanoma antigen(s) may comprise at least 50, 60, 70, 80 or 90% w/w of said composition. The obtained antigens may be modified, e.g. by post-expression modification, truncation or by the addition of carriers for administration according to known techniques. In particular the antigens may comprise the relevant peptide epitopes of the melanoma antigens found in vivo.

In one embodiment the antigenic molecule according to the invention is a peptide (which is defined herein to include peptides of both shorter and longer lengths i.e. peptides, oligopeptides or polypeptides, and also protein molecules or fragments thereof e.g. peptides of 5-500 e.g. 10 to 250 such as 15 to 75, or 8 to 25 amino acids). In one embodiment the peptide is a synthetic peptide, for example, as disclosed in Rosenberg et al., Nat. Med., 4(3), 321-7, 1998. However, any suitable melanoma peptide vaccine component may be used as the antigenic molecule of the invention. The peptide may thus be synthetic or isolated or otherwise derived from a melanoma cell as discussed above.

In one embodiment an adjuvant is also used in the methods of the invention. For example, the adjuvant may be selected from a Toll-like receptor (TLR) 3 ligand, for example Poly(IC) (e.g. high (e.g. average size of 1.5-8 kb) or low (e.g. average size of 0.2-1 kb) MW Poly(IC)), a TLR4 ligand such as MPLA, a TLR 7/8 ligand, for example resiquimod or imiquimod, and a TLR 9 ligand, for example a CpG oligonucleotide, such as ODN2395 (5'-tcgtcgttttcggcgcgcgccg-3') or ODN1826 (5'-tc-catgacgttcctgacgtt-3'). In a preferred embodiment the adjuvant is Poly(IC). The dose of Poly(IC) may be between 5 μg and 200 μg, for example between 10 μg and 100 μg, preferably 10 μg or 50 μg for mice, which may be appropriately scaled where necessary for treatment of other animals.

Thus, a TLR ligand according to the present invention is a molecule that binds to at least one, or one or more, toll-like receptor (TLR) and results in activation of the TLR, for example activation of TLR-mediated cell signalling.

TLR signalling is divided into two distinct signalling pathways, the MyD88-dependent (TLR7-9) and TRIF-dependent pathway (TLR3). A TLR ligand according to the invention activates one or both of these two pathways.

Standard methods for determining activation of TLR signalling are known in the art, for example determination of the phosphorylation state of appropriate signalling proteins. Alternatively, one may determine whether a ligand acts through a TLR by well known methods in the art, e.g. by genetically deleting the gene encoding the specific TLR and determining whether the effect of the ligand is maintained. This method can be used both in vitro and in vivo in transgenic knock-out mice, which are commercially available (TLR3 knock-outs are available from The Jackson Laboratory and TLR 3, 7 and 9 knock-outs from Oriental-BioService Inc). In addition, HEK-Blue™ cells (Invivogen, San Diego, Calif., USA) are available which are designed to study stimulation of TLRs via assaying NF-κB/AP1 activation. Such cells are available for TLRs 3 and 7-9. Also, TLR antagonists such as those available from Invivogen can be used to determine whether antagonism of the TLR inhibits the action of a putative ligand. Thus, methods of determining whether a molecule is a TLR ligand, e.g. a specific TLR ligand, are well known in the art.

The sequences of TLR receptors are known and binding to those receptors by ligands described herein may be assessed, e.g. as described hereinbefore. By way of example, known TLR 3 and 7-9 amino acid sequences are shown in Table 1 below.

TABLE 1

| TLR | NCBI Reference Sequence | UniProtKB/Swiss-Prot Reference |
|---|---|---|
| toll-like receptor 3 precursor (Homo sapiens) | NP_003256.1 | O15455 |
| toll-like receptor 7 precursor (Homo sapiens) | NP_057646.1 | Q9NYK1 |
| toll-like receptor 8 precursor (Homo sapiens) | NP_619542.1 | Q9NR97 |
| toll-like receptor 9 precursor (Homo sapiens) | NP_059138.1 | Q9NR96 |

In one embodiment of the invention, as discussed above, the melanoma antigen may be attached to, associated with or conjugated to one or more carrier molecules. These include polylysine or other polycations, polymeric carriers, for example based on dextran (e.g. dextran sulphate), chitosans or poly(lactic-co-glycolic acid) (PLGA), different cationic lipids, liposomes, including sterically stabilised liposomes or reconstituted LDL-particles. Preferably the melanoma antigen is formulated in a particle. Melanoma antigens may alternatively be presented in oil-in-water or water-in-oil emulsions.

Once released in the cell cytosol by the photochemical internalisation process, the antigenic molecule may be processed by the antigen-processing machinery of the cell. Thus, the antigenic molecule expressed or presented on the surface of the cell may be a part or fragment of the antigenic molecule which is internalised (endocytosed). A "part" of an antigenic molecule (i.e. the melanoma antigen) which is presented or expressed preferably comprises a part which is generated by antigen-processing machinery within the cell. Parts may, however, be generated by other means which may be achieved through appropriate antigen design (e.g. pH sensitive bonds) or through other cell processing means. Conveniently such parts are of sufficient size to generate an immune response, e.g. in the case of peptides greater than 5, e.g. greater than 10 or 20 amino acids in size.

As used herein "expressing" or "presenting" refers to the presence of the melanoma antigen or a part thereof on the surface of said cell such that at least a portion of that molecule is exposed and accessible to the environment surrounding that cell, preferably such that an immune response may be generated to the presented molecule or part thereof. Expression on the "surface" may be achieved in which the molecule to be expressed is in contact with the cell membrane and/or components which may be present or caused to be present in that membrane.

According to the present invention, the term "cell" is used herein to describe cells that are in vitro or ex vivo, or within a subject or organism, e.g. an in vivo cell. The term "cell" includes all eukaryotic cells (including insect cells and fungal cells). Representative "cells" thus include all types of mammalian and non-mammalian animal cells, plant cells, insect cells, fungal cells and protozoa. Preferably, however, the cells are mammalian, for example cells from cats, dogs, horses, donkeys, sheep, pigs, goats, cows, mice, rats, rabbits, guinea pigs, but most preferably from humans. The cell which is subjected to the methods, uses etc. of the invention may be any cell which is capable of expressing, or presenting on its surface a molecule which is administered or transported into its cytosol.

The cell is conveniently an immune cell i.e. a cell involved in the immune response. However, other cells may also present antigen to the immune system and these also fall within the scope of the invention. The cells according to the present invention are thus advantageously antigen-presenting cells as described hereinafter. The antigen-presenting cell may be involved in any aspect or "arm" of the immune response as defined herein.

The stimulation of cytotoxic cells requires antigens to be presented to the cell to be stimulated in a particular manner by the antigen-presenting cells, for example MHC Class I presentation (e.g. activation of CD8+ cytotoxic T-cells requires MHC-1 antigen presentation). Antibody-producing cells may also be stimulated by presentation of antigen by the antigen-presenting cells.

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface (Yewdell and Bennink, Adv. Immunol. 52: 1-123, 1992). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs.

The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, Immunology Today 17: 131-137, 1996). This is the basis for development of inter alia cancer vaccines. One of the largest practical problems is to introduce sufficient amounts of antigens (or parts of the antigen) into the cytosol. This may be solved according to the present invention.

As mentioned previously, once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the melanoma antigen expressed or presented on the surface of the cell according to the present invention may be a part or fragment of the melanoma antigen which is internalised (endocytosed).

A variety of different cell types can present antigen on their surface, including for example, lymphocytes (both T and B cells), dendritic cells, macrophages etc. Others include for example cancer cells e.g. melanoma cells. These cells are referred to herein as "antigen-presenting cells". "Professional antigen-presenting cells" which are cells of the immune system principally involved in the presentation of antigen to effector cells of the immune system are known in the art and described in the literature and include B lymphocytes, dendritic cells and macrophages. Preferably the cell is a professional antigen-presenting cell.

For antigen presentation by an antigen-presenting cell to a cytotoxic T-cell (CTL) the antigenic molecule needs to enter the cytosol of the antigen-presenting cell (Germain, Cell, 76, 287-299, 1994).

In one embodiment of the invention, the cell is a dendritic cell. Dendritic cells are immune cells forming part of the mammalian immune system. Their main function is to process antigenic material and present it on the surface to other cells of the immune system. Once activated, they migrate to the lymph nodes where they interact with T cells and B cells to initiate the adaptive immune response.

Dendritic cells are derived from hematopoietic bone marrow progenitor cells. These progenitor cells initially transform into immature dendritic cells which are characterized by high endocytic activity and low T-cell activation potential. Once they have come into contact with a presentable antigen, they become activated into mature dendritic cells and begin to migrate to the lymph node. Immature dendritic cells phagocytose pathogens and degrade their proteins into small pieces and upon maturation present those fragments at their cell surface using MHC molecules. Dendritic cells arise from monocytes, i.e. white blood cells which circulate in the body and, depending on the right signal, can differentiate into either dendritic cells or macrophages. The monocytes in turn are formed from stem cells in the bone marrow. Monocyte-derived dendritic cells can be generated in vitro from peripheral blood mononuclear cells (PBMCs). Plating of PBMCs in a tissue culture flask permits adherence of monocytes. Treatment of these monocytes with interleukin 4 (IL-4) and granulocyte-macrophage colony stimulating factor (GM-CSF) leads to differentiation to immature dendritic cells (iDCs) in about a week. Subsequent treatment with tumor necrosis factor (TNF) further differentiates the iDCs into mature dendritic cells.

As used herein "contacting" refers to bringing the cells and the photosensitizing agent and/or the antigenic molecule as defined herein into physical contact with one another under conditions appropriate for internalization into the cells, for example, in an appropriate nutritional medium e.g. at 25-39° C. In one embodiment this may be at a body temperature of 36-38° C.

The cell may be contacted with the photosensitizing agent and antigenic molecule as defined herein sequentially or simultaneously. Preferably, and conveniently the components are contacted with the cell simultaneously and preferably are applied to the cell together as described in more detail hereinafter. The agents may be taken up by the cell into the same or different intracellular compartments (e.g. they may be co-translocated).

The cells are then exposed to light of suitable wavelengths to activate the photosensitizing compound which in turn leads to the disruption of the intracellular compartment membranes.

"Internalisation" as used herein, refers to the intracellular, e.g. cytosolic, delivery of molecules. In the present case "internalisation" may include the step of release of molecules from intracellular/membrane bound compartments into the cytosol of the cells.

As used herein, "cellular uptake" or "translocation" refers to one of the steps of internalisation in which molecules external to the cell membrane are taken into the cell such that they are found interior to the outer lying cell membrane, e.g. by endocytosis or other appropriate uptake mechanisms, for example into or associated with intracellular membrane-restricted compartments, for example the endoplasmic reticulum, Golgi body, lysosomes, endosomes etc.

The step of contacting the cells with the various agents may be carried out in any convenient or desired way as described herein. In the in vivo methods of the present invention the agents can be administered to the cell or subject via methods as described herein, which results in cell contact.

The comments below discuss the application of the agents to the cells separately. As discussed above however, these agents may be applied to cells together, separately or simultaneously. The agents may be contacted or administered sequentially under some circumstances, as described below. For in vivo methods the application may be via direct (i.e. localized) or indirect (i.e. systemic or non-localized) administration as described in more detail hereinbelow.

The photosensitizing agent is brought into contact with the cells at an appropriate concentration for the length of time according to the invention, e.g. 12 to 30 hours, e.g. 14-28, 15-25, 16-20, or 17-19 hours. In one embodiment the length of time of contacting is 18 hours, as, as demonstrated in the Examples (see Example 2), a contact time of 18 hours yields optimal results.

However, the contact time will depend on such factors as the particular photosensitizing agent used and the target cell type and location.

The concentration of the photosensitizing agent is conveniently such that once taken up into the cell, e.g. into, or associated with, one or more of its intracellular compartments and activated by irradiation, one or more cell structures are disrupted e.g. one or more intracellular compartments are lysed or disrupted. The photosensitizing agents as described herein may be used in the range 0.005-20 mg/kg body weight when administered systemically. However, the photosensitizing agent is generally administered locally, for example by intradermal, subcutaneous or intratumoural administration, and in that case the dose may be in the region of 1-5000 µg, for example 5-4500, 10-4000, 15-3000, 20-1500, 22-1000, 25-400, or 100-300 µg. In one embodiment the dose is selected from 100 µg, 150 µg, 200 µg and 250 µg, or about 250 µg, or in an alternative embodiment the dose is 100 µg, or about 100 µg. Preferably the dose is 75-125 µg, e.g. 100 µg. The doses provided are for a human of average weight (i.e. 70 kg).

In a preferred embodiment the photosensitiser is administered locally by intradermal administration. For intradermal injection the photosensitiser dose may be dissolved in 50 µl-1 ml, i.e. the concentration may be in the range of 1-50000 µg/ml. In smaller animals the concentration range may be different and can be adjusted accordingly though when administered locally, little variation in dosing is necessary for different animals.

In an alternative preferred embodiment the photosensitiser is administered locally by intratumoural administration. For intratumoural injection the photosensitiser dose may be dissolved in 100 µl-1 ml, i.e. the concentration may be in the range of 1-50000 µg/ml. In smaller animals the concentration range may be different and can be adjusted accordingly though when administered locally, little variation in dosing is necessary for different animals.

The concentration of melanoma antigen to be used will depend on the antigen which is to be used. For the in vivo use according to the present invention the protein antigen dose may be in the range 0.5 or 1-500 µg, for example 1-250 µg, 10-100 µg or 1-50 µg. For peptide antigens an in vivo dose of 0.1-4000 µg, e.g. 0.1-2000 µg, 0.1-1000 µg or 0.1-500 µg, for example 1-50 µg or 0.1-100 µg, may be employed. In one embodiment the dose is 100 µg or about 100 µg. In an alternative embodiment the dose is 10 µg, or about 10 µg. In a further alternative the dose is 200 µg or about 200 µg. Such doses are appropriate for local administration. An appropriate concentration can be determined depending on the efficiency of uptake of the agent in question into the cells in question and the final concentration it is desired to achieve in the cells.

In most cases the photosensitizing agent and the antigenic molecule as defined herein are administered together, but this may be varied. Thus different times or modes or sites of administration (or contact with the cell) are contemplated for the different components, although in a preferred embodiment the antigenic molecule and photosensitizing agent are administered together, preferably via intradermal administration.

Alternatively, the photosensitising agent may be administered separately from the antigen, for example in a separate formulation. In vivo an appropriate method and time of incubation by which the agents are brought into contact with the target cells will be dependent on factors such as the mode of administration and the type of agents which are used. For example, if the agents are injected into a tumour, tissue or organ which is to be treated/irradiated, the cells near the injection point will come into contact with and hence tend to take up the agents more rapidly than the cells located at a greater distance from the injection point, which are likely to come into contact with the agents at a later time point and lower concentration.

According to the present invention the contact between the cell and the photosensitizing agent and antigenic molecule as defined herein can be in the range of about 1 hour to about 48 hours, for example from about 2 hours to about 40 hours, or from about 6 hours to about 36 hours, e.g. from 12 hours to 30 hours, e.g. 16 hours to 20 hours, for example 18 hours or about 18 hours as this yields optimal results.

Preferably the photosensitizing agent and antigenic molecule are contacted with the cell (or administered to the subject) for the same amount of time. However, some variation is possible, e.g. the photosensitizing agent and the antigenic molecule may be applied sequentially. In one embodiment the time between the administration of the photosensitzing agent and the antigenic molecule is a matter of hours. For example, the photosensitizing agent may be applied 16 to 20 hours, e.g. 18 hours, before illumination, and the antigenic molecule may be applied 1 to 3 hours, e.g. 2 hours before illumination. Thus, the time between the administration of the photosensitzing agent and the antigenic molecule may be in the range of 15 to 23 hours. Alternatively, the time between their administration may be smaller, e.g. from 1 minute to 2 hours or less.

Conveniently, when the method is conducted in vitro, the cells may be placed into photosensitizer/antigen-free medium after the contact with the photosensitizer/antigen and before irradiation, e.g. for 30 minutes to 4 hours, e.g. from 1.5 to 2.5 hours, depending on the timing of the incubation with the photosensitiser and antigenic molecule. For administration of agents described herein in vivo, any mode of administration common or standard in the art may be used, e.g. injection, infusion, topical administration, transdermal administration, both to internal and external body surfaces etc. Tissues can be treated as long as the photosensitiser is taken up by the target cells, and the light can be properly delivered. Preferred modes of administration are intradermal, subcutaneous, topical or intratumoural administration or injection. Preferably administration is by intradermal injection or intratumoural injection. Intratumoural administration has the advantage that photochemical treatment and the delivery of an antigen to the tumour can induce an inflammatory response that will lead to the production of immunostimulating cytokines that can attract immune cells to the tumour and enhance the response to the vaccine antigen.

This approach also has the advantage that the photochemical treatment will almost inevitably lead to the lysis of some of the tumour cells in the illuminated area. This will lead to release of proteins from the tumour cells. These antigens can be taken up by APCs in the tumour (attracted by the PCI vaccination procedure). Thus, the generated immune response will be directed not only to the exogenously added antigen, but also to the antigens released from the tumour cells. Since many of these antigens will be different from the antigen contained in the vaccine, the immune response generated with this mode of administration will be much broader than the immune response induced by intradermal administration. For intratumoural administration it is advantageous to administer the vaccine in an amelanotic lesion since the light penetration in such lesions is better than in heavily pigmented lesions. Thus, in one embodiment, the photosensitising agent and the melanoma antigen are administered intratumourally to an amelanotic lesion. To achieve the desired outcome, e.g. antigen presentation, generation of an immune response or vaccination, the methods or parts thereof may be repeated, e.g. "re-vaccination" may take place. Thus, the method in its entirety may be performed multiple times (e.g. 2, 3 or more times) after an appropriate interval or parts of the method may be repeated, e.g. additional irradiation steps.

For example, the method or part of the method may be performed again a matter of days, e.g. between 5 and 60 days (for example 7, 14, 15, 21, 22, 42 or 51 days), e.g. 7 to 20 days, preferably 14 days, or weeks, e.g. between 1 and 5 weeks (for example, 1, 2, 3 or 4 weeks) after it was first performed. All or part of the method may be repeated multiple times at appropriate intervals of time, e.g. every two weeks or 14 days. In a preferred embodiment the method is repeated at least once. In another embodiment the method is repeated at least twice.

For example, in one embodiment wherein an adjuvant is used in the method (e.g. Poly(I:C)), in the second or subsequent time the method is carried out the melanoma antigen is administered in combination with the photosensitiser and illumination, i.e. the adjuvant is not administered in the second or subsequent time the method is carried out.

In an alternative embodiment, parts of the method of the invention may be carried out prior to the method of the invention being carried out. For example, the method may be carried out one or more times, for example twice, in the absence of adjuvant before the method of the invention is carried out. Alternatively, the method may be carried out one or more times, for example twice, in the absence of photosensitiser and illumination before the method of the invention is carried out. Part of the method may be carried out a matter of days, e.g. 7 or 14 days, or weeks, e.g. 1, 3 or 4 weeks before the method of the invention is carried out. Part of the method may be repeated one or more times at these time intervals before the method of the invention is carried out. Thus, in a preferred aspect, the antigenic molecule is administered (e.g. to the subject) equal to or greater than 2 times (e.g. at the time intervals discussed above), wherein at least the administration of said antigenic molecule is performed in accordance with the method of the invention. "Irradiation" to activate the photosensitising agent refers to the administration of light directly or indirectly as described hereinafter. Thus subjects or cells may be illuminated with a light source for example directly or indirectly, e.g. in vivo when the cells are below the surface of the skin or are in the form of a layer of cells not all of which are directly illuminated, i.e. without the screen of other cells. As discussed above, illumination or irradiation of the cell or subject may occur approximately 12-30 hours after administration of the photosensitizing agent and antigenic molecule as defined herein, e.g.16-20 hours, e.g. 18 hours (e.g. 17.5 to 18.5 hours) after. In those cases in which sequential administration of the agents is contemplated, the timing of the irradiation is timed such that each of the agents has been administered or contacted with the cell for at least the stated time before irradiation. Thus, for example, the photosensitizing agent may be applied at time 0 and the antigenic molecule 2 hours later and these agents may then be incubated in the subject until 20 hours at which point the subject may be irradiated, e.g. irradiation at 18 hours after the start of incubation of the antigenic molecule and 20 hours after the start of incubation of the photosensitizing agent. In this scenario irradiation is performed within 16-20 hours of the start of incubation of the agents.

WO 02/44396 (which is incorporated herein by reference) describes a method in which the order of the steps in the method may be arranged such that for example the photosensitizing agent is contacted with the cells and activated by irradiation before the molecule to be internalised (in this case the melanoma antigen) is brought into contact with the cells. This method takes advantage of the fact that it is not necessary for the molecule to be internalised to be present in the same cellular subcompartment as the photosensitizing agent at the time of irradiation.

Thus in one embodiment, said photosensitizing agent and/or said melanoma antigen as defined herein are applied to the cell together, or separately relative to one another. Irradiation is then performed at a time when at least the melanoma antigen and photosensitizing agent appear in the same intracellular compartment. This is referred to as a "light after" method.

In an alternative embodiment, said method can be performed by contacting said cell with the photosensitizing agent first, followed by contact with the melanoma antigen as defined herein, and irradiation is performed after uptake of the photosensitizing agent into an intracellular compartment, but prior to the cellular uptake of the melanoma antigen into an intracellular compartment containing said photosensitizing agent (e.g. it may be present in a different intracellular compartment at the time of light exposure), preferably prior to cellular uptake into any intracellular compartment, e.g. prior to any cellular uptake. Thus for example the photosensitizing agent may be administered followed by irradiation and then administration of the melanoma antigen. This is the so-called "light before" method and is encompassed in methods of the invention.

The light irradiation step to activate the photosensitising agent may take place according to techniques and procedures well known in the art. The wavelength of light to be used is selected according to the photosensitising agent to be used. Suitable artificial light sources are well known in the art, e.g. using blue (400-475 nm) or red (620-750 nm) wavelength light. For $TPCS_{2a}$, and other disulphonated photosensitisers as described herein, for example a wavelength of between 400 and 500 nm, more preferably between 400 and 450 nm, e.g. from 430-440 nm, and even more preferably approximately 435nm, or 435 nm may be used. Alternatively, chlorins and bacteriochlorins can be activated by red light (e.g. 652 nm and 750 nm, respectively). Where appropriate the photosensitiser, e.g. a porphyrin or chlorin, may be activated by green light (e.g. around 514 nm), for example the KillerRed (Evrogen, Moscow, Russia) photosensitiser may be activated by green light.

Suitable light sources are well known in the art, for example the LumiSource® lamp of PCI Biotech AS. Alternatively, an LED-based illumination device which has an adjustable output power of up to 60 mW and an emission spectra of 430-435 nm may be used. For red light, a suitable source of illumination is the PCI Biotech AS 652 nm laser system SN576003 diode laser, although any suitable red light source may be used.

The time for which the cells are exposed to light in the methods of the present invention may vary. The efficiency of the internalisation of a molecule into the cytosol increases with increased exposure to light to a maximum beyond which cell damage and hence cell death increases.

A preferred length of time for the irradiation step depends on factors such as the target, the photosensitizer, the amount of the photosensitizer accumulated in the target cells or tissue and the overlap between the absorption spectrum of the photosensitizer and the emission spectrum of the light source. Generally, the length of time for the irradiation step is in the order of seconds to minutes or up to several hours, e.g. preferably up to 60 minutes e.g. from 0.25 or 1 to 30 minutes, e.g. from 0.5 to 3 minutes or from 1 to 5 minutes or from 1 to 15 minutes e.g. from 3 to 12 minutes, and preferably approximately 3 minutes, e.g. 2.5 to 3.5 minutes or 6 minutes, e.g. 5.5 to 6.5 minutes, or 12 minutes e.g. 11.5 to 12.5 minutes. Shorter irradiation times may also be used, for example 1 to 60 seconds, e.g. 10-50, 20-40 or 25-35 seconds.

Appropriate light doses can be selected by a person skilled in the art and again will depend on the photosensitizer used and the amount of photosensitizer accumulated in the target cells or tissues. The light doses are usually lower when photosensitizers with higher extinction coefficients (e.g. in the red area, or blue area if blue light is used, depending on the photosensitiser used) of the visible spectrum are used. For example, a light dose in the range of 0.24-7.2J/cm$^2$ at a fluence range of 0.05-20 mW/cm$^2$, e.g. 2.0 mW/cm$^2$, may be used when an LED-based illumination device which has an adjustable output power of up to 60mW and an emission spectra of 430-435nm is employed. Alternatively, e.g. if the LumiSource® lamp is employed, a light dose in the range of 0.1-6J/cm$^2$ at a fluence range of 0.1-20 (e.g. 13 as provided by Lumisource®) mW/cm$^2$ is appropriate. For red light, a light dose of 0.03-1 J/cm$^2$, e.g. 0.3 J/cm$^2$, at a fluence range of 0.1-5 mW/cm$^2$, e.g. 0.81 mW/cm$^2$, may be used. In one embodiment the illumination is for a prolonged period of time but at a lower light intensity. For example, the illumination may be for a period of 1 hour or 60 minutes but with ⅒ of the intensity discussed above. Alternatively, the cell may be illuminated via ambient illumination, such as from any standard light source in a laboratory or an operating surgery or room. In one embodiment the subject or patient may receive ambient illumination after administration of the composition or vaccine according to the invention, or the subject or patient may receive ambient illumination after approximately 4 hours, e.g. 3 to 7 hours, such as 5 to 6 or 4.5 to 5.5 hours in darkness.

Furthermore, if cell viability is to be maintained, the generation of excessive levels of toxic species is to be avoided and the relevant parameters may be adjusted accordingly.

The methods of the invention may inevitably give rise to some cell damage by virtue of the photochemical treatment i.e. by photodynamic therapy effects through the generation of toxic species on activation of the photosensitizing agent. Depending on the proposed use, this cell death may not be of consequence and may indeed be advantageous for some applications (e.g. melanoma treatment). In most embodiments, however, cell death is avoided to allow the generation of an immune response from the presenting cell. The methods of the invention may be modified such that the fraction or proportion of the surviving cells is regulated by selecting the light dose in relation to the concentration of the photosensitizing agent. Again, such techniques are known in the art.

Preferably, substantially all of the cells, or a significant majority (e.g. at least 75%, more preferably at least 80, 85, 90 or 95% of the cells) are not killed. In making this assessment for the in vivo methods of the invention, cell death (of one or more cell types) within a 1 cm radius of the point of administration (or depth within tissue) may be examined. Cell viability following PCI treatment may be measured by standard techniques known in the art such as by microscopy. As cell death may not occur instantly, the % cell death refers to the percent of cells which remain viable within a few hours of irradiation (e.g. up to 4 hours after irradiation) but preferably refers to the % viable cells 4 or more hours after irradiation.

As discussed above, the present invention provides a method of generating an immune response in a subject, comprising administering to said subject a melanoma antigen and a photosensitizing agent as defined hereinbefore, and irradiating said subject with light of a wavelength effective to activate said photosensitizing agent, wherein an immune response is generated.

An "immune response" which may be generated may be humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8 T cells. The extent of an immune response may be assessed by markers of an immune response, e.g. secreted molecules such as IL-2 or IFNγ or the production of antigen specific T cells (e.g. assessed as described in the Examples).

The stimulation of cytotoxic cells or antibody-producing cells, requires antigens to be presented to the cell to be stimulated in a particular manner by the antigen-presenting cells, for example MHC Class I presentation (e.g. activation of CD8$^+$ cytotoxic T-cells requires MHC-I antigen presentation). Preferably the immune response is stimulated via MHC-I presentation.

Preferably the immune response is used to treat or prevent melanoma.

Preferably the method is used for vaccination. As referred to herein, "vaccination" is the use of an antigen (or a molecule containing an antigen) to elicit an immune response which is prophylactic or therapeutic against the development (or further development) of a disease, disorder or infection, wherein that disease, disorder or infection is associated with abnormal expression or presence of that antigen. According to the present invention the disease is melanoma.

In one embodiment the vaccination is therapeutic, i.e. the vaccination can treat a pre-existing melanoma. In an alternative embodiment, the vaccination is prophylactic, i.e. the vaccine can reduce or prevent the development of melanoma.

In a preferred embodiment of the present invention, the subject of the method, e.g. vaccination, is a mammal, preferably a cat, dog, horse, donkey, sheep, pig, goat, cow, mouse, rat, rabbit or guinea pig, but most preferably the subject is a human.

The agents used in the methods of the invention may be administered to the subject separately or sequentially or in some cases simultaneously as described hereinbefore.

Aspects and features discussed above in relation to the method of expressing an antigenic molecule or a part thereof on the surface of a cell of the present invention, where appropriate, are also applicable to the other methods described herein, e.g. the method of generating an immune response above.

The invention also provides a method for introducing a melanoma antigen into the cytosol of a cell in a subject, comprising contacting said cell with the melanoma antigen to be introduced and a photosensitising agent as defined herein, and irradiating the cell with light of a wavelength effective to activate the photosensitising agent. Once activated, intracellular compartments within said cell containing said compound release the molecule contained in these compartments into the cytosol.

Compositions comprising the melanoma antigen and/or photosensitizing agents for use in methods of the invention (and products of the invention) may be formulated in any convenient manner according to techniques and procedures known in the pharmaceutical art, e.g. using one or more pharmaceutically acceptable diluents, carriers or excipients. "Pharmaceutically acceptable" as referred to herein refers to ingredients that are compatible with other ingredients of the compositions (or products) as well as physiologically acceptable to the recipient. The nature of the composition and carriers or excipient materials, dosages etc. may be selected in routine manner according to choice and the desired route of administration, purpose of treatment etc. Dosages may likewise be determined in routine manner and may depend upon the nature of the molecule (or components of the composition or product), purpose of treatment, age of patient, mode of administration etc. In connection with the photosensitizing agent, the potency/ability to disrupt membranes on irradiation, should also be taken into account.

As mentioned above, the invention provides a melanoma antigen and a photosensitizing agent as defined herein, for use in expressing said melanoma antigen or a part thereof on the surface of a cell, or for use in prophylaxis or therapy or for use in stimulating an immune response, for example for vaccination purposes, e.g. for stimulating CTLs, in a subject, preferably for treating or preventing melanoma in said subject Preferably said use comprises a method of the invention as defined herein. Alternatively defined the present invention provides use of a melanoma antigen and/or a photosensitizing agent, for the preparation of a medicament for use in stimulating an immune response (e.g. for stimulating CTLs) in a subject, preferably for treating or preventing melanoma in said subject, preferably for vaccination wherein preferably said immune response is stimulated by a method of the invention as defined herein.

Said stimulation, treatment or prevention preferably comprises administering said medicament to said subject.

The invention further provides a product comprising a melanoma antigen, and a photosensitizing agent as defined herein as a combined preparation for simultaneous, separate or sequential use in stimulating an immune response in a subject (or for expressing said melanoma antigen or a part thereof on the surface of a cell or for internalising the melanoma antigen into the cytosol of a cell) wherein preferably said immune response is stimulated by said melanoma antigen or part thereof expressed on the cell's surface in a method as defined herein, preferably to treat or prevent melanoma in a subject.

The present invention also provides a kit for use in stimulating an immune response in a subject, preferably for treating or preventing melanoma in said subject, for example for use in vaccination or immunisation, or for expressing said melanoma antigen or a part thereof on the surface of a cell or for internalising the melanoma antigen into the cytosol of a cell preferably by a method as defined herein, said kit comprising a first container containing a photosensitizing agent as defined herein; and a second container containing said melanoma antigen as defined herein.

The products and kits of the invention may be used to achieve cell surface presentation (or therapeutic methods) as defined herein.

The antigenic presentation achieved by the claimed invention may advantageously result in the stimulation of an immune response. Preferably an immune response which confers protection against subsequent challenge by an entity comprising or containing said antigenic molecule or part thereof is generated, and consequently the invention finds particular utility as a method of vaccination.

Melanoma may be treated or prevented by the generation of an immune response, e.g. by eliminating abnormal or foreign cells which may be identified on the basis of an antigen (or its level of expression) which allows discrimination (and elimination) relative to normal cells.

As defined herein "treatment" refers to reducing, alleviating or eliminating one or more symptoms of the melanoma which is being treated, relative to the symptoms prior to treatment. "Prevention" (or prophylaxis) refers to delaying or preventing the onset of the symptoms of the melanoma. Prevention may be absolute (such that no further melanoma occurs) or may be effective only in some individuals or for a limited amount of time.

The present invention encompasses all combinations of the preferred aspects described herein. One or more of the preferred features discussed above may be used in combination with any of the other preferred features. By way of example, the incubation time may be 18 hours, and can be used with one or more of any of the preferred features discussed above, for example the preferred photosensitizing agent, preferred doses of a photosensitizing agent, particularly a preferred photosensitizing agent, preferred illumination times, preferred dose of antigen, preferred antigens, preferred cell types, preferred light sources, preferred routes of administration and subjects.

For example, methods of the present invention may encompass one or more, for example two, three, four, five or six of the preferred features discussed herein, although additional preferred features can be included.

All combinations of the preferred features are contemplated, particularly as described in the Examples. Each of the features described in the Examples are preferred aspects which may be considered preferred features in combination with any of the embodiments described hereinbefore.

The invention will now be described in more detail in the following non-limiting Examples with reference to the following drawings in which:

FIG. 1 shows that prophylactic PCI-based immunisation stimulated CD8 T-cell responses and prevented tumour growth in mice. (A-D) Groups of five C57BL/6 mice were immunised intradermally (i.d.) with 10 µg OVA protein, with OVA and the photosensitiser $TPCS_{2a}$, (OVA-PCI) or left untreated (Untr). 18 h later, all mice were treated with light (4.86 J/cm2). Mice were bled on day 6 and analysed for SIINFEKL-specific CD8+ cells (A), and their CD44 expression (B) and IFN-γ production (C) by flow cytometry. Survival of mice challenged on day 4 after vaccination with 500,000 OVA-expressing B16 melanoma tumour cells by i.d. injection into one of the flanks (D). Frequency of SIINFEKL-specific $CD8^+$ and $CD44^+$ cells (E) and survival after tumour challenge (F) in C57BL/6 and syngeneic MHC class-II-deficient mice immunised with OVA-PCI and challenged with B16 as above. *, p<0.001; , p<0.01; n.s. not significant. Shown are means and SEM. The data are representative from 2-4 experiments.

FIG. 2 shows that therapeutic PCI-based vaccinated prevented tumour growth in mice. (A-D) Groups of five C57BL/6 mice received 500,000 OVA-expressing B16 melanoma tumour cells by i.d. injection into one of the flanks and were immunised 7 days later i.d. with 10 µg OVA, OVA-PCI or left untreated as described for FIG. 1. On day 8, all mice were light treated. Tumour growth (A) and survival (B) of mice was monitored until day 15, when mice were euthanized and splenocytes analysed for SIINFEKL-specific CD8+ CD44+ T cells (C) and for intracellular IFN-γ production (D) by flow cytometry. **, p<0.01; *, p<0.05; n.s. not significant. Shown are means and SEM. The data are representative from 3 experiments.

FIG. 3 shows that PCI-based vaccination induced CD8 T-cell tumour infiltration and apoptosis. Mice were treated as described in FIG. 2. On day 15, tumours were excised and analysed by immune histochemistry for CD8 (A), CD4 (B) and caspase-3 (D) positive cells as well as stained for haematoxylin and eosin (C) Arrows show apoptotic foci in the H/E staining (C, bottom panel) and caspase-3 positive cells (D, bottom panel). Images are representative of five mice per group.

FIG. 4 shows that PCI-based vaccination reduced the metastatic potential of melanoma. Groups of four C57BLJ6 mice immunised i.d. with 10 µg OVA, OVA-PCI or left untreated as described for FIG. 1. On day 8, the mice received 500,000 OVA-expressing B16 melanoma tumour cells by tail vein injection. On day 19, the mice were killed and lungs isolated for detection of melanoma metastasis.

FIG. 5 shows that PCI facilitates cytosolic delivery of antigen. Bone marrow DCs from C57BL/6 mice were incubated with $TPCS_{2a}$ and OVA-Alexa488. (A) After steps of washing, and light activation (3 min LumiSource exposure), the cells were immediately analysed by fluorescence microscopy. (B) DCs were incubated with OVA-Alexa488 as above and light activated. Images of the same microscopic field were made 0, 5, 10, and 15 min after light activation.

FIG. 6 (A) shows the experimental set up of PCI-mediated immunisation using mice adoptively transferred with OVA-specific CD8 T-cell transgenic OT-1 cells prior to immunisation. (B) After intradermal injection of antigen (OVA) and photosensitiser ($TPCS_{2a}$) in the abdominal region, mice were anaesthetised and the site of injection illuminated by placing the mice belly down on a LumiSource light table.

FIG. 7 shows results with C57BL/6 mice that were spiked with $5 \times 10^6$ OT-I cells and the frequency of SIINFEKL-specific cells were measured in the recipients after 18 hours by MHC I-SIINFEKL pentamer staining and flow cytometry (A). The mice were then immunised with 100 μg OVA or with 100 μg OVA and 25 μg $TPCS_{2a}$; control mice were left untreated. After 2 or 18 hours, the $TPCS_{2a}$-treated mice were illuminated. On day 6 (B) and 23 (C), mice were bled and stained with MHC I-SIINFEKL pentamer, anti-CD8 and anti-CD44 antibodies and analysed by flow cytometry. Bars show the frequency of triple positive cells relative to the total number of CD8 T cells. (D) shows dot plots of pentamer- and CD44-positive cells from blood analysed by flow cytometry on day 6. Cells were gated on CD8 lymphocytes. (E) shows results on day 14, blood (left panel) and day 23 splenocytes (right panel) that were re-stimulated overnight with SIINFEKL and analysed for CD8, CD44 and IFN-γ by intracellular staining (ICS). (F) shows results with splenocytes that were re-stimulated with SIINFEKL for analysis of IFN-γ (left panel) and IL-2 (right panel) by ELISA.

FIG. 8 shows results with C57BL/6 mice that were spiked with $1.6 \times 10^6$ OT-I cells. After eight hours, the mice were immunised with 10 μg OVA, with 10 μg OVA and 25 μg $TPCS_{2a}$, or with 10 μg OVA and 250 μg $TPCS_{2a}$. On day 8 the mice were bled and analysed for (A) MHC I-SIINFEKL pentamer, CD44 and CD8 staining. On day 11 the mice were euthanized and their splenocytes analysed for (B) CD8 and CD44 and intracellular IFN-γ, as well as secretion of IL-2 (C) and IFN-γ (D) measured by ELISA. Bars show the frequency of triple positive cells relative to the total number of CD8 T cells.

FIG. 9 shows (A) J774 cells that were incubated overnight with 25 μg/ml OVA-Alexa488 (left panel) or with OVA-Alexa488 and 0.05 μg/ml $TPCS_{2a}$ (right panel). After washing and 90 minutes incubation in fresh medium, the cells were illuminated, and the cellular uptake and distribution of OVA-Alexa488 was analysed by fluorescence microscopy. (B) J774 cells were incubated with 1.0 μg/ml $TPCS_{2a}$ and 25 μg/ml OVA-Alexa488 as above and analysed for cellular uptake, distribution and co-localisation of OVA-Alexa488 and $TPCS_{2a}$ by fluorescence microscopy. Co-localisation of the two compounds causes emission of yellow fluorescence.

FIG. 10 shows results with C57BL/6 mice that were spiked with $1.6 \times 10^6$ OT-I cells. After eight hours, the mice were immunised with 100 μg OVA, or with 100 μg OVA and 25 μg $TPCS_{2a}$; control mice were left untreated. After 2, 6 or 18 hours, the $TPCS_{2a}$-treated mice were illuminated. On day 0 and day 7 mice were bled and stained with MHC I-SIINFEKL pentamer and anti-CD8 antibodies and analysed by flow cytometry (A). On days 0, 7, 14 blood cells and day 23 splenocytes were stained with anti-CD8 antibodies and pentamer and analysed by flow cytometry (B). Each circle represents the results for a different animal.

FIG. 11 shows a similar study to that shown in FIG. 10 but time points of 18 hours and 42 hours after illumination were assayed. On day 0 and day 7 mice were bled and stained with MHC I-SIINFEKL pentamer and anti-CD8 antibodies and analysed by flow cytometry (A). On days 0, 7 blood cells and day 14 splenocytes were stained with anti-CD8 antibodies and pentamer and analysed by flow cytometry (B). (C) shows splenocytes that were re-stimulated overnight with SIINFEKL and analysed for IFN-γ by ELISA. IFN-γ was also analysed on day 14 by flow cytometry (D).

FIG. 12 shows a similar study to that shown in FIG. 10 but the illumination time was varied between 3, 6 and 12 minutes (incubation time was 18 hours). On days 0, and 9 the mice were bled and the cells analysed for MHC I-SIINFEKL pentamer and CD8 staining by flow cytometry (A). On day 0 and day 9 mice were bled and stained with MHC I-SIINFEKL pentamer and anti-CD8 antibodies and assessed by flow cytometry (B). (C) shows splenocytes from day 14 that were re-stimulated overnight with SIINFEKL and analysed for IL-2 and IFN-γ by ELISA.

FIG. 13 shows a similar study to that shown in FIG. 10 but the photosensitiser dose was varied between 25, 50 and 100 μg $TPCS_{2a}$. An illumination time of 6 minutes and incubation time of 18 hours was used. On day 7 the mice were bled and cells stained with pentamer and anti-CD8 antibodies and assessed by flow cytometry (A). On day 7 blood cells were stained with anti-CD8 antibodies and analysed by flow cytometry (B). On day 12 splenocytes were analysed for IFN-γ, CD8 and CD44 staining (left panel) and MHC I-SIINFEKL pentamer and CD8 staining, (right panel) by flow cytometry (C).

FIG. 14 shows results with C57BL/6 mice that were spiked with $2 \times 10^6$ OT-I cells. One day later, the mice were immunised with 20 μg OVA, with 20 pg OVA and 200 μg $TPCS_{2a}$, or left untreated. On day 54, the mice were euthanized and the splenocytes analysed by flow cytometry for (A) MHC I-SIINFEKL pentamer and CD8 staining, or (B) intracellular IFN-γ and CD8 and CD44 staining. Bars show the frequency triple positive cells relative to the total number of CD8 T cells. (C) Secretion of IFN-γ into 96-hours splenocyte cultures was measured by ELISA.

FIG. 15 shows the effect of PCI-based vaccination on tumour growth. C57BL/6 mice were spiked with $1 \times 10^4$ OT-I cells. One day later, the mice were immunised with 20 μg OVA, with 20 μg OVA and 200 pg $TPCS_{2a}$, or left untreated. The abdomen was shaved before vaccination. The abdominal region was illuminated for six minutes 18 hours after vaccination. On day 4 after immunisation, the mice received an intradermal injection of $5 \times 10^5$ SIINFEKL-expressing B16 mouse melanoma cells. Two weeks thereafter, the tumour volume was measured (A) and the tumour photographed (B). n.s.: not significant; *: p<0.05 as analysed by Kruskal-Wallis test.

FIG. 16 shows the effect of PCI-based vaccination on tumour growth. Methods similar to those in FIG. 1 were used, but using 150 μg $TPCS_{2a}$ and/or 10 μg OVA and $2.5 \times 10^5$ OVA-expressing B16 mouse melanoma cells. The frequency of OVA-specific CD8 T-cells was analyzed by flow cytometry (A). The tumour growth was monitored from day 13 after vaccination (B) until the volume of the tumours reached the endpoint, 1000 mm³. On day 36 the experiment was ended. (C) shows the average results for tumour growth.

FIG. 17 shows the effect of therapeutic vaccination on tumour size. Methods similar to those in FIG. 2 were used but using 150 µg TPCS$_{2a}$ and/or 10 µg OVA. On days 7 and 14 after vaccination the animals were bled (by tail bleeding), and the frequency of OVA-specific CD8 T-cells was analyzed by flow cytometry (A). The tumour growth was monitored from day ten after injection of tumour cells until the volume of the tumours reached the endpoint, 1000 mm³. On day 35 the experiment was terminated. (B) shows the average results for tumour growth.

FIG. 18 shows results of a further prophylactic vaccination with male mice. Methods similar to those in FIG. 1 were used except that 150 µg TPCS$_{2a}$ and/or 10 µg OVA were used. frequency of OVA-specific CD8 T-cells was analysed by flow cytometry.

FIG. 19 shows the effect of the adjuvants poly(IC) and CpG. Mice were immunised with 10 µg of OVA, with 100 µg OVA, with 10 µg OVA and 150 µg TPCS$_{2a}$, with 10 µg OVA and 50 µg ODN2935 CpG oligonucleotide, with 10 µg OVA, 50 µg ODN2935 CpG oligonucleotide and 150 µg TPCS$_{2a}$, with 10 µg OVA and 50 µg Poly(IC), with 10 µg OVA, 50 µg Poly(IC) and 150 µg TPCS$_{2a}$ or left untreated. Mice receiving TPCS$_{2a}$ were illuminated. Mice were bled on day 7 and the frequency of OVA-specific CD8 T-cells was analyzed by flow cytometry. On day 14 spleen cells were obtained and restimulated by SIINFEKL peptide and analysed by Interferon-gamma ELISA. (A) shows the average values (% antigen-specific, CD44$^+$ cells of the total CD8$^+$ cells) in blood at day 7 for the experimental groups (5 animals in each group, error bars: standard error of the mean). (B) shows results from interferon-gamma (IFN-gamma) ELISA after restimulation of day 14 spleen cells with SIINFEKL peptide.

FIG. 20 shows the results of a study in which normal mice were immunised at day 0 and at day 14 with 50 µg of TRP-2 peptide, 100 µg TPCS$_{2a}$ and 10 µg poly(IC) as shown. On day 7 after immunisation mice were bled by tail bleeding and erythrocytes were removed by lysis. The frequency of antigen specific CD8 T-cells in the blood was monitored by flow cytometry after staining the cells with anti-CD8 and anti-CD44 antibodies and TRP-2 pentamers. The activation status of the cells was analysed by testing the expression of CD44 by flow cytometry. FIG. 20 shows the average values (% antigen-specific, CD44+ cells of the total CD8+ cells) for the TRP-2 pentamer stained experimental groups after the second immunisation.

FIG. 21 shows the results of a study in which normal mice were immunised at day 0 and at day 14 and at day 35 with 200 µg of TRP-2 peptide, 100 µg TPCS$_{2a}$ and 10 µg poly(IC) as shown. On day 7 after immunisation mice were bled by tail bleeding and erythrocytes were removed by lysis. The frequency of antigen specific CD8 T-cells in the blood was monitored by flow cytometry after staining the cells with anti-CD8 and anti-CD44 antibodies and TRP-2 pentamers. The activation status of the cells was analysed by testing the expression of CD44 by flow cytometry. FIG. 21 shows the average values (% antigen-specific, CD44+ cells of the total CD8+ cells) for the TRP-2 pentamer stained experimental groups after the second immunisation.

Figure 24:
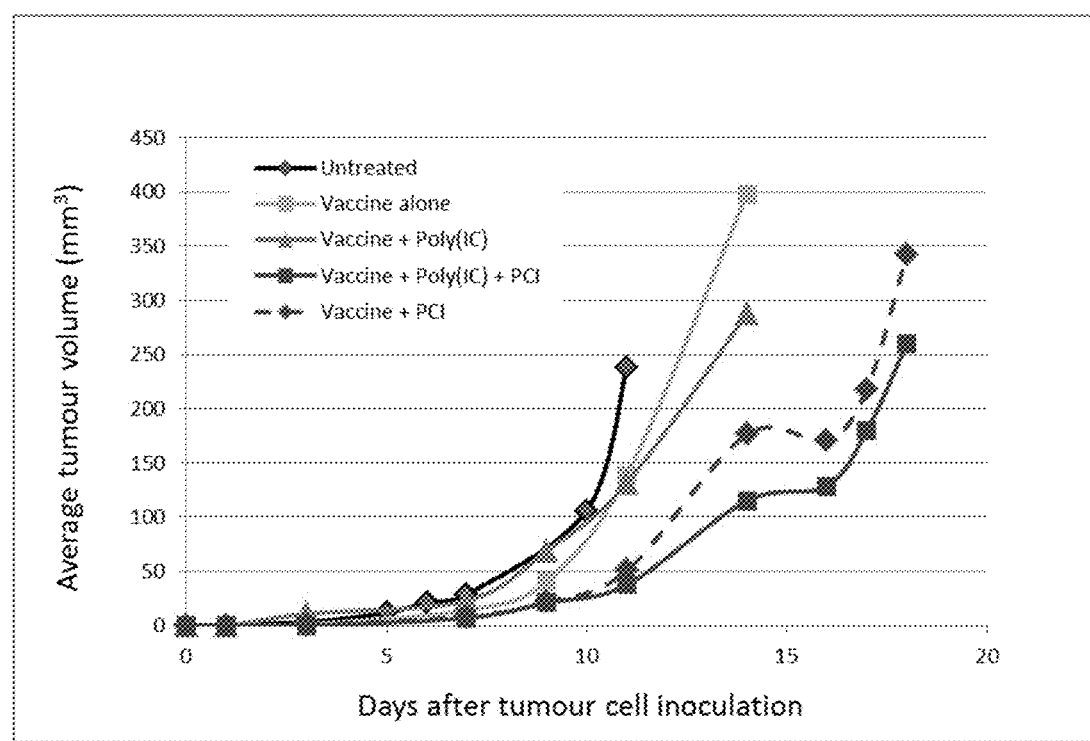

FIG. 24 shows the results of a study in which mice were immunised at day 0 and at day 14 with 1×10⁶ irradiated B16-F10 melanoma cells, 150 µg TPCS$_{2a}$ and 10 µg poly (IC) as shown. At day 21 5×10⁵ B16-F10 cells were injected intradermally, and the size of the tumours was measured at least 2 times per week. FIG. 24 shows the average tumour volume with day 0 being the day the cells were injected.

EXAMPLES

Example 1

Materials and Methods

Animals C57BL/J6 mice were purchased from Harlan (Horst, The Netherlands). CD8 T-cell receptor transgenic OT-I mice (B6.129S6-Rag2tm1Fwa Tg(TcraTcrb)1100Mjb) from Taconic Europe (Ry, Denmark) and MHC class II-deficient mice (B6.129S2-H2dlAb1-Ea/J) from Jackson Laboratories (Bar Harbor, Maine) and bred in our own SPF facilities at the University of Zurich; the OT-I CD8 T cells recognise the H-2K$^b$-restricted epitope SIINFEKL from ovalbumin (OVA, aa257-264). All mice were kept under SPF conditions, and the procedures performed were approved by Swiss Veterinary authorities (licence 69/2012).

Materials and Cells

Chicken OVA was purchased from Sigma-Aldrich (Buchs, Switzerland) and the SIINFEKL peptide from EMC microcollections (Tuebingen, Germany). The photosensitiser tetraphenyl chlorin disulfonate (TPCS$_{2a}$) was from PCI Biotech (Lysaker, Norway). OVA and TPCS$_{2a}$ were mixed in PBS, kept light protected, and administered to mice within 60 minutes of preparation. TPCS$_{2a}$ was activated by illumination with LumiSource™ (PCI Biotech). B16.F10 melanoma cells (ATCC® CRL-6322™), originally from C57BL/6 mice, were used to make a stable transfectant that expressed the whole OVA antigen.

Intradermal Photosensitisation and Immunisation of Mice

C57BL/6 mice were immunised at 6-10 weeks of age. One day prior to immunisation, 10,000 OT-I spleen and lymph node cells were administered by intravenous injection into the recipient C57BL/6 mice (see Example 2). The next day, the fur was shaven off the abdominal region and 100 µl of the vaccine preparations were injected intradermally. The doses of OVA and TPCS$_{2a}$ were 10 µg and 100 µg, respectively. After 18 hours, the anaesthetised mice were placed on the light source for six minutes illumination (4.86 J/cm2) for activation of TPCS$_{2a}$.

Analysis of Immune Responses by Flow Cytometry and ELISA

The frequency of antigen-specific CD8 T cells was monitored in blood and spleen by flow cytometry using H-2K$^b$/SIINFEKL Pro5 pentamer (Proimmune, Oxford, UK). Cell-surface expression of CD4, CD8, and CD44 and intracellular production of IFN-γ was analysed by flow cytometry after Fc-receptor blocking with anti-CD16/32. The intracellular staining was after overnight incubation at 37° C. with 0.1 µg SIINFEKL. Brefeldin A (2.5 µg/ml) was added during the last 4 hours. The cells were fixed with 4% formaldehyde for 10 minutes, permeabilised in 0.1% NP40 for 3 minutes, and stained with anti-IFN-γ for 35 minutes. All staining was performed at 4° C. and all steps followed by washing in PBS/FCS 2%. FACS antibodies were from eBioscience (Vienna, Austria) or BD Pharmingen (Basel, Switzerland).

Acquisition was performed on FACSCanto (BD Biosciences, San Jose, USA) and data analysed with FlowJo 8.5.2 (Tree Star, Inc., Ashland, Oreg.). For analysis of cytokine secretion by ELISA, $2\times10^5$ splenocytes were re-stimulated in round-bottom 96-well plates with 0.1 µg SIINFEKL. Supernatants were collected after 24-72 hours and analysed using cytokine ELISA kits (eBioscience).

Fluorescence Microscopy of Cytosolic Antigen Release

Cells (J774.1 (ATCC no. TIB-67 mouse monocyte macrophage cell line) or bone marrow DCs from C57BL/6 mice) were incubated with 0.05 or 1.0 µg/ml TPCS$_{2a}$ and 25 µg/ml OVA-Alexa488 for 18 hours and washed three times in drug-free culture medium prior to incubation for four hours before light activation (3 min LumiSource exposure). The cells were subsequently washed in ice-cold PBS with $Ca^{2+}$ and $Mg^{2+}$ prior to microscopy. Images of cellular localization and PCI-induced cytosolic release of OVA were obtained by epi-fluorescence microscopy using a Plan-Apochromat 63×/1.40 Oil differential interference contrast (DIC) objective or 40×/0.95 Plan-Apochromat phase contrast (Korr Ph3 M27) objective with a Zeiss Axioimager Z.1 microscope (Carl Zeiss, Oberkochen, Germany). Fluorescence of Alexa488-labelled OVA was obtained by using a 470/40 nm band pass (BP) excitation filter with a beam splitter at 495 nm and a 525/50 nm BP emission filter. TPCS$_{2a}$ fluorescence was obtained by using a 395-440 nm BP excitation filter with a beam splitter at 460 nm, and a 620 nm long pass filter. Micrographs were recorded with a digital AxioCam MRm camera and processed and analysed by use of the Axiovision Software (Carl Zeiss).

Vaccination Against Intradermal Melanoma and Monitoring of Tumour Growth

If not otherwise stated, C57BL/6 mice were vaccinated as described above 4-5 days prior to, or 7-8 days after, the tumour challenge with 500,000 OVA-expressing B16-melanoma cells injected intradermally into one of the mouse flanks; 10,000 OT-I cells were transferred intravenously to the recipient one day before prophylactic vaccination, or one day before B16 injection in the therapeutic vaccination model. In the therapeutic vaccination model, the 7-8 days after B16 injection represents the time required for the tumour to develop to a palpable size. The tumour growth was monitored by measuring the size of the neoplasm with a calliper. The tumour volume was calculated using of the modified ellipsoid formula: (length×width$^2$)/2.

Histological Analysis Of Tumour and Tumour Infiltrates

C57BLJ6 mice received 500,000 OVA-expressing B16-melanoma cells intradermally as described above. Six days later, the mice were vaccinated with 10 µg OVA ±100 µg TPCS$_{2a}$ as described above. On day 7, the mice were treated with 4.86 J/cm2 light. On day 15, the mice were euthanized and the tumours excised and cut in two pieces, one snap frozen in liquid nitrogen and one fixed in formalin (2 days) and 60% ethanol before embedded in paraffin. The frozen tissues were sectioned and stained with anti-mouse CD8, CD4, and caspase-3 antibodies for immune histochemistry. Paraffin sections were stained with haematoxylin and eosin.

Monitoring of Metastatic Potential of Melanoma

C57BLJ6 mice were vaccinated as above with OVA with or without TPSC$_{2a}$ and challenged four days later with 500,000 OVA-expressing B16 cells given by intravenous injection. On day 19, mice were euthanized and spleens and lungs were harvested. The lungs were analysed by counting melanoma spots as a measure for metastasis. Spleen cells were analysed by flow cytometry for CD8 T-cell activation as described above.

Results

Photosensitisation Enables MHC-class I Antigen Presentation of Protein Vaccines

Figure 1:
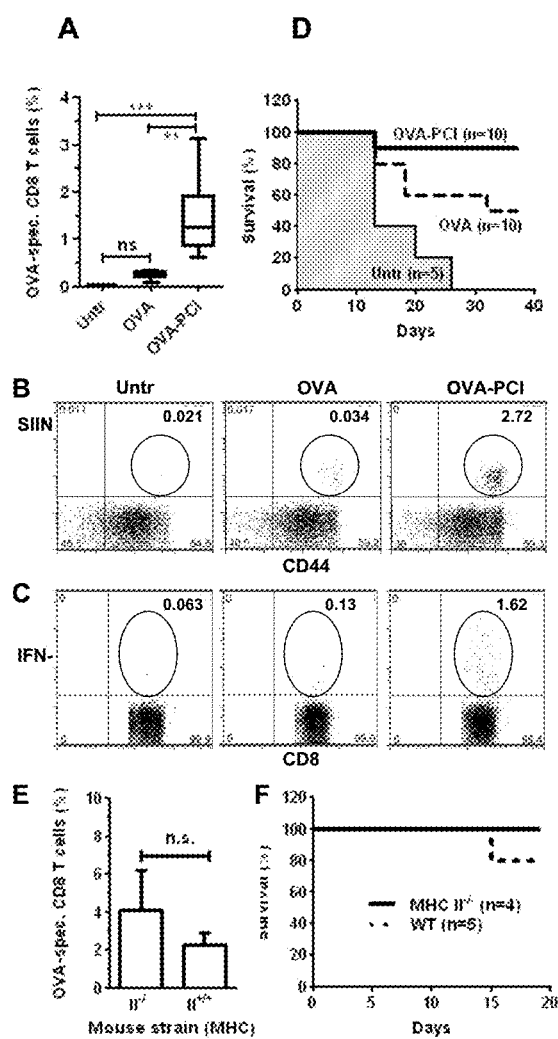
Figure 10A:
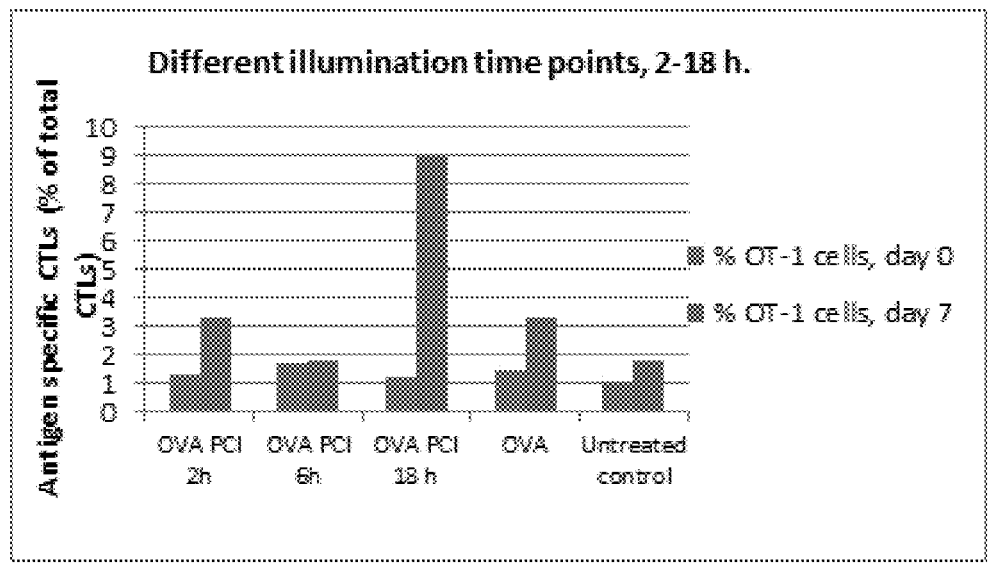
Figure 10B:
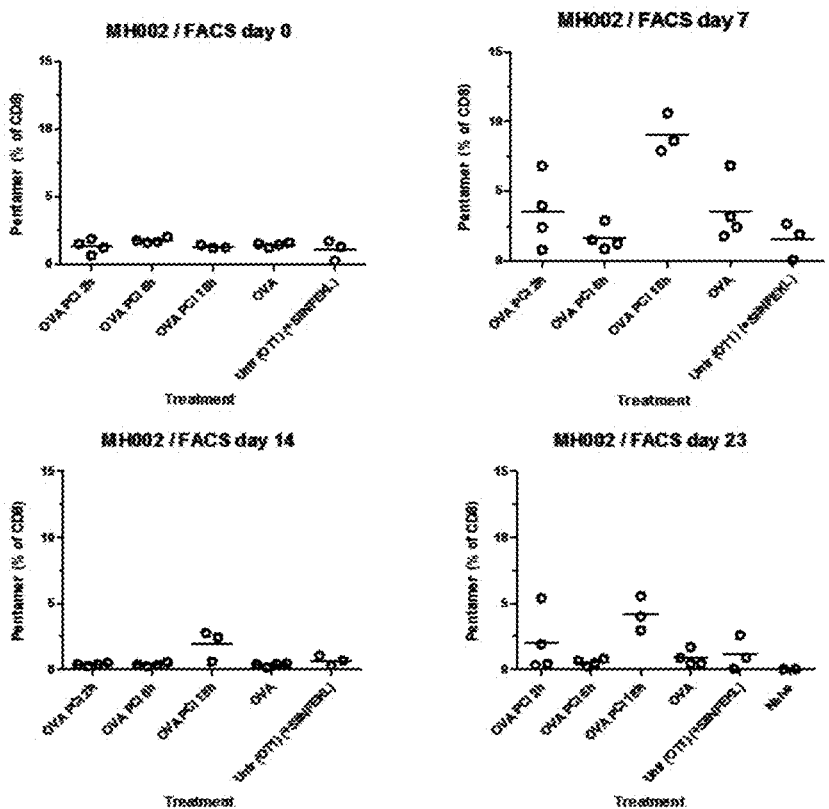
Figure 11A:
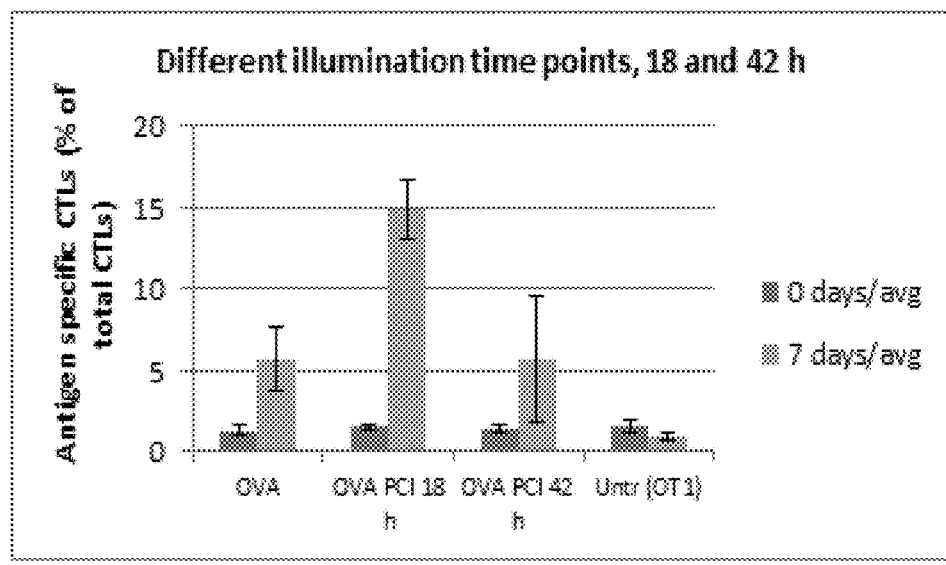
Figure 11B:
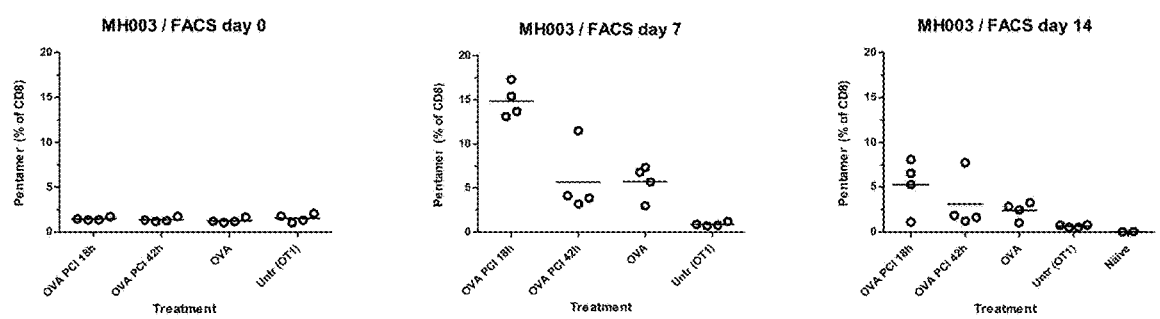
Figure 11C:
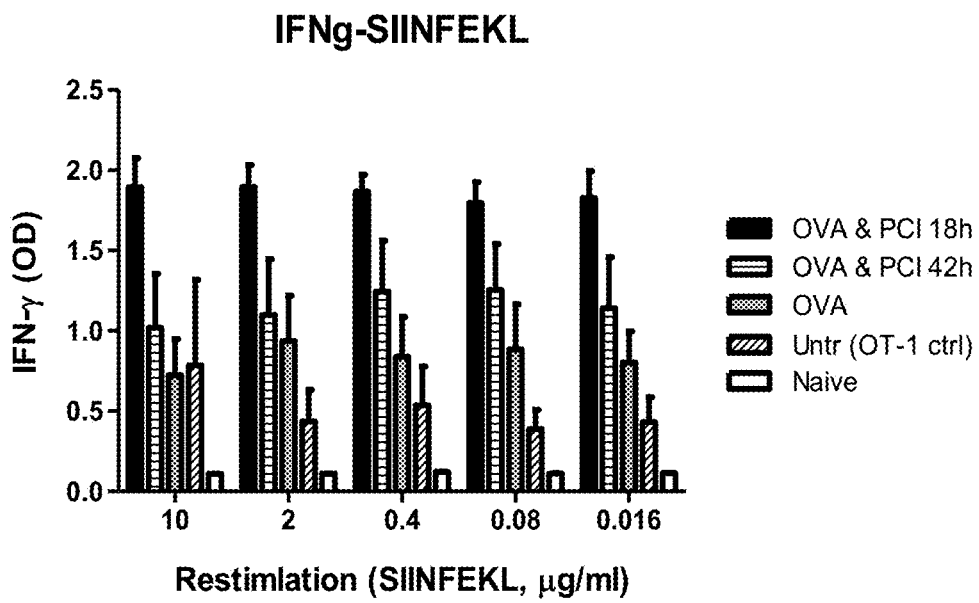
Figure 11D:
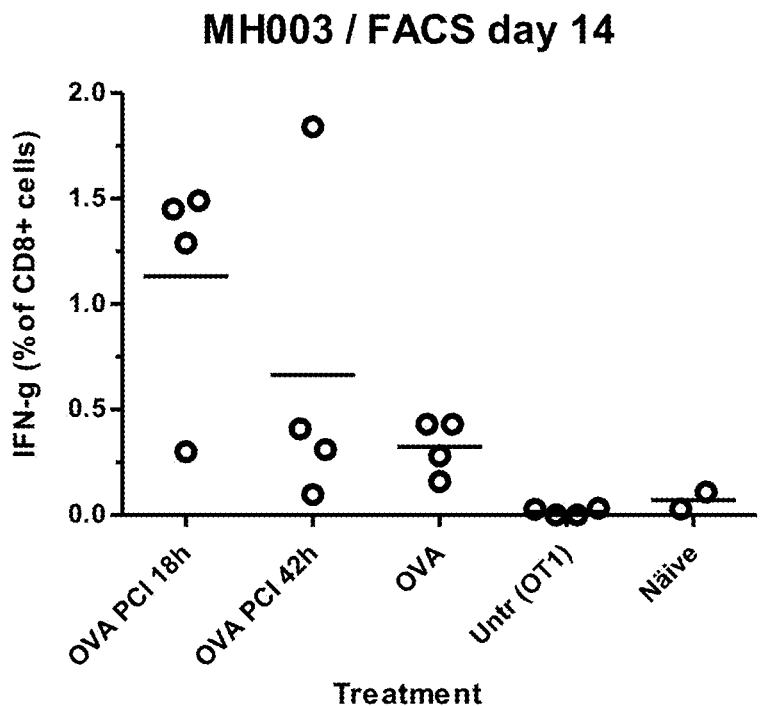
Figure 12A:
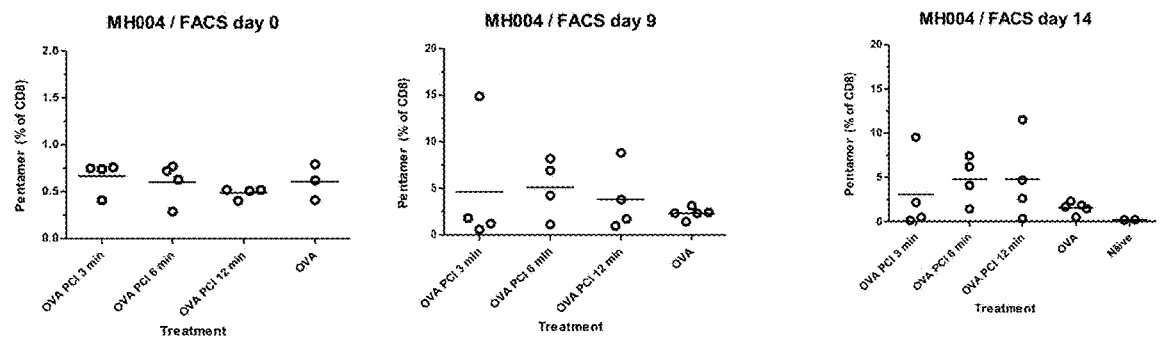
Figure 12B:
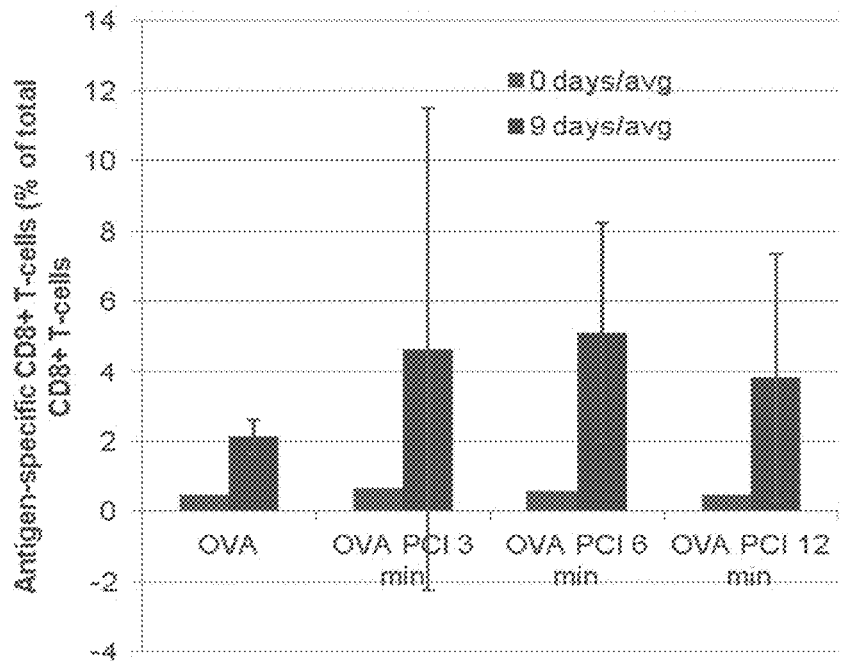
Figure 12C:
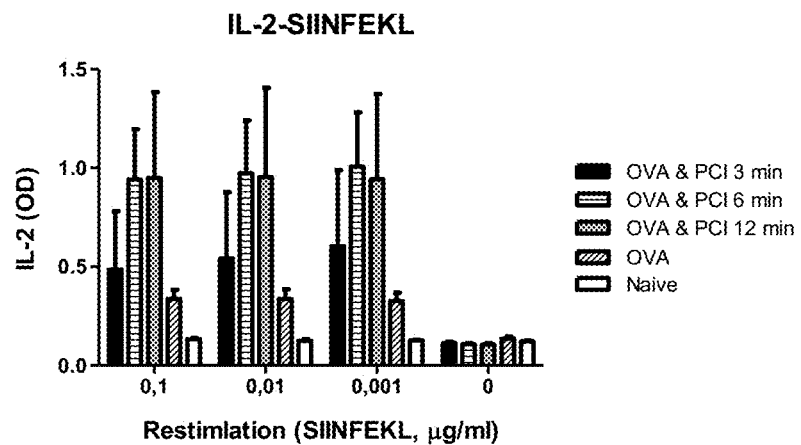
Figure 12D:
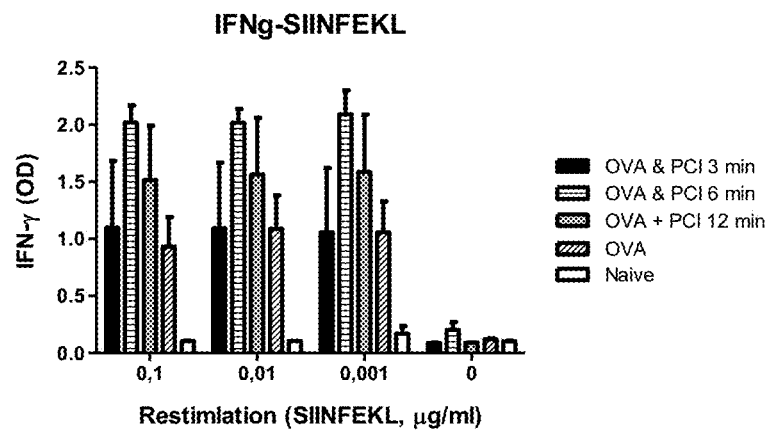

Mice were immunised intradermally with OVA protein with or without photosensitiser and the immune responses analysed by measuring the frequency of pentamer (H2K$^d$-SIINFEKL)-binding CD8 T cells in blood. No or little so-called cross priming was observed in mice immunised with OVA alone. In contrast, concomitant photosensitisation with TPCS$_{2a}$ and illumination of the skin 18 hours later, resulted in photochemical internalisation (PCI) and MHC class-I antigen presentation of the endogenous protein with strong activation of antigen-specific CD8 T cells (FIG. 1A). The CD8 T cells had an activated CD44 phenotype (FIG. 1B) and were IFN-γ producers (FIG. 10).

When splenocytes from immunised mice were re-stimulated in vitro with the MHC class-I-binding peptide SIINFEKL, cells from mice immunised with OVA-PCI secreted significantly more IL-2, TNF-α and IFN-γ, as measured by ELISA of culture supernatants, than cells from mice immunised with OVA alone (data not shown).

PCI-adjuvated immunisation also prevented growth of melanoma when B16 cells were given intradermally five days after immunisation. While no untreated mice survived the tumour challenge longer than 26 days, nine out of ten OVA-PCI immunised mice did not develop tumours (FIG. 1D). Fifty percent of the mice immunised with OVA without concomitant photosensitisation developed tumours and succumbed by days 13 (n=2), 18 (n=2) and 32 (n=1). The protection against tumour growth was also long lived, as mice challenged six weeks after immunisation still showed effective protection (data not shown). In general, tumour protection after immunisation and photosensitisation (OVA-PCI) reflected the stronger activation of SIINFEKL-specific CD8 T cells as analysed by the correlation of the two parameters from several experiments (p<0.01 by Spearman's ρ, n=63).

PCI-Based Stimulation of CD8 T cells is MHC Class II Independent

The hypothesised mechanism of PCI-adjuvated stimulation of CD8 T-cell responses is the light-activated release of antigen from endosomes, and thereby prevention of the default MHC class-II pathway of antigen presentation. However, as activation of CD8 T-cell responses is mostly dependent on CD4 help and MHC class II, it was tested whether the stimulation of CD8 T-cell responses with protein and photosensitiser was dependent on MHC class II. Mice were immunised with OVA, photosensitiser and light exposure as described above. The frequencies of pentamer (H2K$^d$-SIINFEKL)-binding CD8 T cells in blood were not significantly different in MHC class II wild type and deficient mice (FIG. 1E). Indeed, there was actually a slightly higher frequency in the MHC class II-deficient mice. Moreover, when mice were subsequently challenged with the B16 melanoma, wild type mice had no survival benefit as compared to MHC class II-deficient mice (FIG. 1F).

Figure 2:
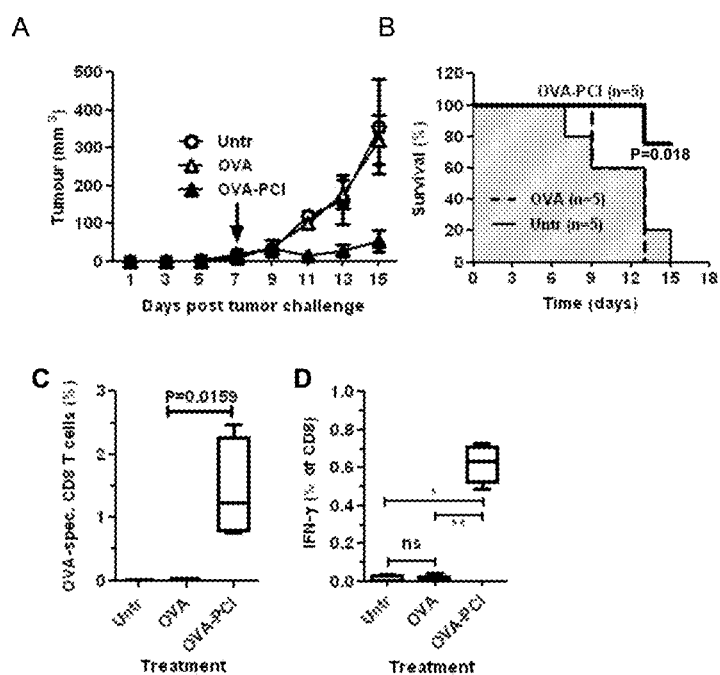

Therapeutic Vaccination with PCI-Based Vaccines Improves Survival in Melanoma-Bearing Mice To study if PCI-based immunisation would also reduce the growth of already established neoplasms, mice were immunised after appearance of tumours under the skin. The tumours grew readily in non-immunised mice and in mice immunised with antigen only (FIG. 2A). In contrast, no growth was observed in mice that received the photosensitive vaccine OVA-PCI. Correspondingly, the survival, as measured by time to reach a tumour volume of 50 mm$^3$, was significantly improved in OVA-PCI-immunised as compared to OVA-immunised mice (FIG. 2B; p=0.018 by log rank Mantel-Cox test). When splenocytes were re-stimulated in vitro with SIINFEKL and analysed by flow cytometry, therapeutic PCI-based vaccination also stimulated proliferation of antigen-specific CD8 T cells (FIG. 2C) that produced IFN-γ (FIG. 2D).

Figure 3:
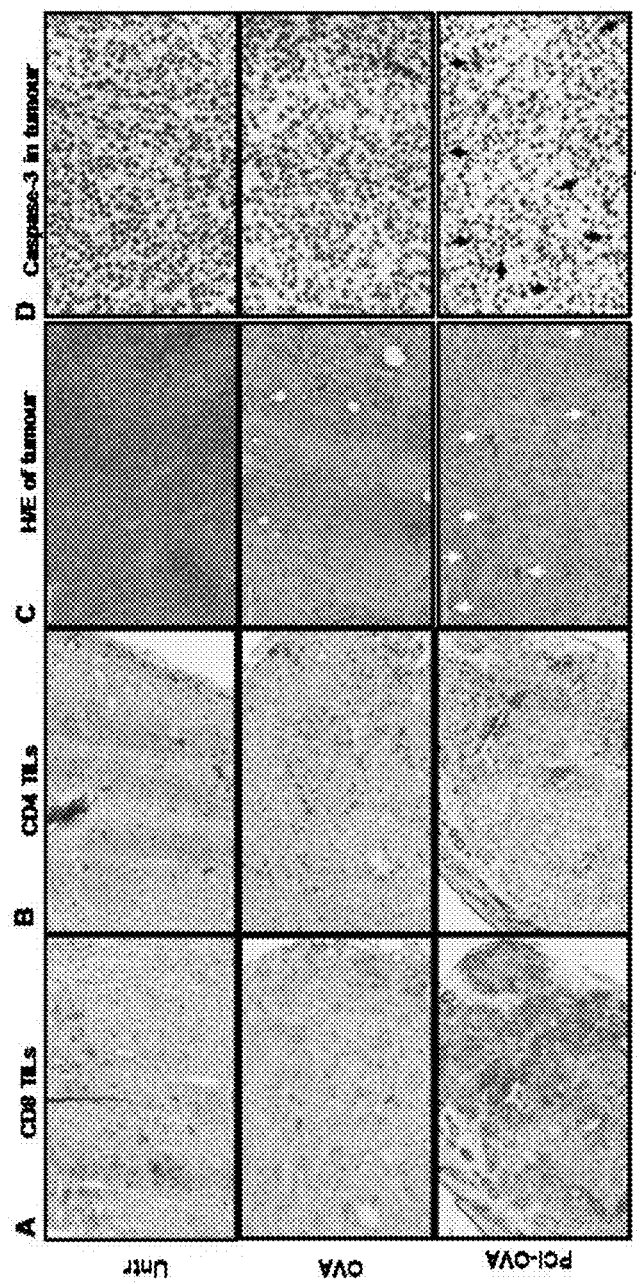

Photosensitive Cancer Vaccines Stimulate TILS to Melanoma and Apoptosis in Tumours Tumours were excised and analysed 10 days after therapeutic vaccination of tumour bearing mice. As illustrated in FIG. 3A, photosensitisation of skin caused a heavy infiltration of CD8 T cells into the intradermal tumour, whereas vaccination with antigen only represented no benefit compared to no treatment. PCI-adjuvated tumour vaccination had no effect on the infiltration of CD4-positive TILs (FIG. 3B). The hematoxylin and eosin (H/E) staining of tumour sections indicated apoptotic cells and foci in melanomas from mice vaccinated with OVA-PCI, but not in mice vaccinated with protein alone or in untreated mice (FIG. 3C). In part, this apoptosis was mediated by caspase-3, as caspase-3 positive cells were observed in OVA-PCI-treated mice, but not in OVA-treated or untreated mice (FIG. 3D).

Figure 4:
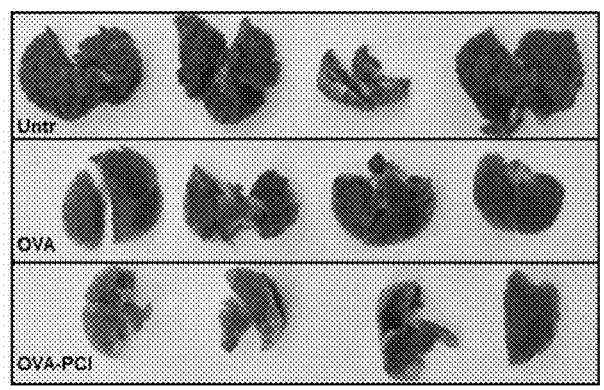

Photosensitive vaccines decrease the metastatic potential of melanoma in mice To study the effect of PCI-based vaccination on metastasis, mice were immunised with OVA alone or with OVA-PCI as described above and challenged one week later with B16 melanoma cells given intravenously; the dissemination of cells to the lung with growth of tumours is an established method for the study of B16 metastatic potential in mice. Nineteen days later, the mice were euthanized and the lungs excised. The lungs of non-immunised mice had innumerable (>100) tumour spots on the surface (FIG. 4, top panel). OVA-immunised mice had on average approx. 50 melanoma spots (FIG. 4, middle panel), while mice immunised with OVA and the photosensitiser TPCS$_{2a}$ had an average of 10 lung metastases (FIG. 4, bottom panel).

Figure 5:
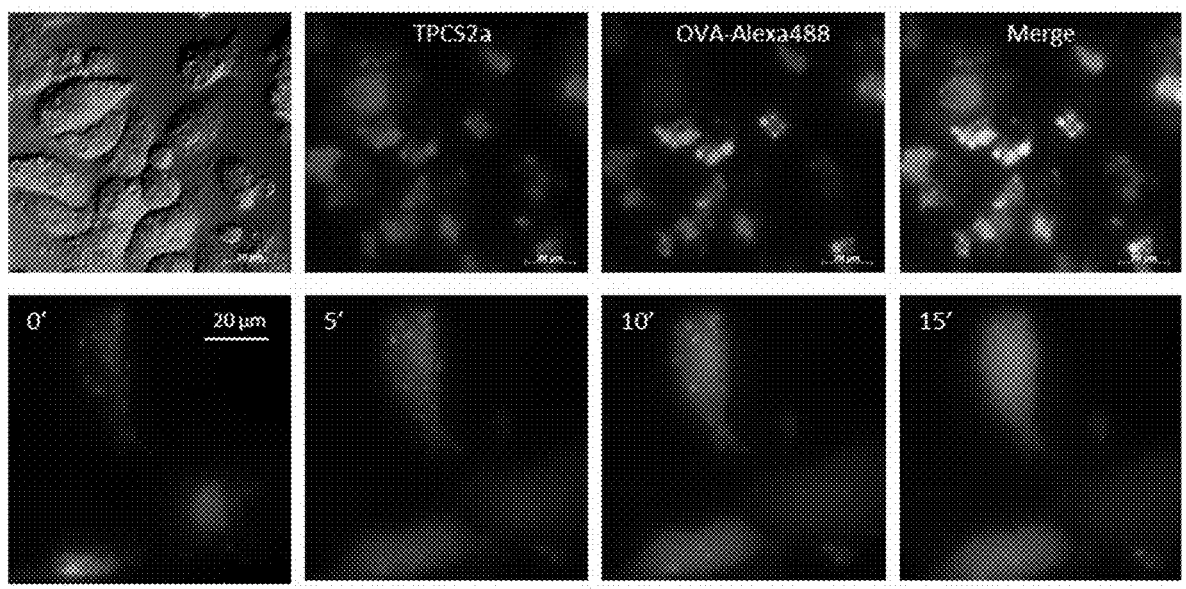

Antigen and Photosensitiser Co-Localise in Endosomes of Dendritic Cells and are Released into Cytosol Upon Light Activation The hypothesised effect of photosensitisation on the stimulation of CD8 T cells immunisation assumes that antigen presenting cells such as DCs have affinity for the photosensitiser and that the photosensitiser translocates to the endosome upon endocytosis of extracellular protein vaccine. Moreover, the effect also assumes that the antigen and the photosensitiser are contained in the same endosomes. To test this, bone-marrow derived DCs were incubated in vitro with the photosensitiser TPCS$_{2a}$ and with Alexa488-labelled OVA protein. After washing of the cells, they were analysed by fluorescence microscopy, which showed co-localisation of antigen and photosensitiser in DC endosomes (FIG. 5A). When the cells were activated by light, release of the antigen into the cytosol could be observed over 15 minutes (FIG. 5B). At this time point, endosomal compartments were no longer visible, and the fluorescent antigen had diffused throughout the cytosol with direct access to the MHC class-I machinery of antigen presentation.

Conclusion

In the current study, it was tested whether PCI could be utilised as adjuvant for induction of anti-tumour CD8 T-cell responses in mice after intradermal administration. Eighteen hours after the vaccination with protein antigen and the photosensitiser TPCS$_{2a}$, a time period that allowed uptake of vaccine into dermal antigen-presenting cells, the injection site was illuminated with light to activate the photosensitiser contained in endosomes. Light activation triggered the release of antigen to cytosol where it was degraded and MHC class-I-presented to CD8 T cells. This method of vaccination stimulated strong immune responses with proliferation and cytokine secretion of CD8 T cells but not of CD4 T cells. The immune responses protected against tumour development in a prophylactic model of mouse melanoma. More importantly, therapeutic vaccination of melanoma-bearing mice prevented further growth of the tumours, while control vaccination without photosensitiser had no effect on tumour growth and mouse survival.

The PCI-based tumour vaccine worked exclusively through stimulation and recruitment of CD8-positive tumour-infiltrating lymphocytes (TILs), cells known to be of vital importance in the immunological fight against tumours. We observed that tumours from PCI-treated mice were heavily infiltrated by CD8-positive T cells, while control vaccination without photosensitiser caused no such infiltration. In contrast, PCI had no effect on the recruitment of CD4-positive TILs. Tumour vaccination with the PCI-based vaccine induced apoptosis in the skin melanoma, which correlated with caspase-3 expression and IFN-γ secretion, a cytokine that inhibits tumour cell growth by inducing apoptosis and by reducing their capability to enter cell cycling.

By fluorescence microscopy, it was verified that antigen and photosensitiser were taken up into endosomes of DCs and that the endosomes were disrupted upon light exposure. Indeed, the light-induced disruption of endosomes and release of antigen into the cytosol was so effective that it may suggest a total turn-off of MHC class-II antigen presentation. Although the purpose of PCI-adjuvated vaccination is to trigger MHC class-I-restricted CD8 T-cell responses, the generation of primary CD8 T-cell responses to non-inflammatory antigens typically requires MHC class II-restricted CD4 T-helper cells. PCI-based vaccination in wild type and MHC class II-deficient mice was therefore compared. Surprisingly, the stimulation of CD8 T-cell responses and the fitness of the CD8 T cells to control tumour growth were not impaired in MHC class II-deficient mice. T-helper-cell-independent PCI-based vaccination is considered important as many tumour patients are treated with CD4 T-cell-sensitive immune suppressive agents, which could impair the efficacy of vaccination.

Altogether, the results presented here show that photochemical internalisation enables high amounts of exogenous protein vaccine to access the cytosol were it is degraded for MHC class-I-restricted antigen presentation. The subsequent strong stimulation of CD8 T-cell responses prevented tumour growth in of murine model of melanoma.

Example 2

Materials and Methods

Mice

Female C57BL/6 mice (used at 6-10 weeks of age) and Rag2 deficient OT-I mice were as described in Example 1 and bred in the facilities at the University of Zurich as described in Example 1.

Materials

The antigen chicken ovalbumin (OVA; Grade V) was purchased from Sigma-Aldrich (Buchs, Switzerland) and dissolved in PBS. The octapeptide OVA aa257-264 (SIINFEKL) and photosensitiser TPCS$_{2a}$ were obtained as described in Example 1. TPCS$_{2a}$ was at a concentration of 30 mg/ml in polysorbate 80, mannitol and 50 mM Tris pH 8.5. $TPCS_{2a}$ was protected from light and kept at 4° C. Prior to vaccination OVA and $TPCS_{2a}$ were mixed together in PBS and kept protected from light. The light used for activation of the photosensitiser was LumiSource™ (PCI Biotech), which contains four 18 W Osram L18/67 standard light tubes with a fluence rate of 13.5 mW/cm² and emits light at 435 nm.

Intradermal Photosensitisation and Immunisation of Mice

One day prior to the immunisation, spleens and lymph nodes were isolated from female OT-1 mice, and erythrocytes were removed by lysis (RBC Lysing Buffer HybriMax from Sigma-Aldrich) from the homogenised cell suspensions. The remaining cells were washed in PBS, filtered through 70 micron nylon strainers, and 2×10⁶ OT-1 cells were administered by intravenous injection into recipient female C57BLJ6 mice; the adoptive transfer of SIINFEKL-specific CD8 T cells facilitates monitoring of the immune response by flow cytometry. One day or 8 hours later, mice were bled by tail bleeding, and the blood was collected in heparin-containing tubes for analysis of the baseline frequency of OVA-specific CD8 T cells.

Then, the mice were shaved on the abdominal area, and the vaccines, consisting of OVA or of a mixture of OVA and $TPCS_{2a}$, were injected intradermally using syringes with 29G needles. The vaccines were kept light protected and used within 60 minutes of preparation. The vaccines were given in two injections of 50 µl each, on the left and right side of the abdominal mid line. OVA was tested at 10 to 100 µg per dose. The $TPCS_{2a}$ dose was 7.5 to 250 µg.

Figure 6:
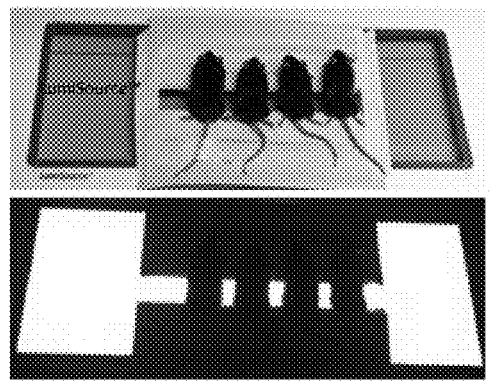

On day 0, prior to vaccination and on various days thereafter (e.g. day 6, 7, 8, 9, 14, 23, as indicated) mice were bled by tail bleeding and erythrocytes were removed by lysis, before analysis of antigen-specific CD8 T cells by flow cytometry. At the end of the experiment (typically 11, 12, 14 or 23 days), the mice were euthanized and the splenocytes analysed ex vivo. At various time points after the $TPCS_{2a}$ injection (0-48 hours), the mice were anaesthetised by intraperitoneal injection of a mixture of ketamine (25 mg/kg body weight) and xylazin (4 mg/kg) and placed on a light source (for illumination and activation of the photosensitiser $TPCS_{2a}$). The light dose was 6 minutes, if not otherwise stated. The whole procedure is illustrated in the scheme of FIG. 6A. The illumination of mice using LumiSource™ is imaged in FIG. 6B.

Analysis of Immune Responses

The frequency of OVA-specific CD8 T-cells in blood was monitored by staining the cells with anti-CD8 antibody and $H-2K^b$/SIINFEKL ProS pentamer (Proimmune, Oxford, UK) for analysis by flow cytometry. The activation status of the cells was further analysed by testing the expression of CD44 and CD69 by flow cytometry. Intracellular staining for IFN-γ was done after overnight stimulation of splenocytes in 24-well plates with the CD8 epitope $OVA_{257-264}$ (SIINFEKL) at 37° C. Brefeldin A was added during the last 4 hours. The cells were then washed and fixed with 4% formaldehyde in PBS for 10 min on ice. Anti-CD16/32 was added to block unspecific binding to Fc receptors. The cells were then permeabilised with 0.1% NP40 in PBS for 3 min and washed before staining with anti-IFN-γ, anti-CD8 and ant-CD44 antibodies (eBioscience or BD Pharmingen). The cells were acquired using FACSCanto (BD Biosciences, San Jose, USA) and analysed using FlowJo 8.5.2 software (Tree Star, Inc., Ashland, Oreg.).

Alternatively, 2×10⁵ splenocytes were re-stimulated in 96-well plates with OVA protein or the SIINFEKL. After 24 and 72 hours, supernatants were collected and analysed for IL-2 or IFN-γ by ELISA (eBioscience—performed according to the manufacturer's instructions).

Live Cell Fluorescence Microscopy

Fifty thousand J774.1 cells (ATCC no. TIB-67 mouse monocyte macrophage cell line) were seeded out on no. 1.5 glass coverslips (Glasswarenfabrik Karl Hecht KG, Sondheim, Germany) in 4-well plates overnight. The cells were incubated with 0.05 or 1,0 µg/ml $TPCS_{2a}$ for 18 hours and washed three times in drug-free culture medium prior to incubation with 25 µg/ml OVA-Alexa488 for four hours. Cells were subsequently washed in ice-cold PBS with $Ca^{2+}$ and $Mg^{2+}$ prior to microscopy. Images of cellular localization and PCI-induced cytosolic release of OVA was obtained by epi-fluorescence microscopy using a Plan-Apochromat 63×/1.40 Oil differential interference contrast (DIC) objective or 40×/0.95 Plan-Apochromat phase contrast (Korr Ph3 M27) objective with a Zeiss Axioimager Z.1 microscope (Carl Zeiss, Oberkochen, Germany). Fluorescence of Alexa488-labelled OVA was obtained by using a 470/40 nm band pass (BP) excitation filter with a beam splitter at 495 nm and a 525/50 nm BP emission filter. $TPCS_{2a}$ fluorescence was obtained by using a 395-440 nm BP excitation filter with a beam splitter at 460 nm, and a 620 nm long pass filter. Micrographs were recorded with a digital AxioCam MRm camera and processed and analysed by use of the Axiovision Software (Carl Zeiss).

Vaccination and Effect on Tumour Growth

Animals were immunised intradermally as described above with 10 µg OVA with or without 200 µg $TPCS_{2a}$. The abdominal region was illuminated for six minutes 18 hours after vaccination. One day prior to vaccination, the mice received 10,000 OT-I cells intravenously. On day four after vaccination, the mice received 5×105 SIINFEKL-expressing B16 mouse melanoma cells by intradermal injection into one of the flanks. The B16 melanoma cell line is of spontaneous origin in C57BL/6 mice, and the SIINFEKL-expressing line was kindly provided by Emmanuel Contassot (University of Zurich). The growth of the solid tumour was monitored by measuring the tumour size by calliper 14 days after tumour injection, the endpoint of the investigation. The tumour volume was calculated using use of the modified ellipsoid formula: (length×width²)/2.

Results

Analysis of the Effect of the Length of Immunisation Before Illumination on the PCI-Mediated Generation of an Immune Response.

To facilitate analysis of MHC-class I antigen presentation, we used the class-I binding octapeptide SIINFEKL from OVA (aa257-264) in combination with SIINFEKL—specific CD8 T cells from T-cell receptor transgenic OT-I mice. OT-I lymphocytes were purified from OT-I mice, and 2×10⁶ cells were adoptively transferred to syngeneic and sex-matched wild type C57BL/6 mice. One day after the transfer approximately 1.4% of all CD8-positive T cells in peripheral blood was SIINFEKL-specific (FIG. 7A); the frequency of SIINFEKL-specific CD8 T cells in C57BL/6 mice, which did not receive an adoptive transfer of OT-I cells was less than 0.05% (data not shown).

Figure 7:
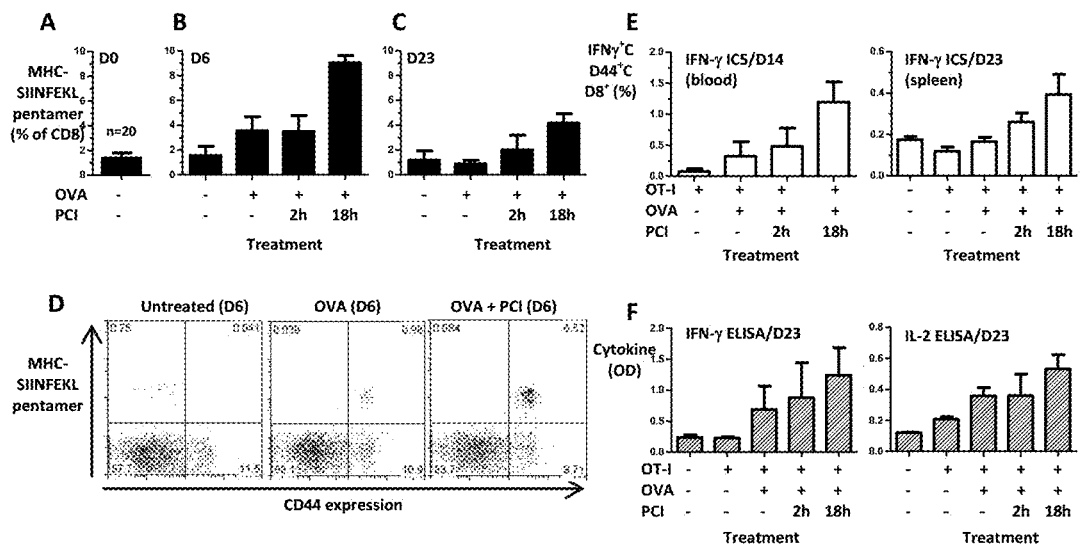

The mice were then typically immunised with 10-100 µg OVA protein or with a mixture of OVA and 7.5-250 µg of the photosensitiser $TPCS_{2a}$ by intradermal administration in the abdominal region. At different time point thereafter, the mice were anaesthetised and placed belly-down onto the light source, and the site of vaccination was illuminated for six minutes. By day six after vaccination, the frequency of SIINFEKL-specific CD8 T cells in the peripheral blood of mice vaccinated 100 OVA µg had increased to approximately 3.5% (FIG. 7B). A similar frequency was measured in mice that also received 25 µg TPCS$_{2a}$ and were illuminated two hours after vaccination (FIG. 7B). However, when mice were illuminated 18 hours post-vaccination, a significant increase in the number of SIINFEKL-specific CD8 T cells was measured in blood (FIG. 7C; P=0.0286 by Mann Whitney). Typically, a retraction of the number of SIINFEKL-specific CD8 T cells in blood was observed 10-15 days after vaccination. By day 23 post-vaccination, the numbers of antigen-specific CD8 T cells had retracted to baseline levels in mice immunised with OVA alone or OVA plus TPCS$_{2a}$ and illuminated two hours after administration (FIG. 7C). Also, mice immunised with OVA and TPCS$_{2a}$ and illuminated at 18 hours after immunization showed reduced frequencies after 23 days, but still significantly higher than baseline (P=0.0294 by Mann Whitney). While the SIINFEKL-specific cells in blood had a non-activated phenotype with lack of activation markers such as CD44 (FIG. 7D), CD25 and CD69 (not shown), both immunisation with OVA and OVA-PCI caused strong up-regulation of these markers by day six.

On day 14, the mice were bled and the PBMCs cells re-stimulated with SIINFEKL overnight. After staining for surface CD8 and CD44 and intracellular IFN-γ, the cells were acquired by flow cytometry and the frequency of triple-positive cells within all CD8-positive cells was calculated. OVA-immunised mice had a 4-fold increased frequency as compared to control mice that had received OT-I transfer only (FIG. 7E, left panel). The increase in IFN-γ-producing CD44-positive cells after PCI treatment was 6-fold (illumination at 2 hours) and 15-fold (18 hours).

On day 23, mice were euthanized and splenocytes cultured overnight with SIINFEKL. The cells were then analysed for intracellular IFN-γ by flow cytometry (FIG. 7E, right panel) or for the secretion of IL-2 (24 hours) and IFN-γ (72 hours) by ELISA (FIG. 7F). The intracellular IFN-γ staining showed barely detectable frequencies of CD44-positive IFN-γ producing cells in splenocytes from OVA-immunised mice that did not receive parallel PCI treatment (FIG. 7E, right panel). Clearly higher frequencies of IFN-γ producing cells were detected in splenocytes from mice that received PCI-treatment. Again, 18 hours interval between immunisation and illumination was most beneficial. Splenocytes from all OVA-immunised mice showed significant production of both IL-2 and IFN-γ when compared to non-immunised OT-I recipients. Although not statistically significant, there was a clear tendency for increased cytokine secretion in splenocytes from mice that were also PCI-treated.

Since immunisation with PCI did not produce good responders in all animals tested (typically 3-4 out of 5), we further tested the effect of the time interval between TPCS$_{2a}$ administration and illumination on the stimulated immune response. Intervals of 6-8 hours or of 42 hours did not suggest an adjuvant effect for PCI (data not shown). Repeatedly, an interval of approximately 18 hours was required to gain an adjuvant effect of PCI. This was observed without exceptions in four independent experiments.

Analysis of the Effect of the Ddose of Photosensitizer on the PCI-Mediated Generation of an Immune Response.

Figure 8:
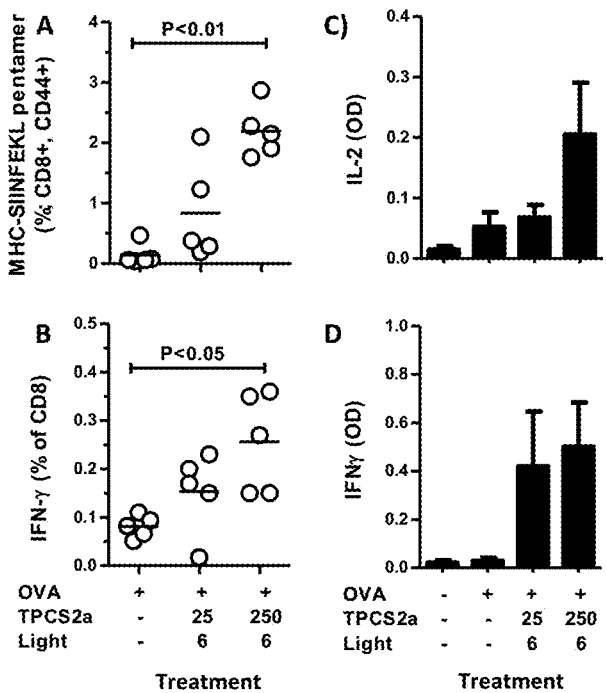

We then reduced the OVA immunisation dose in order to titrate out the effect of OVA and increasing doses of TPCS$_{2a}$ was titrated into the vaccine. Immunisation with 10 µg OVA alone produced no measurable effect on SIINFEKL-specific CD8 T cells in blood as compared to untreated animals (data not shown). Several experiments with TPCS$_{2a}$ at 10, 25, 50, 100 and 250 µg showed that increasing TPCS$_{2a}$ doses also increased the measured OVA-specific immune response (data not shown). Representatively, PCI with 25 µg TPCS$_{2a}$ caused 40% good responders, 40% week responders and 20% non-responders as measured for SIINFEKL-specific CD8 T cells in blood on day 8, while PCI with 250 µg TPCS$_{2a}$ produced 100% good responders (FIG. 8A). On day 11 the splenocytes were tested by flow cytometry for IFN-γ production. Immunisation with OVA alone showed weak responders in all mice tested, whereas immunisation with OVA and PCI caused better responders in nine out of ten (90%) mice tested (FIG. 8B). Again, PCI with 250 µg TPCS$_{2a}$ showed 100% responders and the highest frequency of IFN-γ producing cells. Whereas intracellular staining and flow cytometry qualitatively measures whether cells can produce cytokines, ELISA measures how much cytokine the cell can produce. We therefore re-stimulated the day 11 splenocytes with SIINFEKL in vitro and analysed IL-2 (FIG. 8C) and IFN-γ (FIG. 8D) after 24 and 72 hours, respectively. Immunisation with OVA alone produced weak but clearly measurable IL-2, but not IFN-γ secretion. Immunisation with OVA and PCI at 25 µg TPCS$_{2a}$ did not cause an increase in IL-2, but a strong increase in IFN-γ secretion as compared to immunisation with OVA alone. At 250 µg TPCS$_{2a}$, strong secretion of both IL-2 and IFN-γ was detected. Finally, while PCI with TPCS$_{2a}$ had a dose-dependent adjuvant effect with regards to the immune response measured, higher TPCS$_{2a}$ doses also caused more local inflammation with transient erythema on days 1-3 after illumination (data not shown).

Figure 9:
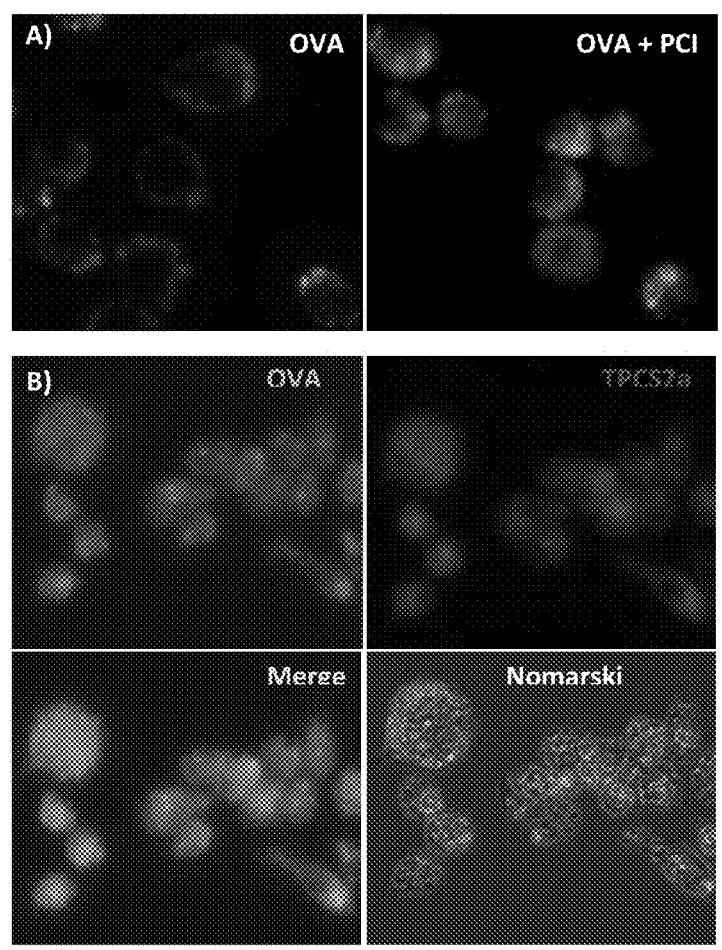

To study the mechanism by which PCI mediates the adjuvant effect, murine J774 cells, an antigen-presenting macrophage cell line, were incubated with Alexa488-labelled OVA with or without parallel PCI treatment. As shown in the fluorescence micrograph of FIG. 9A, in cells treated with OVA alone, antigen uptake was observed and the antigen was located close to the cell surface in concise spherical shaped bodies, suggesting that the antigen was contained in vesicles, e.g. endosomes. After parallel PCI treatment of the cells, cytosol and in some cases also the nucleus have diffuse green fluorescence suggesting that the antigen is freely floating in the cytosol, hence, released from the endosomes. Since the photosensitiser TPCS$_{2a}$ is autofluorescent, it enabled the study of the relative localisation of antigen and TPCS$_{2a}$ after incubation of J774 cells with Alexa488-labelled OVA (green) and the photosensitiser (red). Again, after light activation of sensitised cells, the antigen showed a diffuse distribution throughout the cytosol and the nucleus (FIG. 9B). The TPCS$_{2a}$ photosensitiser showed a similar distribution and the merge of the two images demonstrates that antigen and photosensitiser are co-localised.

Further analysis of the effect of the length of immunisation before illumination on the PCI-mediated generation of an immune response.

To further examine the effect of the incubation time prior to illumination, a further study was conducted as generally described above but using 25 µg TPCS$_{2a}$, 100 µg OVA, 6 minutes illumination time, and 2, 6 or 18 hours incubation time. FIG. 10 shows results with C57BL/6 mice that were spiked with 5×10$^6$ OT-I cells. After 18 hours, the mice were immunised with 100 µg OVA, or with 100 µg OVA and 25µg TPCS$_{2a}$; control mice were left untreated. After 2, 6 or 18 hours, the TPCS$_2$-treated mice were illuminated. On day 0 and day 7 mice were bled and the cells stained with anti-CD8 antibodies and MHC I-SIINFEKL pentamer and assessed by flow cytometry analysis (A). On days 0, 7, 14 blood cells and day 23 splenocytes were stained with anti-CD8 antibodies and MHC I-SIINFEKL pentamer and assessed by flow cytometry (B). Individual circles in this and other figures show the results for individual animals. It can be seen that 18 hours incubation time produced an increase in antigen-specific CTLs.

Further Analysis of the Effect of the Length of Immunisation Before Illumination on the PCI-Mediated Generation of an Immune Response.

A similar study to the above study was carried out to further test different times of incubation prior to illumination. Time points of 18 hours and 42 hours after illumination were assayed (FIG. 11). On day 0 and day 7 mice were bled and stained with MHC I-SIINFEKL pentamer and anti-CD8 antibodies and assessed by flow cytometry (A) On days 0 and 7 blood cells and day 14 splenocytes cells were stained with anti-CD8 antibodies and pentamer and analysed by flow cytometry (B). (C) shows splenocytes that were re-stimulated overnight with SIINFEKL and analysed for IFN-γ by ELISA. IFN-γ was also analysed on day 14 by flow cytometry (D).

Analysis of the Effect of the Length of Illumination on the PCI-Mediated Generation of an Immune Response.

A similar study to the above study was carried out to test the illumination time, which was varied between 3, 6 and 12 minutes (incubation time was 18 hours) (FIG. 12). On days 0 and 9 blood cells and day 14 splenocytes were analysed for MHC I-SIINFEKL pentamer and CD8 staining by flow cytometry (A). On day 0 and day 9 mice were bled and stained with MHC I-SIINFEKL pentamer and anti-CD8 antibodies and analyzed by flow cytometry (B). (C) shows splenocytes (day 14) that were re-stimulated overnight with SIINFEKL and analysed for IL-2 and IFN-γ by ELISA.

Analysis of the Effect of the Photosensitizer Dose on the PCI-Mediated Generation of an Immune Response.

Figure 13A:
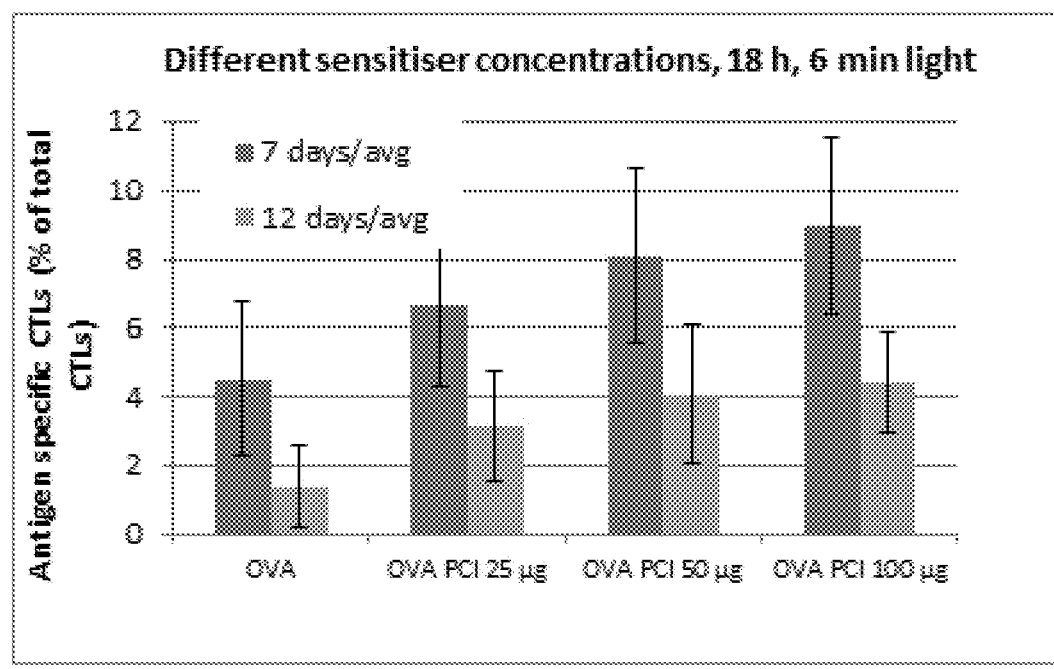
Figure 13B:
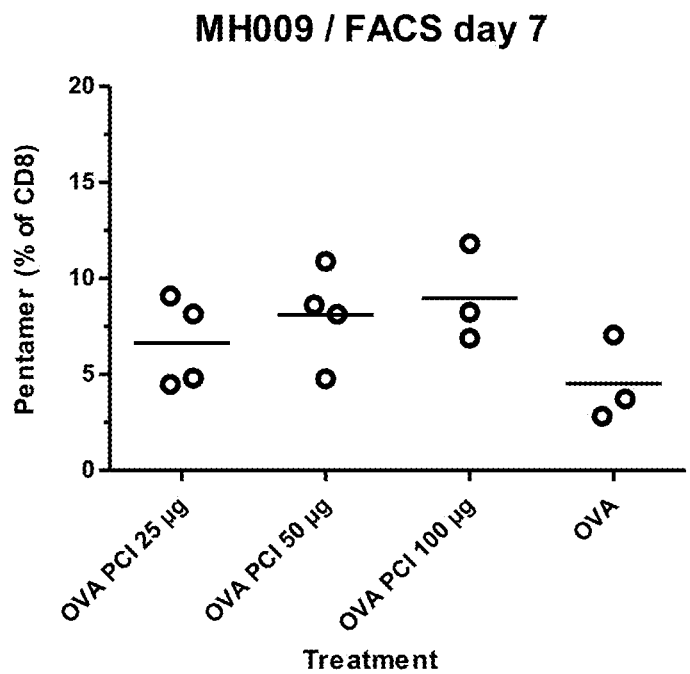
Figure 13C:
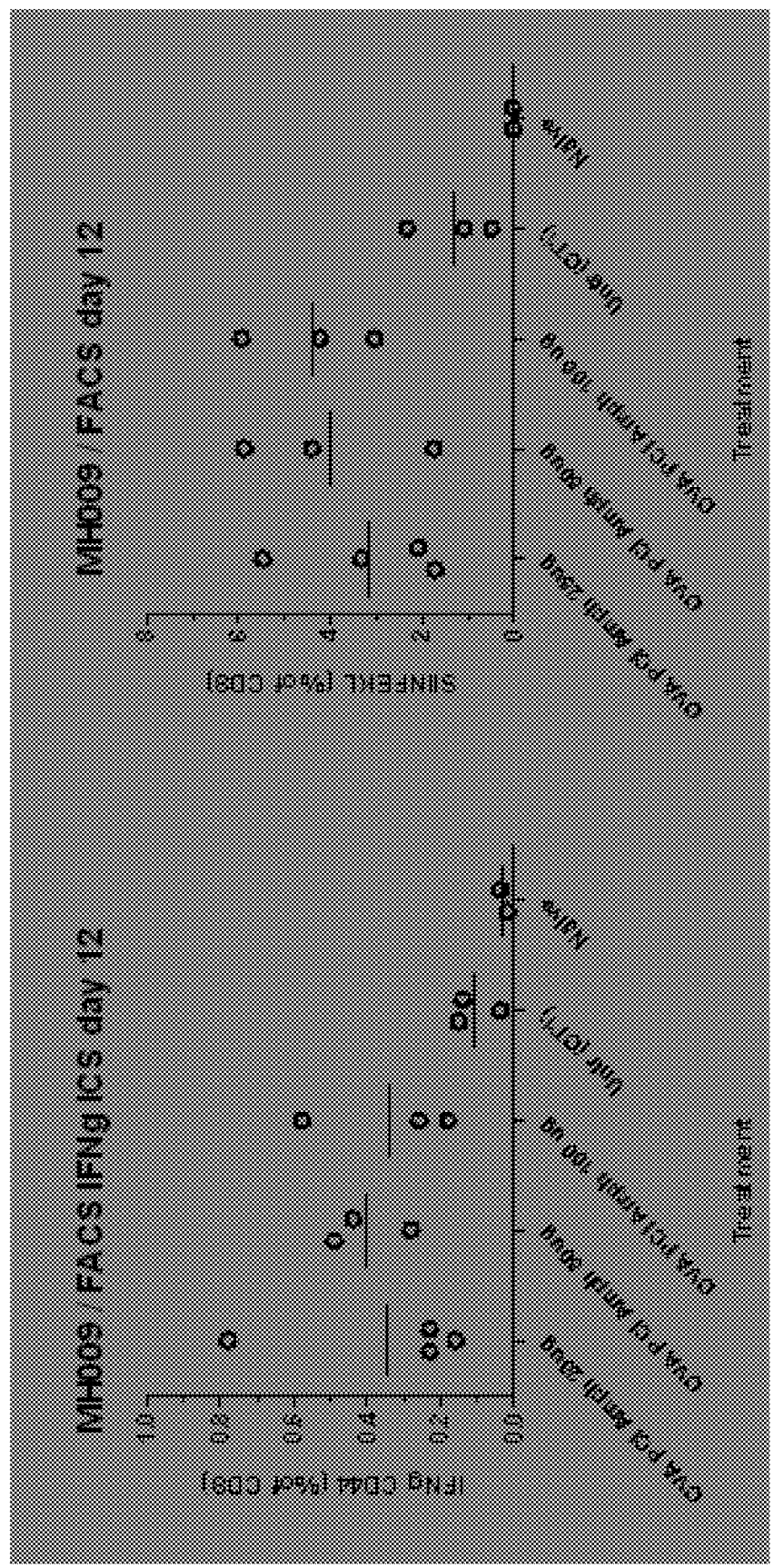

A similar study was carried out to test the photosensitiser dose, which was varied between 25, 50 and 100 μg TPCS$_{2a}$ (FIG. 13). An illumination time of 6 minutes and incubation time of 18 hours was used. On day 7 the mice were bled and blood cells stained with MHC I-SIINFEKL pentamer and anti-CD8 antibodies and assessed by flow cytometry (A). On day 7 blood cells were stained with anti-CD8 antibodies and pentamer analysed by flow cytometry (B). On day 12 splenocytes were analysed for IFN-γ, CD8 and CD44 staining (left panel) and MHC I-SIINFEKL pentamer and CD8 staining, (right panel) by flow cytometry (C).

Analysis of the Length of the Adjuvant Effect of PCI

Figure 14:
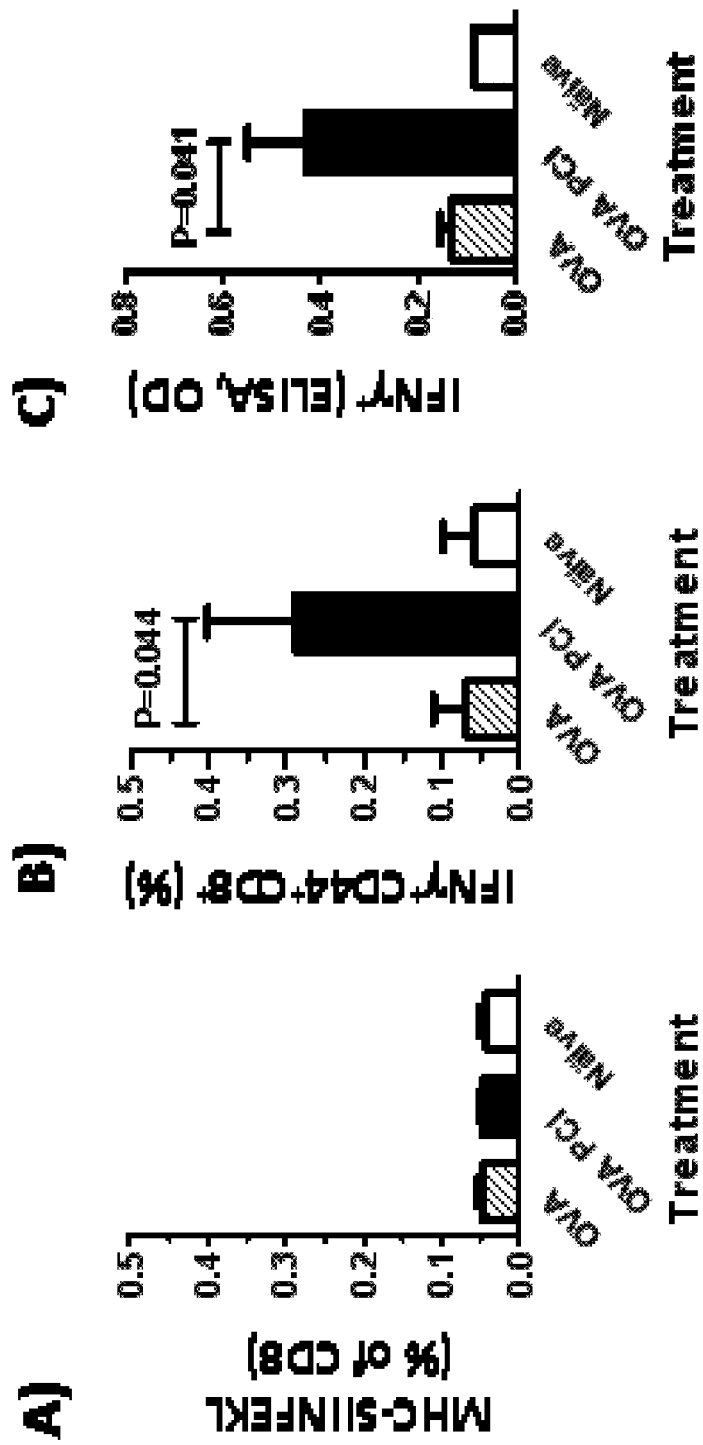

The longevity of the memory of the observed CD8-positive immune responses was tested in mice immunised as described above using 20 μg OVA with or without 200 μg TPCS$_{2a}$. The abdominal region was illuminated for six minutes 18 hours after vaccination. After 54 days, the mice were euthanized and the splenocytes analysed directly for the frequency and function of SIINFEKL-specific CD8 T cells. As shown in FIG. 14A, the frequencies of measurable SIINFEKL-specific CD8 T cells in mice treated with OVA or with OVA and PCI were not different from untreated mice. However, re-stimulation with SIINFEKL overnight revealed that PCI-treatment enabled stimulation of antigen-specific CD8 memory cells, which reacted by secretion of the effector cytokine IFN-γ. This was observed both by intracellular staining and flow cytometry (FIG. 14B) and by ELISA (FIG. 14C). By both assay, a statistically significant difference was observed between OVA alone and OVA-PCI treated mice (P<0.01).

Effect of Vaccination on Tumour Growth

Figure 15:
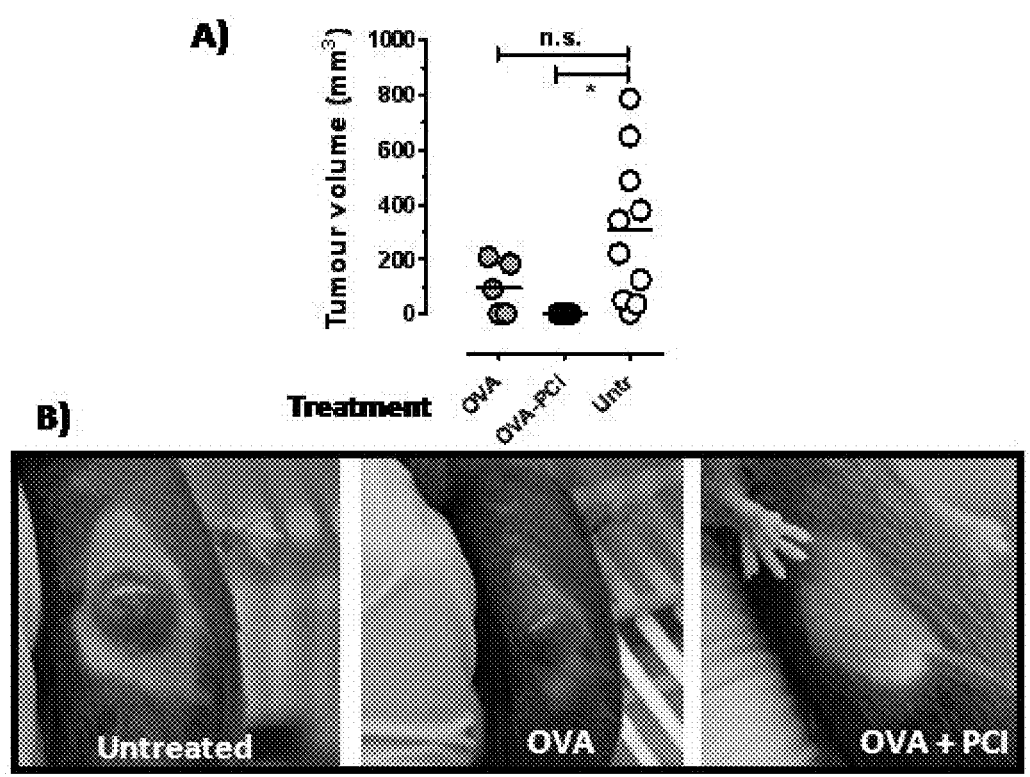

Mice received SIINFEKL-expressing mouse melanoma B16 cells four days after vaccination and the tumour growth was measured on day 14 post-injection of the melanoma cells. The results (FIG. 15) showed that PCI-based vaccination can prevent subsequent tumour growth. In non-vaccinated mice, the transfer of 2×10$^6$ OT-1 cells totally prevented B16 growth (data not shown). Therefore, the number of transferred cells was reduced to 1×10$^4$ OT-I cells. When compared to untreated controls, a significantly reduced B16 tumour growth was observed in mice that received PCI-based vaccination with OVA (P<0.05 by Kruskal-Wallis test) but not after vaccination with OVA alone (FIG. 15A). When all data were transformed to binary data (0=no growth); 1=growth) and analysed by the Chi-square test, PCI-based vaccination had a significantly stronger suppressing effect on tumour growth than vaccination with OVA alone (P=0.048). FIG. 15B shows representative micrographs of tumours on day 14 from differently treated mice.

Example 3

Similar methods to those described in Example 1 were carried out with minor variation in the doses and protocols.

Effect of Prophylactic Vaccination on Tumour Growth

Figure 16:
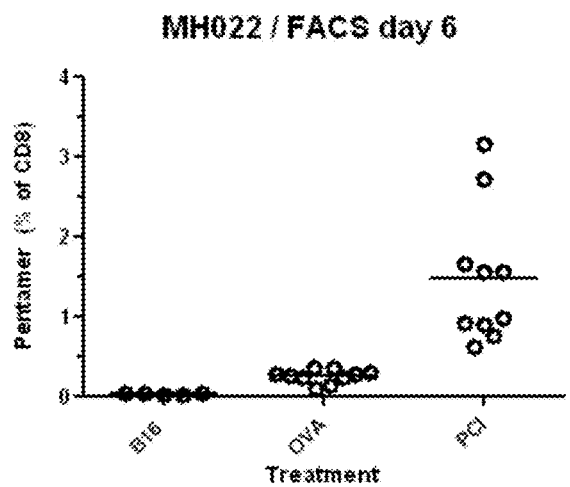
Figure 16:
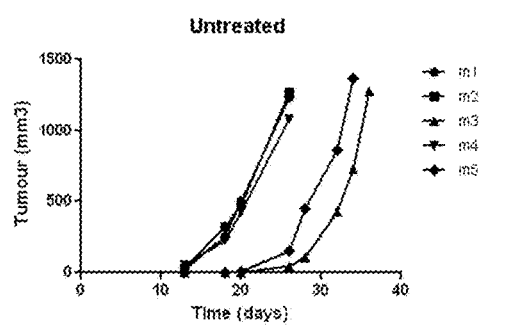
Figure 16:
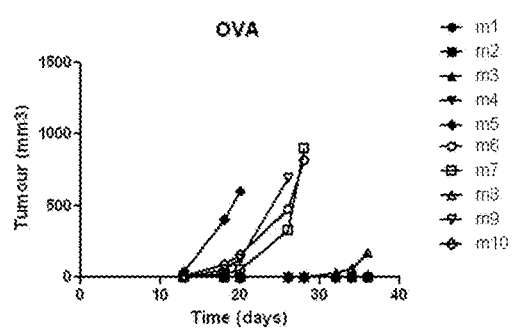
Figure 16:
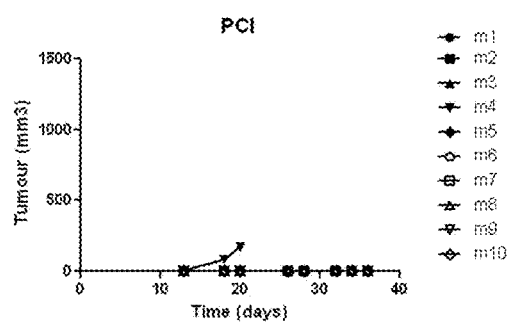
Figure 16:
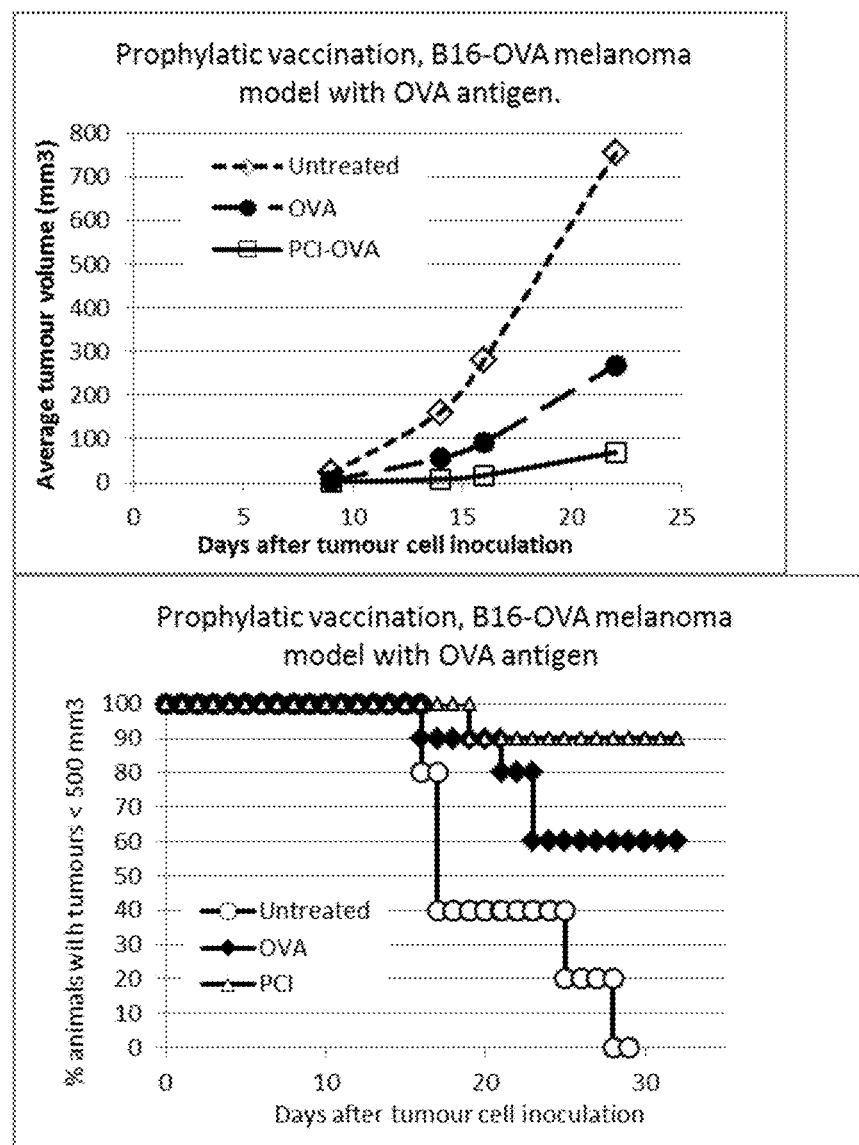

Female mice were given 1.0×10$^4$ OT-I cells i.v. one day prior to intradermal immunization with 150 μg TPCS$_{2a}$ and/or 10 μg OVA. The vaccine was given in two injections, each of 50 μl to the left and right of the abdominal mid line. The abdomen was shaved before vaccination. The abdominal region was illuminated for six minutes 18 hours after vaccination. On day 4 after immunization, the mice received 2.5×10$^5$ OVA-expressing B16 mouse melanoma cells by intradermal injection into the right flank. Two days later the mice were bled (by tail bleeding), and the frequency of OVA-specific CD8 T-cells was analyzed by flow cytometry (FIG. 16A). The tumour growth was monitored (B) from day 13 after vaccination until the volume of the tumours reached the endpoint, 1000 mm$^3$. On day 36 the experiment was ended. (C) shows the average tumour growth.

Figure 17:
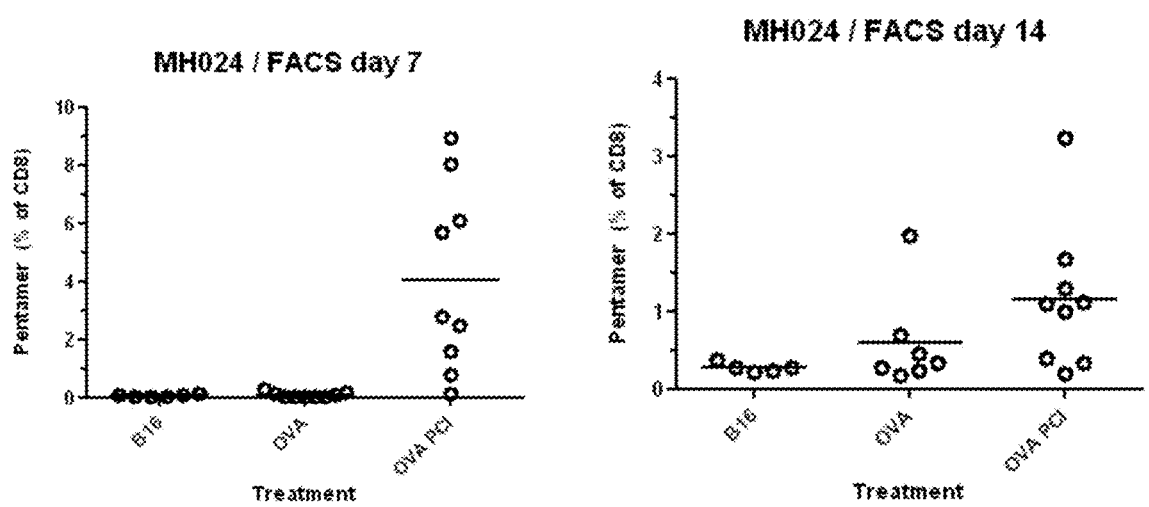
Figure 17:
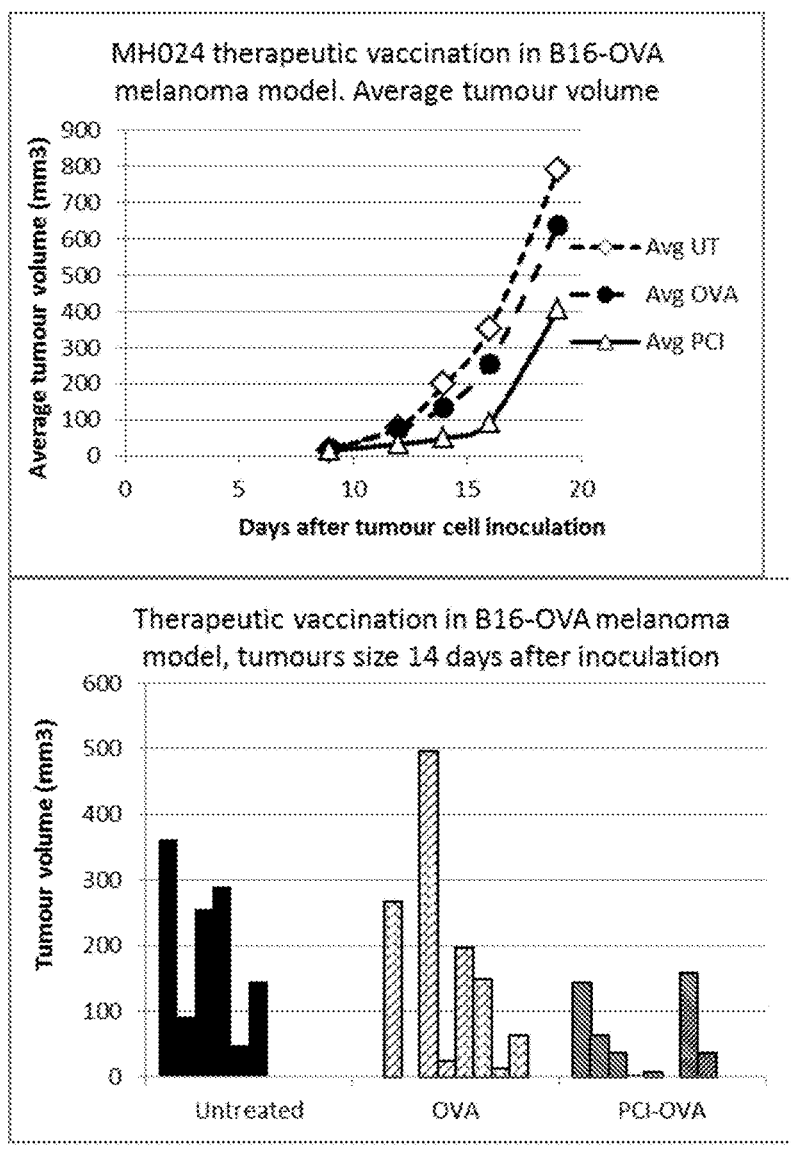

Effect of Therapeutic Vaccination on Tumour Size Female mice were given 1.0×10$^4$ OT-I cells i.v. one day prior to intradermal injection of 5.0×10$^5$ OVA-expressing B16 mouse melanoma cells into the right flank. One week later the mice were vaccinated intradermally with 150 μg TPCS$_{2a}$ and/or 10 μg OVA in the abdominal region. The vaccine was given in two injections, each of 50 μl to the left and right of the abdominal mid line. The abdomen was shaved before vaccination. The abdominal region was illuminated for six minutes 18 hours after vaccination. On days 7 and 14 after vaccination the animals were bled (by tail bleeding), and the frequency of OVA-specific CD8 T-cells was analyzed by flow cytometry (FIG. 17A). The tumour growth was monitored from day ten after injection of tumour cells until the volume of the tumours reached the endpoint, 1000 mm$^3$. On day 35 the experiment was terminated. (B) shows the average tumour growth.

Figure 18:
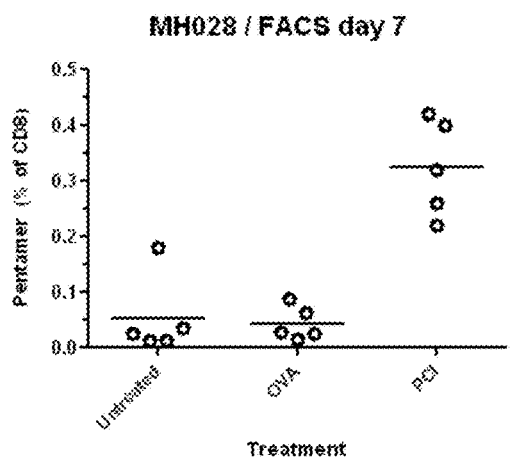

In a further study of prophylactic vaccination male mice were given 1.0×10$^4$ OT-I cells i.v. 6 hours before intradermal immunization with 150 μg TPCS$_{2a}$ and/or 10 μg OVA. The vaccine was given in two injections, each of 50 μl to the left and right of the abdominal mid line. The abdomen was shaved before vaccination. The abdominal region was illuminated for six minutes 18 hours after vaccination. On day 4 after immunization, the mice received 5.0×10$^5$ OVA-expressing B16 mouse melanoma cells by intradermal injection into the right flank. Two days later the mice were bled (by tail bleeding), and the frequency of OVA-specific CD8 T-cells analyzed by flow cytometry (FIG. 18). The tumour growth will be monitored from day 18 after vaccination.

Example 4

Materials and Methods

Animals

C57BLJ6 mice were as described in Example 1. OT-I mice were as described in Example 1 and were purchased from Taconic Europe (Ry, Denmark) or from Jackson Laboratories (Bar Harbor, Maine). All mice were kept under SPF conditions, and the procedures performed were approved by the veterinary authorities in Switzerland and Norway.

Materials and Cells

OVA and $TPCS_{2a}$ were as for Example 1 and $TPCS_{2a}$ was illuminated as described in Example 1. In addition, Poly(IC) (high MW) and CpG oligonucleotide ODN 2395 were from InvivoGen (San Diego, USA). ODN 2395 is a type C CpG ODN which has the sequence

(palindrome underlined). OVA, $TPCS_{2a}$ and when relevant Poly(IC) were mixed in PBS, kept light protected, and administered to mice within 60 minutes of preparation.

Intradermal Photosensitisation and Immunisation Of Mice

The preparation and administration of OT-1 cells to recipient female C57BL/6 mice and baseline analysis was as described in Example 2.

Then, the mice were shaved on the abdominal area, and the vaccines, consisting of OVA or of different mixtures of OVA, $TPCS_{2a}$, Poly(IC) (50 μg) or CpG oligonucleotide (50 μg) were injected intradermally using syringes with 29G needles. The vaccines were kept light protected and used within 60 minutes of preparation. The vaccines were given in two injections of 50 μl each, on the left and right side of the abdominal mid line. OVA was used at a dose of 10 or 100 μg, and the $TPCS_{2a}$ dose was 150 μg. 18 hours after the vaccine injection, the mice were anaesthetised by intraperitoneal injection of a mixture of ketamine (25 mg/kg body weight) and xylazin (4 mg/kg) and placed on the LumiSource light source (for illumination and activation of the photosensitiser $TPCS_{2a}$). The illumination time was 6 minutes.

On days 7 and 14 thereafter mice were bled by tail bleeding and erythrocytes were removed by lysis, before analysis of antigen-specific CD8 T cells by flow cytometry. At the end of the experiment (day 14), the mice were euthanized and the splenocytes analysed ex vivo.

Analysis of Immune Responses

The frequency of OVA-specific CD8 T-cells in blood was monitored by staining the cells with anti-CD8 antibody and $H-2K^b$/SIINFEKL ProS pentamer (Proimmune, Oxford, UK) for analysis by flow cytometry. The activation status of the cells was further analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

For ELISA analysis $2 \times 10^5$ splenocytes were re-stimulated in 96-well plates with 0.005 μg/ml of the SIINFEKL peptide. After 72 hours, supernatants were collected and analysed for IFN-γ by ELISA (eBioscience—performed according to the manufacturer's instructions).

Poly(IC) and CpG Experiment.

The experiment was performed as described under Materials and Methods, and mouse blood samples from day 7 after vaccination were analysed by flow cytometry as described. Spleen cells from day 14 were restimulated by SIINFEKL peptide and analysed by Interferon-gamma ELISA as described. All mice received OT-1 cells as described.

The following experimental groups were included:
1. Untreated: Mice received OT-1 cells, but were not vaccinated or illuminated.
2. OVA: Mice were vaccinated with 10 μg of OVA. They were not illuminated.
3. OVA 100 μg: Mice were vaccinated with a mixture of 100 μg OVA. They were not illuminated.
4. OVA 10 μg PCI: Mice were vaccinated with a mixture of 10 μg OVA+150 μg $TPCS_{2a}$. Illuminated as described.
5. CpG OVA: Mice were vaccinated with a mixture of 10 μg OVA+50 μg ODN2935 CpG oligonucleotide. They were not illuminated.
6. CpG OVA/PCI: Mice were vaccinated with a mixture of 10 μg OVA+50 μg ODN2935 CpG oligonucleotide+150 μg $TPCS_{2a}$. Illuminated as described.
7. Poly(IC) OVA: Mice were vaccinated with a mixture of 10 μg OVA+50 μg Poly(IC). They were not illuminated.
8. Poly(IC) OVA/PCI: Mice were vaccinated with a mixture of 10 μg OVA+50 μg Poly(IC)+150 μg $TPCS_{2a}$. Illuminated as described.

Figure 19A:
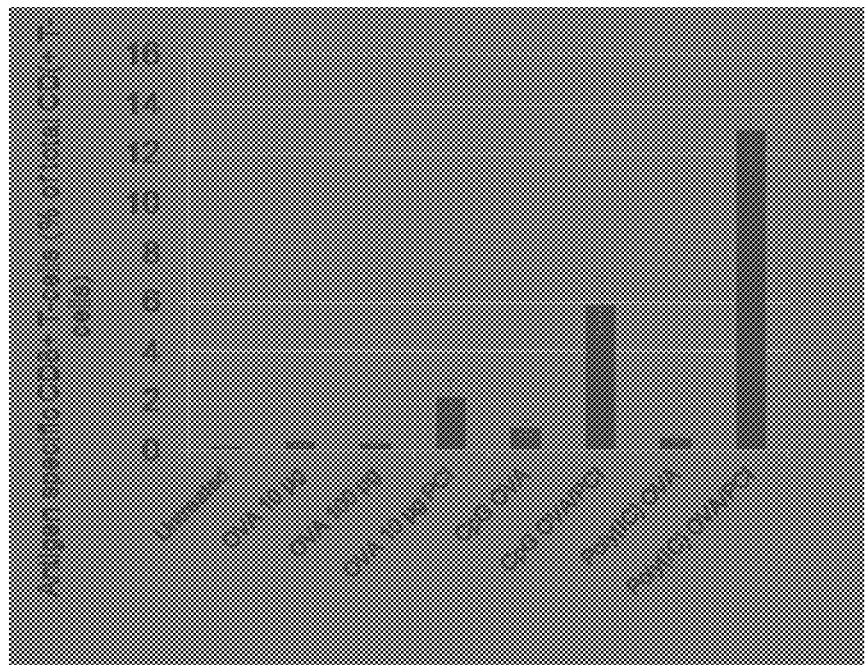

FIG. 19A shows the average values (% antigen-specific, $CD44^+$ cells of the total $CD8^+$ cells) for the experimental groups. It can be seen that the CpG and Poly(IC) adjuvants when used alone had only a very modest (for CpG) or no significant (for Poly(IC)) effect, and that PCI used alone was substantially more potent than either of these adjuvants. However, a clear synergistic effect was seen when PCI was used in combination with CpG or Poly(IC), and was most prominent for the combination PCI+Poly(IC).

Figure 19B:
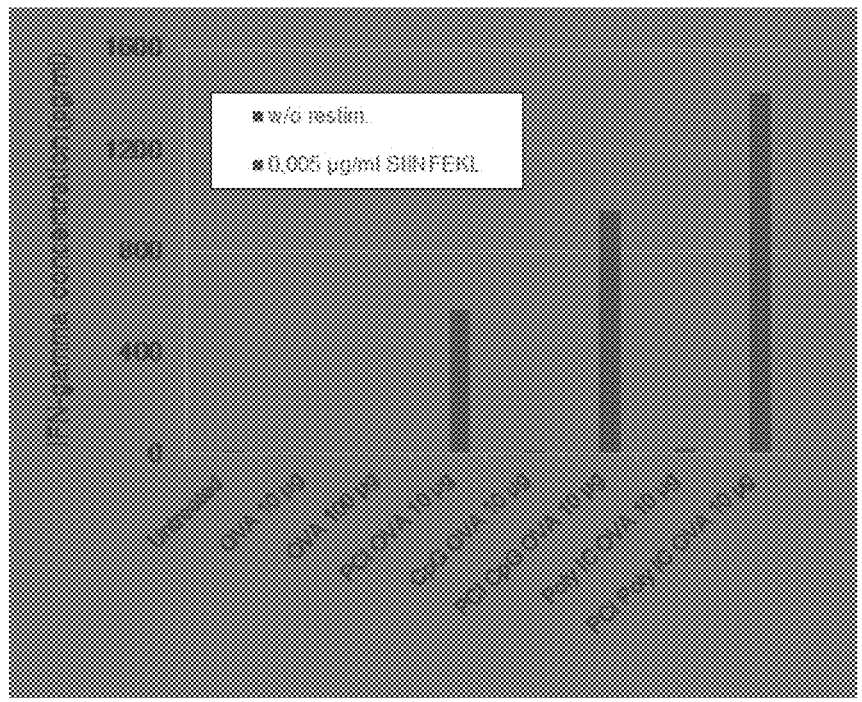

FIG. 19B shows the results from interferon-gamma (IFN-gamma) ELISA after restimulation of spleen cells with SIINFEKL peptide. Firstly it can be seen that the IFN-gamma production was totally dependent on restimulation (bars from unstimulated cells are barely visible), showing that the production was strictly antigen specific. It can also be seen that while there was virtually no effect with the cells from the CpG or Poly(IC) groups (nor with OVA alone), in all the PCI-treated groups a strong effect of restimulation could be observed, again with a synergistic effect in the PCI+CpG and the PCI+Poly(IC) groups, with the latter representing the better combination.

Example 5

Materials and Methods

C57BLJ6 mice, $TPCS_{2a}$ and OVA peptide were as described in Example 1. The TRP-2 peptide (sequence SVYDFFVWL) and gp100 (sequence KVPRNQDWL) was obtained from United Peptides (Herndon, Va.) and Poly(IC) (high molecular weight, average size of 1.5-8 kb) from InvivoGen (San Diego, USA).

Intradermal Photosensitisation and Immunisation of Normal Mice.

Preparation of the mice for immunization was performed as described in Example 2. The mice were shaved on the abdominal area and immunised at day 0 and at day 14 with a mixture of TRP-2 peptide and gp-100 peptide (50 µg of each), 100 µg TPCS$_{2a}$ and 10 µg poly(IC) as specified below by intradermal injection using syringes with 29G needles. The vaccines were kept light protected and used within 60 minutes of preparation. The vaccines were given in two injections of 50 µl each, on the left and right side of the abdominal mid line. At a specified time point after vaccine injection the mice were anaesthetised by intraperitoneal injection of a mixture of ketamine (25 mg/kg body weight) and xylazin (4 mg/kg) and illuminated where relevant.

Illumination of Immunised Mice.

Illumination with LumiSource was performed for 6 min, 18 hours after immunisation.

Analysis of Immune Responses by Pentamer Staining

On day 7 after immunisation mice were bled by tail bleeding and erythrocytes were removed by lysis. The frequency of antigen specific CD8 T-cells in the blood was monitored by flow cytometry after staining the cells with anti-CD8 and anti-CD44 antibodies and TRP-2 pentamers. The activation status of the cells was analysed by testing the expression of CD44 by flow cytometry. The cells were analysed using FACSCanto (BD Biosciences, San Jose, USA) and analysed using FlowJo 8.5.2 software (Tree Star, Inc., Ashland, Oreg.).

The following experimental groups were included:
1. Untreated TRP-2: Mice were not immunised or illuminated, blood samples were stained with TRP-2 pentamer.
2. TRP-2/poly(IC): Mice were immunised with a mixture of TRP-2 peptide and gp-100 peptide (50 µg of each), and 10 µg poly(IC). They were not illuminated. Blood samples were stained with TRP-2 pentamer.
3. TRP-2/PCI: Mice were immunised with a mixture of TRP-2 peptide and gp-100 peptide (50 µg of each) and 100 µg TPCS$_{2a}$ and illuminated. Blood samples were stained with TRP-2 pentamer.
4. TRP-2/poly(IC)/PCI: Mice were immunised with a mixture of TRP-2 peptide and gp-100 peptide (50 µg of each), 100 µg TPCS$_{2a}$ and 10 µg poly(IC) and illuminated. Blood samples were stained with TRP-2 pentamer.

Figure 20:
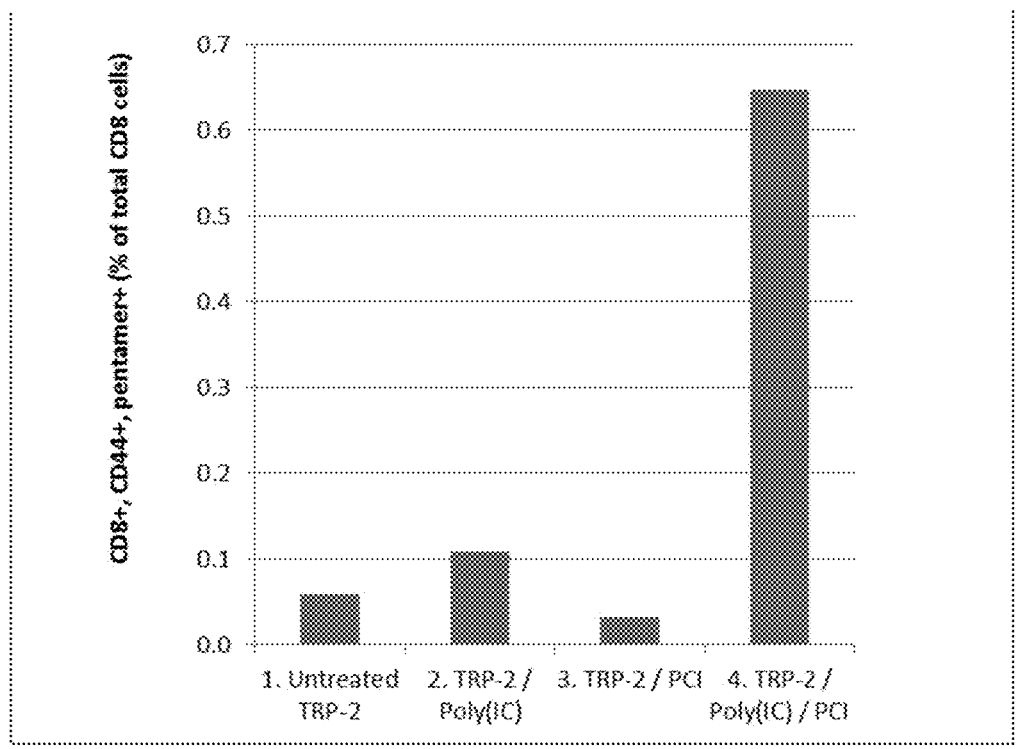

FIG. 20 shows the average values (% antigen-specific, CD44+ cells of the total CD8+ cells) for the TRP-2 pentamer stained experimental groups after the second immunisation. It can be seen that when the TRP-2 antigen was used with poly(IC) alone (group 2) or with PCI alone (group 3) no significant increase in antigen-specific cells were observed over what was seen in untreated animals. In comparison, the combination of poly(IC) and PCI (group 4) gave a clear synergistic effect leading to a significant increase in the number of antigen-specific CD8+ T-cells.

Example 6

Materials.

C57BLJ6 mice (Harlan Laboratories, Netherlands) and TPCS$_{2a}$ (PCI Biotech, Norway) were as described in Example 1. The TRP-2 peptide and Poly(IC) were as described in Example 5.

Intradermal Photosensitisation and Immunisation of Normal Mice.

Preparation of the mice for immunization was performed as described in Example 2. The mice were shaved on the abdominal area (3-4 cm$^2$) and immunised at day 0, day 14 and day 35 with 200 µg of TRP-2 peptide, 100 µg TPCS$_{2a}$ and 10 µg poly(IC) as specified below by intradermal injection using 0.3 ml BD Micro-Fine™+ insulin syringes with 30G needles (BD, NJ, USA). The vaccines were kept light protected and used within 60 minutes of preparation. The vaccines were given in two injections of 50 µl each, on the left and right side of the abdominal mid line. At a specified time point after vaccine injection the mice were anaesthetised by subcutaneous injection of a mixture of Zoletil (10 mg/kg body weight, Virbac, Norway) and illuminated where relevant.

Illumination of Immunised Mice.

Illumination of the vaccination site with LumiSource (PCI Biotech) was performed for 6 min, 18 hours after immunisation.

Analysis of Immune Responses by Pentamer Staining and Intracellular Staining.

On day 7 after each immunisation mice were bled by tail bleeding and erythrocytes were removed by lysis. The frequency of antigen specific CD8 T-cells in the blood was monitored by flow cytometry after staining the cells with anti-CD8 and anti-CD44 antibodies and TRP-2 pentamers. The activation status of the cells was analysed by testing the expression of CD44 by flow cytometry. The cells were analysed by using the BD LSRII flow cytometer with the FACSDiva software (BD Biosciences, San Jose, USA) and further analysed and processed using the FlowJo 8.5.2 software (Tree Star, Inc., Ashland, Oreg.).

On day 60 after the first immunisation the animals were sacrificed, the spleens were removed and the spleen cells were re-stimulated with the TRP-2 peptide and subsequently analysed with intracellular staining for interferon-gamma (IFN-gamma) as described in Example 2 and intracellular staining for tumour necrosis factor alpha (TNF-alpha) was performed as described for IFN-gamma using anti-TNF-alpha antibodies. (Antibodies against both TNF-alpha and IFN-gamma (carrying different fluorophores) were included in the same sample.)

The following experimental groups were included:
1. Untreated Mice were not immunised or illuminated.
2. TRP-2: Mice were immunised with 200 µg TRP-2 peptide in all immunisations. They were not illuminated.
3. TRP-2 + poly(IC): Mice were immunised with 200 µg TRP-2 peptide and 10 µg poly(IC). They were not illuminated.
4. TRP-2 + PCI: Mice were immunised with 200 µg TRP-2 peptide and 100 µg TPCS$_{2a}$ and illuminated.
5. TRP-2 + poly(IC) + PCI: Mice were immunised with 200 µg TRP-2 peptide, 10 µg poly(IC) and 100 µg TPCS$_{2a}$ and illuminated.

Figure 21:
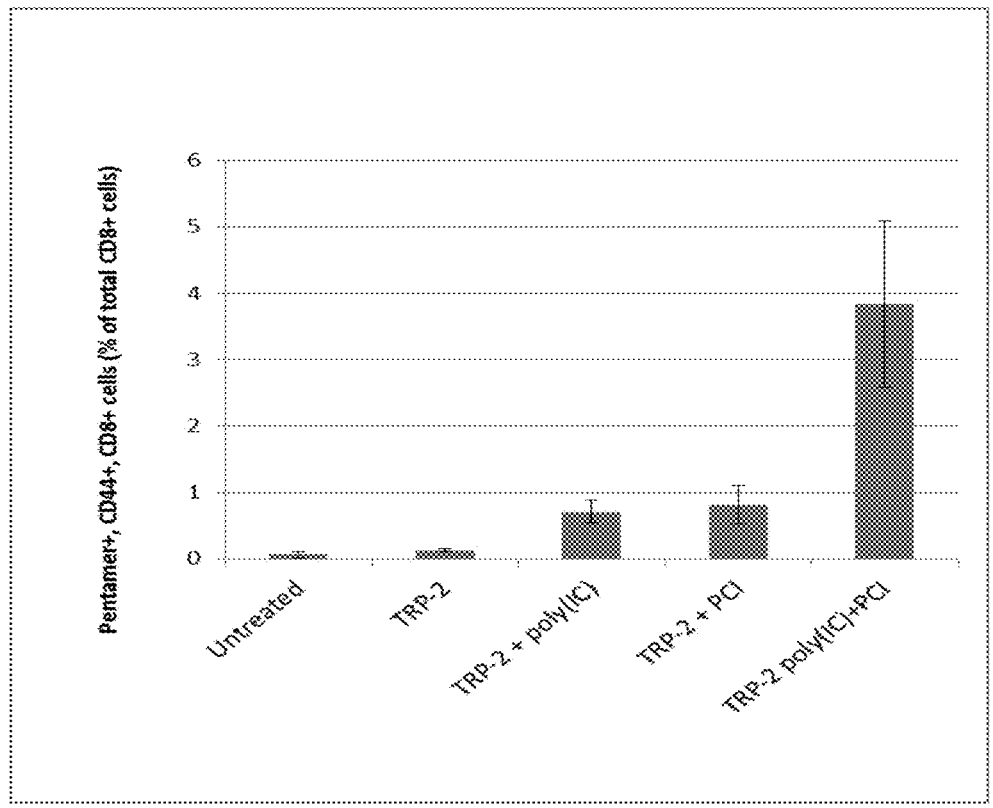

FIG. 21 shows the average values (% antigen-specific, CD44+cells of the total CD8+ cells) for the TRP-2 pentamer stained blood samples after the third immunisation. It can be seen that when the TRP-2 antigen was used with poly(IC) alone (group 3) or with PCI alone (group 4) a significant, but small increase in antigen-specific cells were observed over what was seen with antigen alone (group 2). In comparison, the combination of TRP-2, poly(IC) and PCI (group 5) gave a clear synergistic effect leading to a substantial (about 5 times) increase over what was seen with the individual treatments alone.

Figure 22:
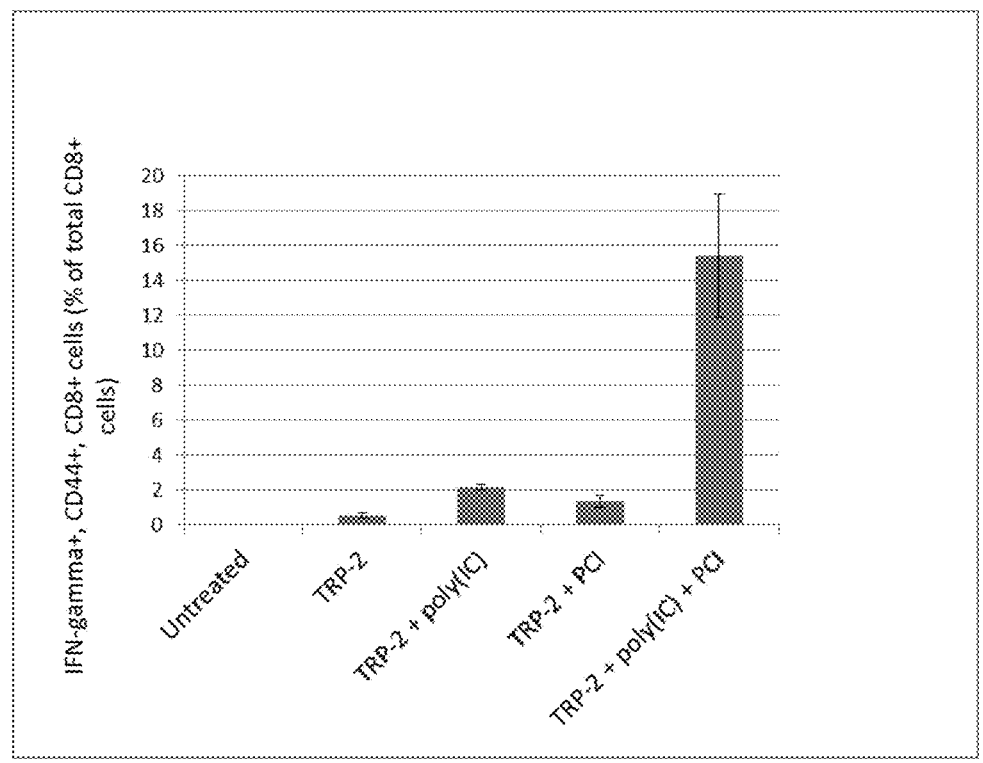
FIG. 22 shows results from the same study as FIG. 21. Interferon-gamma (IFN-gamma) intracellular staining after re-stimulation of spleen cells with the TRP-2 peptide is shown.

FIG. 22 shows the results from interferon-gamma (IFN-gamma) intracellular staining after re-stimulation of spleen cells with the TRP-2 peptide. It can be seen that when the TRP-2 antigen was used with poly(IC) alone (group 3) or with PCI alone (group 4) a small increase in the percentage of IFN-gamma producing cells were observed (over what was achieved with the TRP-2 peptide alone). Again, the combination of TRP-2, poly(IC) and PCI (group 5) gave a clear synergistic effect leading to a substantial (about 8 times) increase over what was seen with the best of the individual treatments alone (TRP-2 + poly(IC), group 3).

Figure 23:
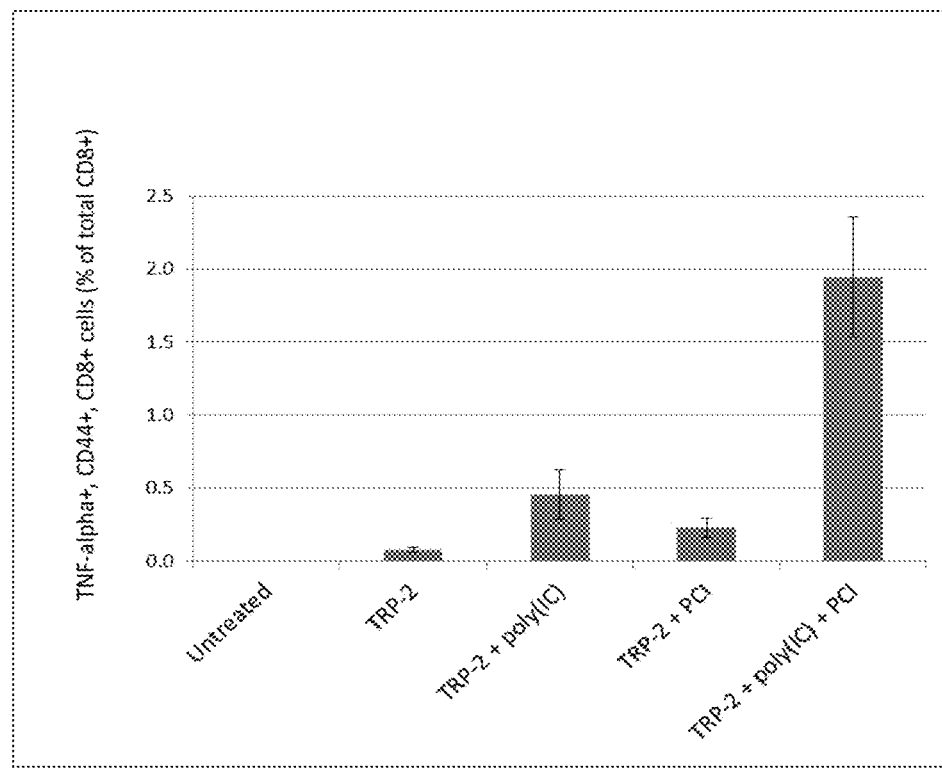
FIG. 23 shows results from the same study as FIG. 21. TNF-alpha intracellular staining after re-stimulation of spleen cells with the TRP-2 peptide is shown.

FIG. 23 shows the results from TNF-alpha intracellular staining after re-stimulation of spleen cells with the TRP-2 peptide. It can be seen that when the TRP-2 antigen was used with poly(IC) alone (group 3) or with PCI alone (group 4) a small increase in the percentage of TNF-alpha producing cells were observed (over what was achieved with the TRP-2 peptide alone). Again, the combination of TRP-2, poly(IC) and PCI (group 5) gave a clear synergistic effect leading to a substantial (about 6 times) increase over what was seen with the best of the individual treatments alone (TRP-2 + poly(IC), group 3).

Example 7 PCI-Mediated Prophylactic Vaccination with Melanoma Cell Extracts.

Materials and methods were as described in Example 6, where appropriate.

Preparation of Melanoma Cell Extract

B16-F10 mouse melanoma cells (as described in Example 1 but without OVA transfection/expression) were harvested when in the logarithmic growth phase i.e. cell culture flasks were ≤50% confluent. The medium was aspirated and the flask rinsed briefly with 2 ml trypsin/EDTA (0.25% (w/v) Trypsin-0.53 mM EDTA) and aspirated again. 2 ml trypsin/EDTA were added, tilting the flask to ensure that all cells were covered. The side of the flask was tapped periodically until cells detached and slid down the culturing surface. 12 ml cold CM (Dulbecco's Modified Eagle's Medium with 10% FBS) was added to neutralize the trypsin and the suspension was pipetted vigorously to obtain a single-cell suspension. The suspension was transferred to a 15-ml conical centrifuge tube and the cells were pelleted by centrifugation for 10 min at 528×g/1500 rpm (Rotina 380R, Hettich, Germany) at 4° C. The supernatant was decanted and the cell concentration was adjusted to $1 \times 10^7$/ml in ice-cold Hanks Balanced Salt Solution (5.4 mM KCl, 0.3 mM $Na_2HPO_4.7H_2O$, 0.4 mM $KH_2PO_4$, 4.2 mM $NaHCO_3$, 1.3 mM $CaCl_2$, 0.5 mM $MgCl_2.6H_2O$, 0.6 mM $MgSO_4.7H_2O$, 137 mM NaCl, 5.6 mM D-glucose, 0.02% phenol red; pH adjusted to 7.4 with 1 M HCl or 1 M NaOH).

Irradiation of B16-F10 cells was conducted with an X-ray generator (Faxitron CP160, 160kV, 6.3 mA, Arizona, USA) with a total dose of 50 Gy.

For mouse vaccination the irradiated cells were kept on ice before vaccination of 6- to 12-week-old female C57BL/6 mice.

Experimental Groups:

There were 5 mice in each experimental group. The mice were vaccinated twice (days 0 and 14) with a total of $1 \times 10^6$ cells B16-F10 cells per mouse per vaccination, divided in two 50 µL injections per mouse. The experimental groups were as follows:

Group 1: no treatment, no illumination.
Group 2: Irradiated B16-F10 cells, no illumination.
Group 3: Irradiated B16-F10 cells+10 µg Poly (IC), no illumination
Group 4: Irradiated B16-F10 cells+150 µg $TPCS_{2a}$+illumination.
Group 5: Irradiated B16-F10 cells+10 µg poly(IC)+150 µg $TPCS_{2a}$+illumination.

At day 21 $5 \times 10^5$ B16-F10 cells were injected intradermally, and the size of the tumours was measured at least 2 times per week. The results are shown with day 0 as the day the tumour cells were administered.

From FIG. 24 it can be seen that the tumours in the groups receiving PCI-mediated vaccination (groups 4 and 5) grew substantially slower than in the groups receiving the vaccine alone (group 2) or the vaccine with the poly(IC) adjuvant without PCI (group 3), both of which did not differ from the untreated animals.

The invention claimed is:

1. A method of treating melanoma in a subject, comprising
conducting photochemical internalisation (PCI) by administering to cells in said subject a melanoma antigen, a photosensitizing agent and a TLR ligand, and irradiating said cells in the subject with light of a wavelength effective to activate said photosensitizing agent under conditions which maintain the viability of the irradiated cells,
wherein said melanoma antigen or a part thereof is released into the cytosol of said cells and subsequently presented on the cells' surfaces and an immune response is generated which treats said melanoma, and
wherein the melanoma antigen is an antigen derived from a melanoma cell in the subject and may be obtained by isolation or synthesis and said administration is localized.

2. The method of claim 1 wherein said melanoma antigen and said photosensitising agent are administered to said subject simultaneously, separately or sequentially.

3. The method of claim 1 wherein said administration is by intradermal or intratumoural administration.

4. The method of claim 1 wherein said method is a method of vaccination.

5. The method of claim 4 wherein said method is a method of therapeutic vaccination.

6. The method of claim 1 wherein said subject is a mammal.

7. The method of claim 6 wherein said subject is a cat, dog, horse, donkey, sheep, pig, goat, cow, mouse, rat, rabbit or guinea pig.

8. The method of claim 6 wherein said subject is a human.

9. The method of claim 1 wherein said irradiation is for between 1 and 60 minutes.

10. The method of claim 1 wherein said irradiation is for 3 to 12 minutes.

11. The method of claim 1 wherein said irradiation is for 6 minutes.

12. The method of claim 1 wherein said melanoma antigen and said photosensitizing agent are administered to said subject 12-30 hours before said irradiation.

13. The method of claim 12 wherein said melanoma antigen and said photosensitizing agent are administered to said subject 16-20 hours before said irradiation.

14. The method of claim 13 wherein said melanoma antigen and said photosensitizing agent are administered to said subject 18 hours before said irradiation.

15. The method of claim 1 wherein said photosensitising agent is an amphiphilic porphyrin, chlorin, bacteriochlorin or phthalocyanine.

16. The method of claim 15 wherein said photosensitising agent is in the form of a conjugate with a chitosan derivative.

17. The method of claim 1 wherein said photosensitising agent is selected from $TPCS_{2a}$, $AlPcS_{2a}$, $TPPS_{2a}$ and $TPBS_{2a}$.

18. The method of claim 17 wherein said photosensitising agent is $TPCS_{2a}$.

19. The method of claim 1 wherein the photosensitizing agent is administered at a dose of between 25 and 400 µg.

20. The method of claim 19 wherein the dose of photosensitizing agent is between 100 and 300 µg.

21. The method of claim 20 wherein the dose of photosensitizing agent is 250 µg.

22. The method of claim 1 wherein the melanoma antigen is administered at a dose of between 1 and 500 µg.

23. The method of claim 22 wherein the dose of the melanoma antigen is between 10 and 100 µg.

24. The method of claim 23 wherein the dose of the melanoma antigen is 100 µg.

25. The method of claim 1 wherein the melanoma antigen is
(i) obtained from a subject,
(ii) derived from one or more melanoma cell lines, or (iii) selected from gp100, MAGE-1, MAGE-3, Melan-A, tyrosinase and tyrosinase-related protein (TRP) 1 or 2 or an antigen comprising a peptide epitope thereof.

26. The method of claim 25 wherein when said melanoma antigen is derived from a subject or one or more melanoma cell lines said method additionally includes the step of preparing a composition comprising one or more melanoma antigens from one or more subjects or from one or more melanoma cell lines.

27. The method of claim 25 wherein the melanoma antigen is TRP-2.

28. The method of claim 1 wherein the TLR ligand is poly(IC).

29. The method of claim 1 for treating metastatic melanoma.

30. A method of treating melanoma in a subject, comprising
administering to said subject a cell or population of cells obtainable by a method in which a cell is subjected to photochemical internalisation (PCI) by contacting said cell with a melanoma antigen, a photosensitizing agent and a TLR ligand and the cell is irradiated with light of a wavelength effective to activate the photosensitising agent under conditions which maintain the viability of the irradiated cell,
wherein said melanoma antigen or a part thereof is released into the cytosol of the cell and subsequently presented on the surface of the cell, and
wherein the melanoma antigen is an antigen derived from a melanoma cell in the subject and may be obtained by isolation or synthesis.

31. The method of claim 30 wherein the cell is a dendritic cell.

32. The method of claim 30 wherein said photosensitising agent is selected from TPCS2a, AlPcS2a, TPPS2a and TPBS2a.

33. The method of claim 32 wherein said photosensitising agent is $TPCS2_a$.

34. The method of claim 30 wherein the melanoma antigen is
(i) obtained from a subject,
(ii) derived from one or more melanoma cell lines, or
(iii) selected from gp100, MAGE-1, MAGE-3, Melan-A, tyrosinase and tyrosinase-related protein (TRP) 1 or 2 or an antigen comprising a peptide epitope thereof.

35. The method of claim 34 wherein when said melanoma antigen is derived from a subject or one or more melanoma cell lines said method additionally includes the step of preparing a composition comprising one or more melanoma antigens from one or more subjects or from one or more melanoma cell lines.

36. The method of claim 34 wherein the melanoma antigen is TRP-2.

37. The method of claim 30 wherein the TLR ligand is poly(IC).

38. The method of claim 30 for treating metastatic melanoma.

* * * * *